US012575905B2

(12) United States Patent
Zheng et al.

(10) Patent No.: US 12,575,905 B2
(45) Date of Patent: Mar. 17, 2026

(54) HAND-MANIPULATED INPUT DEVICE WITH HALL EFFECT SENSOR FOR ROBOTIC SYSTEM

(71) Applicant: Auris Health, Inc., Redwood City, CA (US)

(72) Inventors: Qingbin Zheng, Santa Clara, CA (US); Joseph L. Diamond, San Carlos, CA (US); Hossein Taheri, Foster City, CA (US); Nicklas Hsieh, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 1182 days.

(21) Appl. No.: 17/214,799

(22) Filed: Mar. 26, 2021

(65) Prior Publication Data

US 2021/0298857 A1 Sep. 30, 2021

Related U.S. Application Data

(60) Provisional application No. 63/000,769, filed on Mar. 27, 2020.

(51) Int. Cl.
*A61B 34/00* (2016.01)
*A61B 17/00* (2006.01)
(Continued)

(52) U.S. Cl.
CPC .............. *A61B 34/74* (2016.02); *A61B 34/37* (2016.02); *G05G 9/02* (2013.01);
(Continued)

(58) Field of Classification Search
CPC ... A61B 34/74; A61B 34/37; A61B 2034/301; A61B 2034/302; A61B 2034/303; A61B 2034/743; A61B 2017/00039; G05G 9/02
See application file for complete search history.

(56) References Cited

U.S. PATENT DOCUMENTS 6,659,939 B2 12/2003 Moll et al.
7,955,322 B2 6/2011 Devengenzo et al.
(Continued)

FOREIGN PATENT DOCUMENTS

EP 2772214 B1 * 10/2018 ....... A61B 17/00234
KR 10-2015-0097238 A 8/2015
(Continued)

OTHER PUBLICATIONS

Data Sheet for the Infineon TLV493D-A1B6 3D Magnetic Sensor (Infineon. Low Power 3D Magnetic Sensor with I2C Interface, TLV493D-A1B6 3D Magnetic Sensor Data Sheet. https://www.infineon.com/cms/en/product/sensor/magnetic-sensors/magnetic-position-sensors/3d-magnetics/tlv493d-a1b6/) (Year: 2019).*
(Continued)

*Primary Examiner* — Lindsey G Wehrheim
(74) *Attorney, Agent, or Firm* — FROST BROWN TODD LLP

(57) ABSTRACT

Certain aspects relate to systems and techniques for an input device for controlling operation of a surgical tool. The input device includes a first set of one or more input objects for receiving an input of a first type associated with the operation of the surgical tool, and a second set of one or more input objects for receiving an input of a second type associated with the operation of the surgical tool. The input device also includes a Hall effect sensor for detecting a magnetic field based on the first set of one or more magnets and the second set of one or more magnets. A medical system including the input device and a method of using the input device for operating a surgical tool are also disclosed.

22 Claims, 46 Drawing Sheets

US 12,575,905 B2
Page 2

(51) Int. Cl.
    *A61B 34/30*         (2016.01)
    *A61B 34/37*         (2016.01)
    *G05G 9/02*         (2006.01)

(52) U.S. Cl.
    CPC ............... *A61B 2017/00039* (2013.01); *A61B 2034/301* (2016.02); *A61B 2034/302* (2016.02); *A61B 2034/303* (2016.02); *A61B 2034/743* (2016.02)

(56) References Cited

U.S. PATENT DOCUMENTS

| | | |
|---|---|---|
| 8,120,301 B2 | 2/2012 | Goldberg et al. |
| 8,182,470 B2 | 5/2012 | Devengenzo et al. |
| 8,398,541 B2 | 3/2013 | Dimaio et al. |
| 8,469,947 B2 | 6/2013 | Devengenzo et al. |
| 8,521,331 B2 | 8/2013 | Itkowitz |
| 8,638,057 B2 | 1/2014 | Goldberg et al. |
| 8,672,922 B2 | 3/2014 | Loh et al. |
| 8,831,782 B2 | 9/2014 | Itkowitz |
| 8,888,764 B2 | 11/2014 | Devengenzo et al. |
| 8,894,634 B2 | 11/2014 | Devengenzo et al. |
| 9,974,620 B2 | 5/2018 | Namiki |
| 10,426,561 B1 | 10/2019 | Kelly et al. |
| 11,135,030 B2 * | 10/2021 | Savall .................... A61B 34/37 |
| 2007/0005002 A1 * | 1/2007 | Millman ................ A61B 34/71 604/30 |
| 2014/0171965 A1 | 6/2014 | Loh et al. |
| 2015/0119637 A1 | 4/2015 | Alvarez |
| 2017/0095298 A1 | 4/2017 | Vakharia et al. |
| 2019/0201047 A1 * | 7/2019 | Yates ................. A61B 18/1445 |
| 2019/0380802 A1 | 12/2019 | Savall et al. |
| 2020/0163731 A1 | 5/2020 | Itkowitz et al. |
| 2020/0205922 A1 | 7/2020 | Cone et al. |
| 2020/0289219 A1 | 9/2020 | Denlinger et al. |

FOREIGN PATENT DOCUMENTS

| | | |
|---|---|---|
| WO | 2019/099504 A1 | 5/2019 |
| WO | 2019240824 A1 | 12/2019 |

OTHER PUBLICATIONS

PCT International Search Report; PCT/IB2021/050796; May 4, 2021; 3 pages.
PCT Written Opinion of the International Searching Authority; PCT/IB2021/050796; May 4, 2021; 5 pages.
European Extended Search Report and Written Opinion dated Mar. 19, 2024, for Application No. 21776880.3, 8 pages.

* cited by examiner

Input Device 286

Sensor(s) 287

Processor(s) 280

Controller 284

Memory 282

290

292-1

292-2

370

310 Detect a magnetic field with a Hall effect sensor. The magnetic field is based on a first set of one or more magnets associated with a first set of one or more input objects and a second set of one or more magnets associated with a second set of one or more input objects.

320 Determine a position of the first set of one or more input objects based on the magnetic field detected by the Hall effect sensor.

330 Determine a position of the second set of one or more input objects based on the magnetic field detected by the Hall effect sensor.

340 The position of the first set of one or more input objects is determined separately from the position of the second set of one or more input objects.

HAND-MANIPULATED INPUT DEVICE WITH HALL EFFECT SENSOR FOR ROBOTIC SYSTEM

CROSS-REFERENCE TO RELATED APPLICATIONS

This application claims the benefit of U.S. Provisional Patent Application Ser. No. 63/000,769, filed Mar. 27, 2020, and is related to U.S. patent application Ser. No. 17/163,972, filed Feb. 1, 2021, issued as U.S. Pat. No. 11,207,147 on Dec. 28, 2021, which are incorporated by reference herein in their entirety.

TECHNICAL FIELD

The systems and methods disclosed herein are directed to input devices, and more particularly, in certain embodiments, to input devices for surgical systems.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotic medical system may be used to control the insertion and/or manipulation of the instrument and end effector. The robotic medical system may include a robotic arm, or other instrument positioning device. The robotic medical system may also include an input device used to control the positioning and/or actuation of the instrument during the procedure.

SUMMARY

The systems, methods and devices of this disclosure each have several innovative aspects, no single one of which is solely responsible for the desirable attributes disclosed herein.

In one aspect, an input device for controlling a robotic surgical tool is provided. The input device can include a first pair of opposing links and a second pair of opposing links. The first pair of opposing links and the second pair of opposing links can be arranged radially symmetrically. The input device can be configured to control operation of the robotic surgical tool.

In some configurations, the first pair of opposing links is longer than the second pair of opposing links. The first pair of opposing links can be of equal length as the second pair of opposing links. Each of the first pair of opposing links can include a finger pad. Each of the second pair of opposing links can include a clutch button. The clutch button can be a push button. The clutch button can include a protruding ledge. The input device can include at least one clutch button. The at least one clutch button, when actuated, can be configured to decouple the input device from controlling operation of the robotic surgical tool. Each of the first pair of opposing links and each of the second pair of opposing links can be coupled to a central longitudinal member. The proximal ends of each of the first pair of opposing links and each of the second pair of opposing links can be configured to radially move relative to the central longitudinal member. Each of the first pair of opposing links can be configured to move together. Each of the second pair of opposing links can be configured to move together. The first pair of opposing links and the second pair of opposing can be are configured to move together. Each of the first pair of opposing links can be configured to move together, such that proximal ends of the first pair of opposing links are positioned equally distant from the central longitudinal member. The first pair of opposing links can be constrained to move together. The second pair of opposing links can be constrained to move together. The central longitudinal member can include a hall effect sensor.

In another aspect, an input device for controlling a robotic surgical tool can be provided. The input device can include a multi-link grasper comprising three or more links coupled to a central longitudinal member. The three or more links can be spaced less than 180 degrees from one another about the central longitudinal member. The multi-link grasper can be configured for controlling operation of the robotic surgical tool. The three or more links can be equally spaced from each other. Each of the three or more links can be configured to move from an open position where proximal ends of each of the three or more links are positioned radially away from the central longitudinal member to a closed position where the proximal ends of each of the three or more links are positioned radially close to the central longitudinal member. Each of the three or more links can be biased in the open position.

In yet another aspect, an input device for controlling a surgical tool can be provided. The input device can include a multi-link grasper comprising two or more links about a central longitudinal member for controlling operation of the surgical tool.

In some configurations, the at least one of the two or more links can include a finger input. The finger input can be capable of operating in a first mode and in a second mode. In the first mode, the finger input can operate as a finger clutch and, in the second mode, the finger clutch operates as a selecting tool. The finger input can include a push input. The finger input can include a rotary input. The central longitudinal member can include a sensor for detecting a mode of the finger input. The sensor can be coupled to the central longitudinal member. Each of the two or more links can include a curved face at a proximal end. The curved face can wrap around the central longitudinal member. The input device can include a rack gear. The rack gear can include gear teeth configured to mate with each of the two or more links. Each of the two or more links can be configured to rotate relative to the rack gear, wherein each of the two or more links are configured to engage with the rack gear such that rotation of one of the two or more links causes rotation of remaining links of the two or more links. Each of the two or more links can include bevel gear teeth configured to connect motion of each of the two or more links to the remainder of the two or more links.

In yet another aspect, a physician console can be provided. The physician console can include an input device including a first grasper and a second grasper. The input device can be configured to control a surgical tool. At least one of the first and second grasper can include a four-link radially symmetrical grasper for controlling operation of the surgical tool.

In accordance with some embodiments, an input device for controlling operation of a surgical tool is provided. The input device includes a first set of one or more input objects for receiving an input of a first type associated with the operation of the surgical tool, and a second set of one or more input objects for receiving an input of a second type associated with the operation of the surgical tool. The second set of one or more input objects is distinct from the first set of one or more input objects object. The input device also includes a first Hall effect sensor for detecting a magnetic field based on the first set of one or more magnets and the second set of one or more magnets.

In accordance with some embodiments, a medical system includes a surgical tool and an input device for operating the surgical tool. The input device includes a first set of one or more input objects for receiving an input of a first type associated with the operation of the surgical tool, and a second set of one or more input objects for receiving an input of a second type associated with the operation of the surgical tool. The second set of one or more input objects is distinct from the first set of one or more input objects object. The input device also includes a first Hall effect sensor for detecting a magnetic field based on the first set of one or more magnets and the second set of one or more magnets.

In accordance with some embodiments, a method for operation a surgical tool is performed by one or more processors executing instructions store in memory. The method includes detecting a magnetic field with a Hall effect sensor. The magnetic field is based on a first set of one or more magnets associated with a first set of one or more input objects and a second set of one or more magnets associated with a second set of one or more input objects. The method also includes determining a position of the first set of one or more input objects based on the magnetic field detected by the Hall effect sensor and determining a position of the second set of one or more input objects based on the magnetic field detected by the Hall effect sensor.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 37 is a flowchart illustrating a method for operating a surgical tool via the input device of FIG. 34A.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
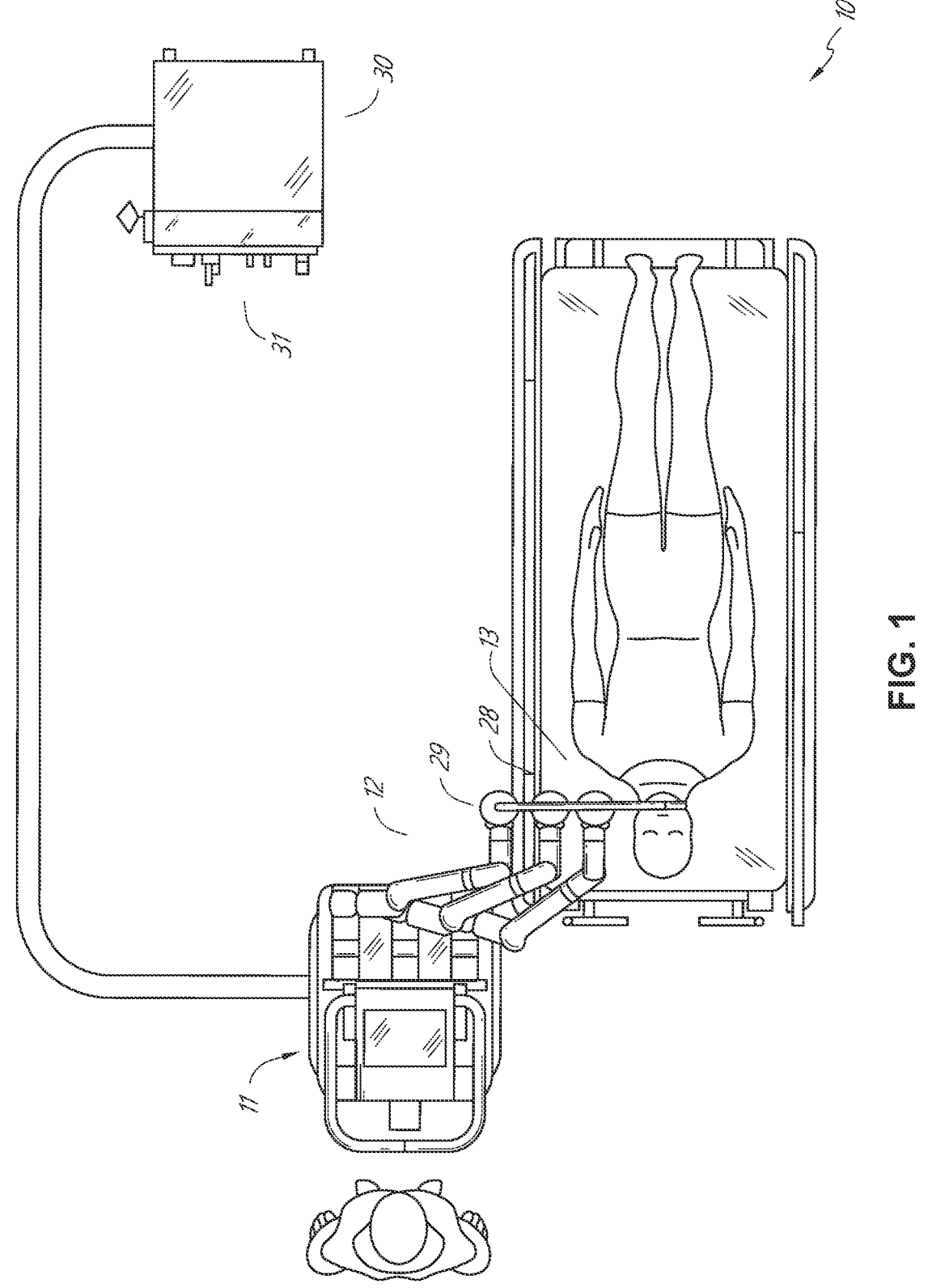
FIG. 1 illustrates an embodiment of a cart-based robotic system arranged for diagnostic and/or therapeutic bronchoscopy.
Figure 2:
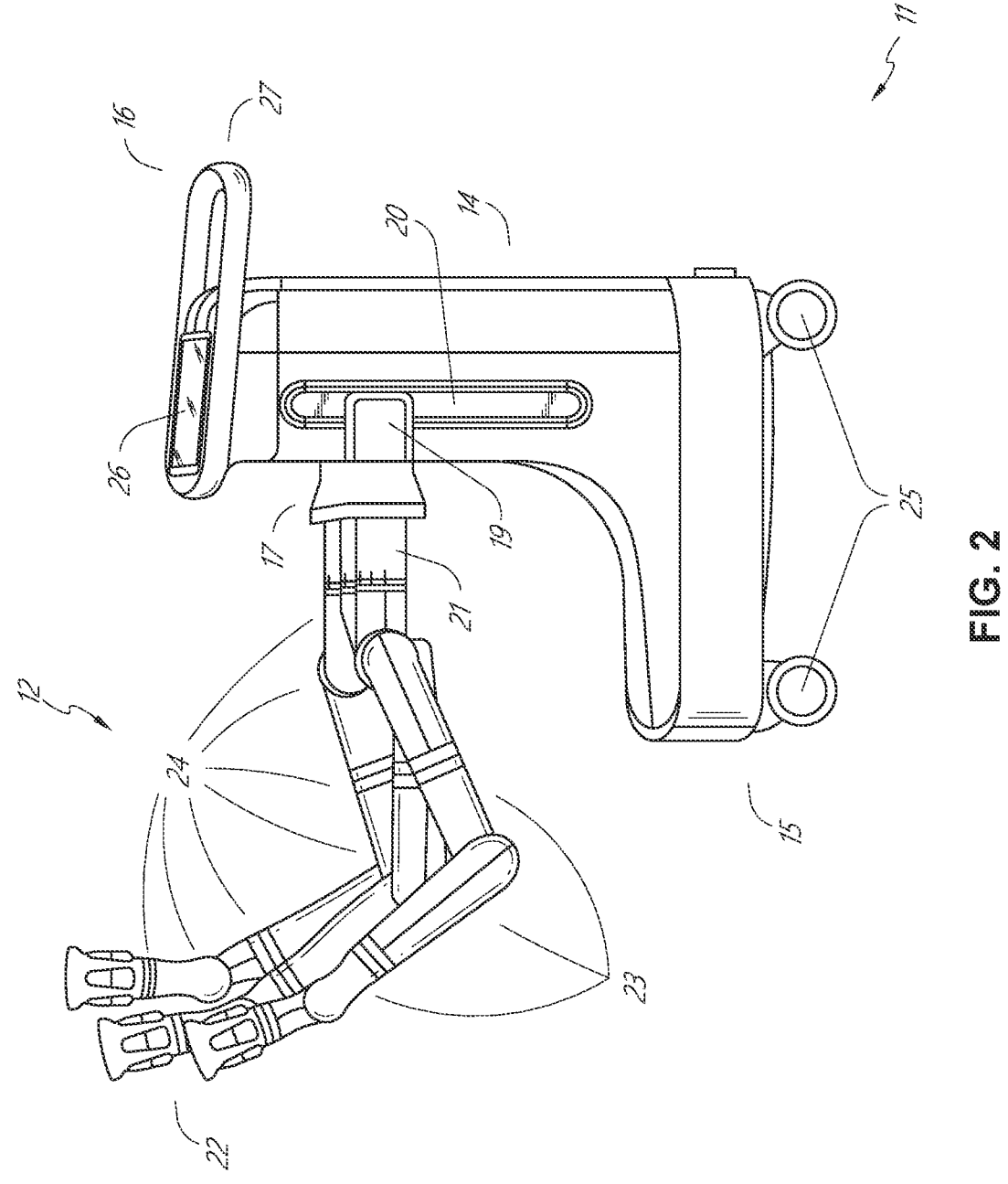
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include pre-operative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
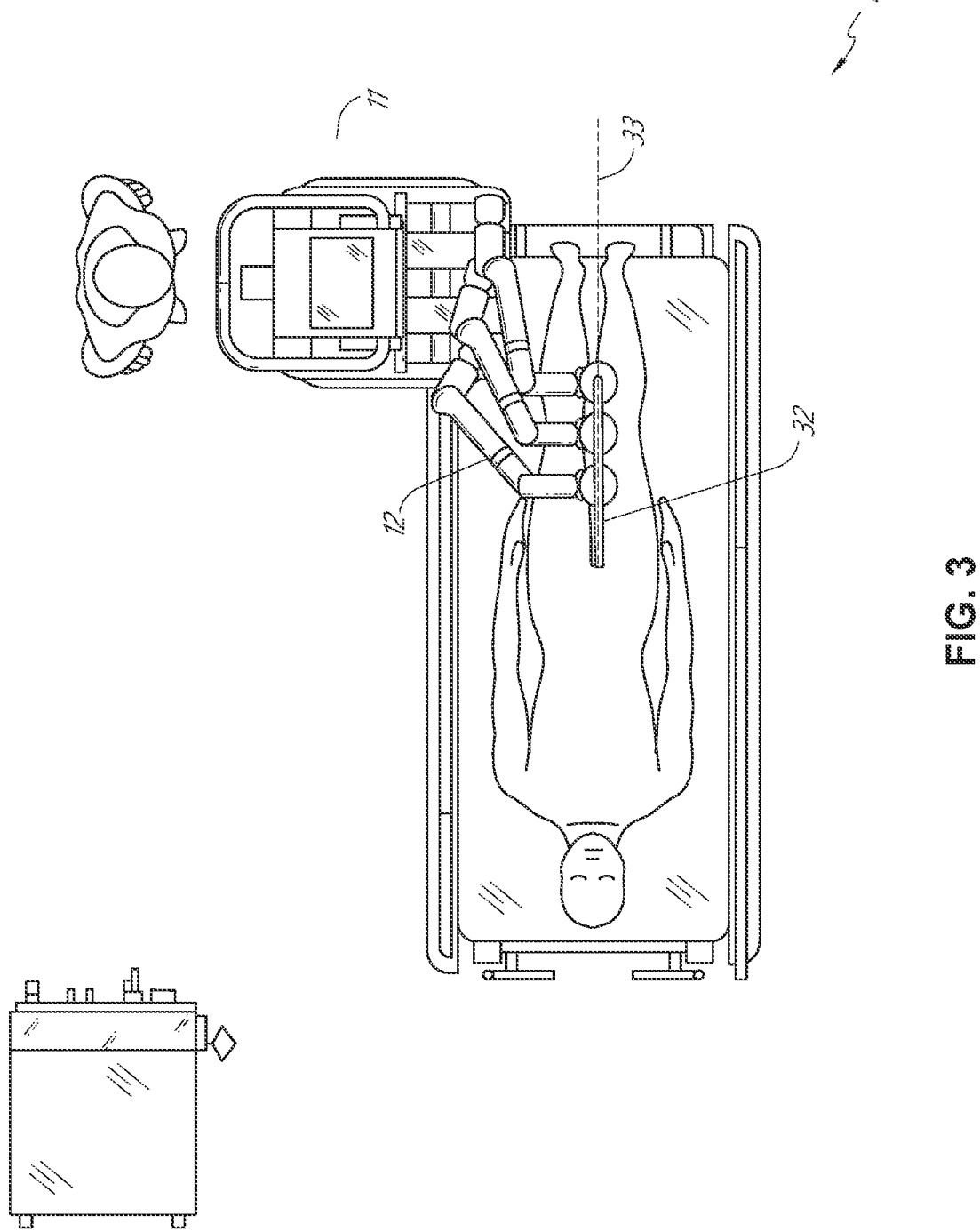
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
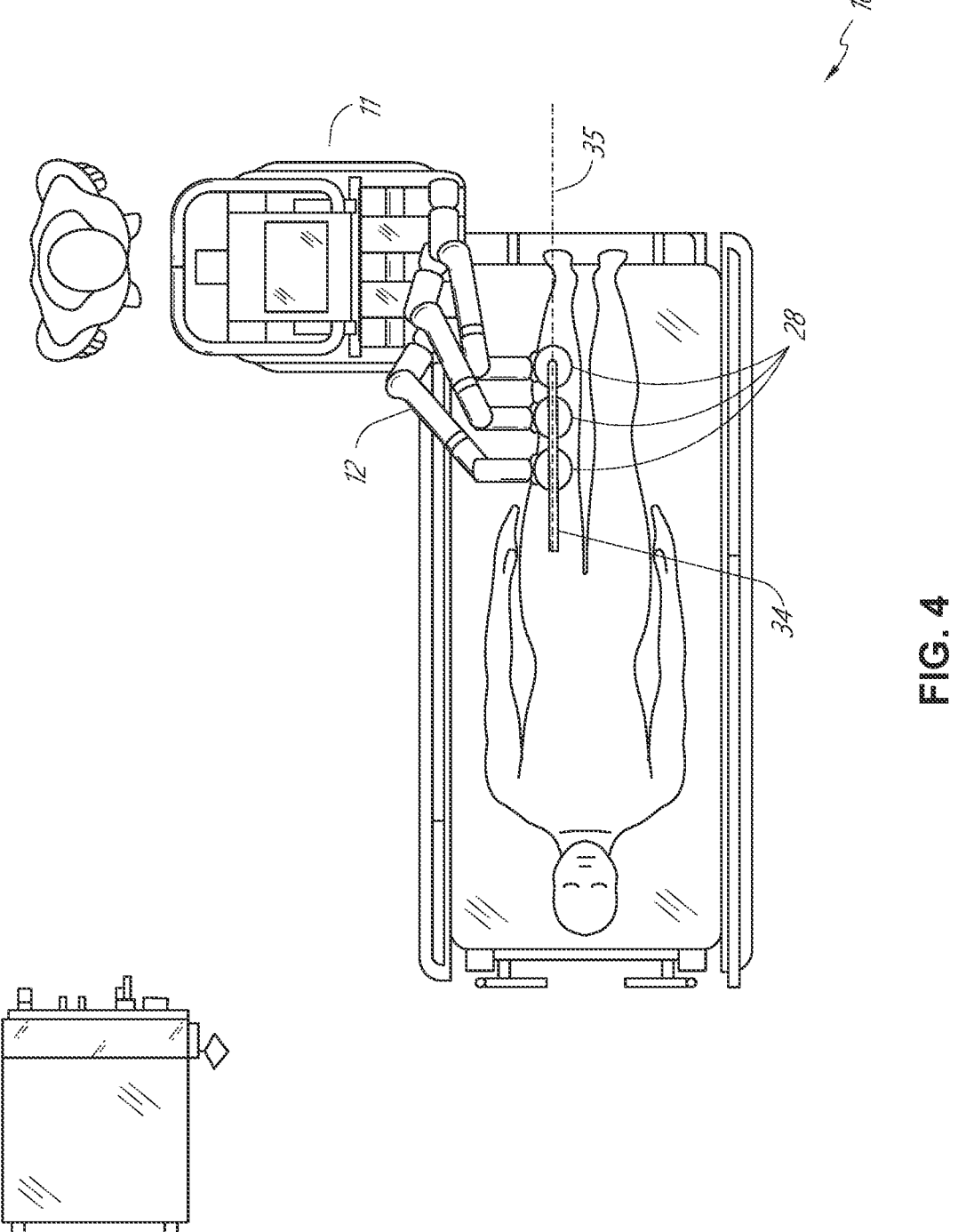
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
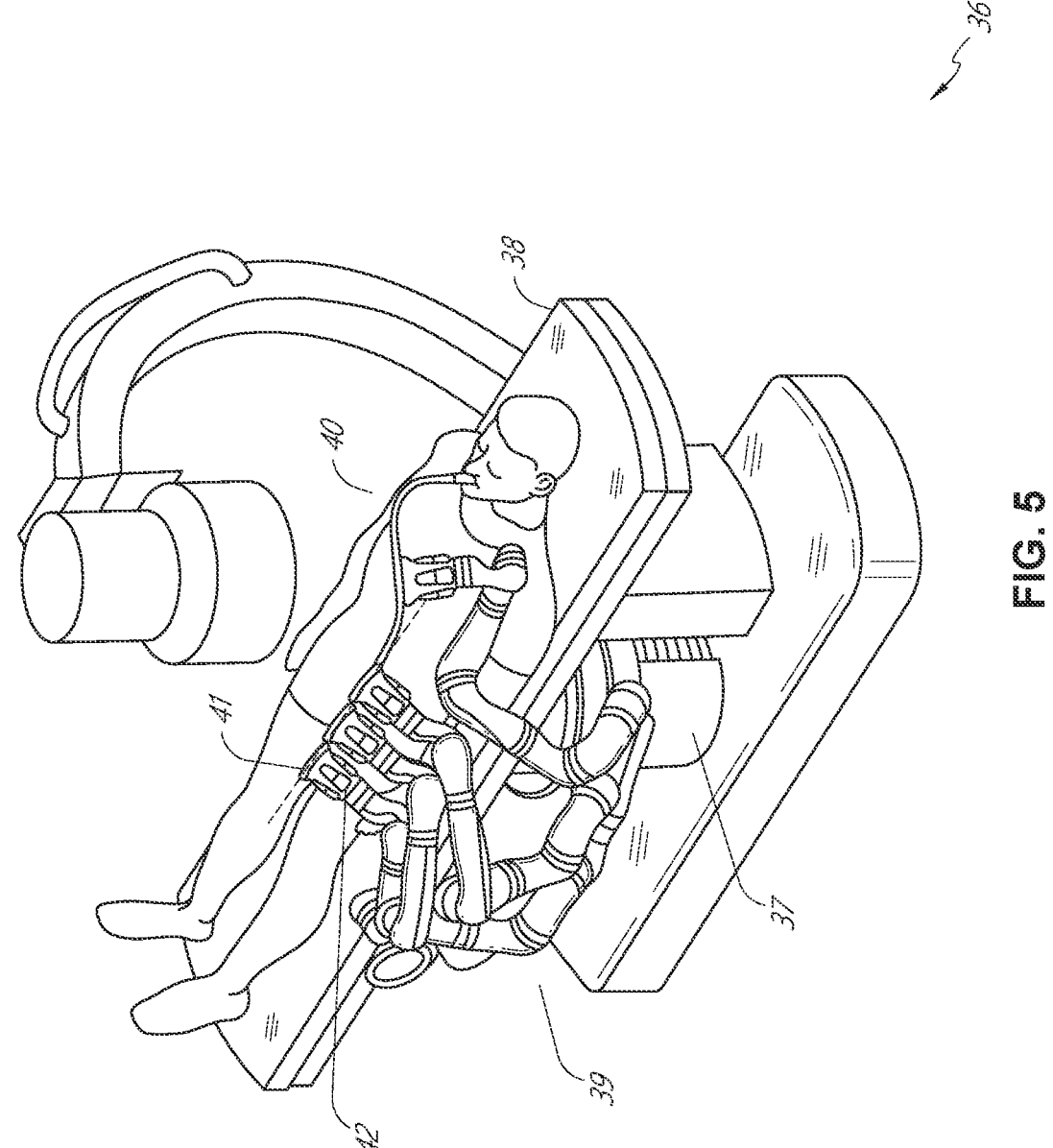
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a broncho-scopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a broncho-scope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
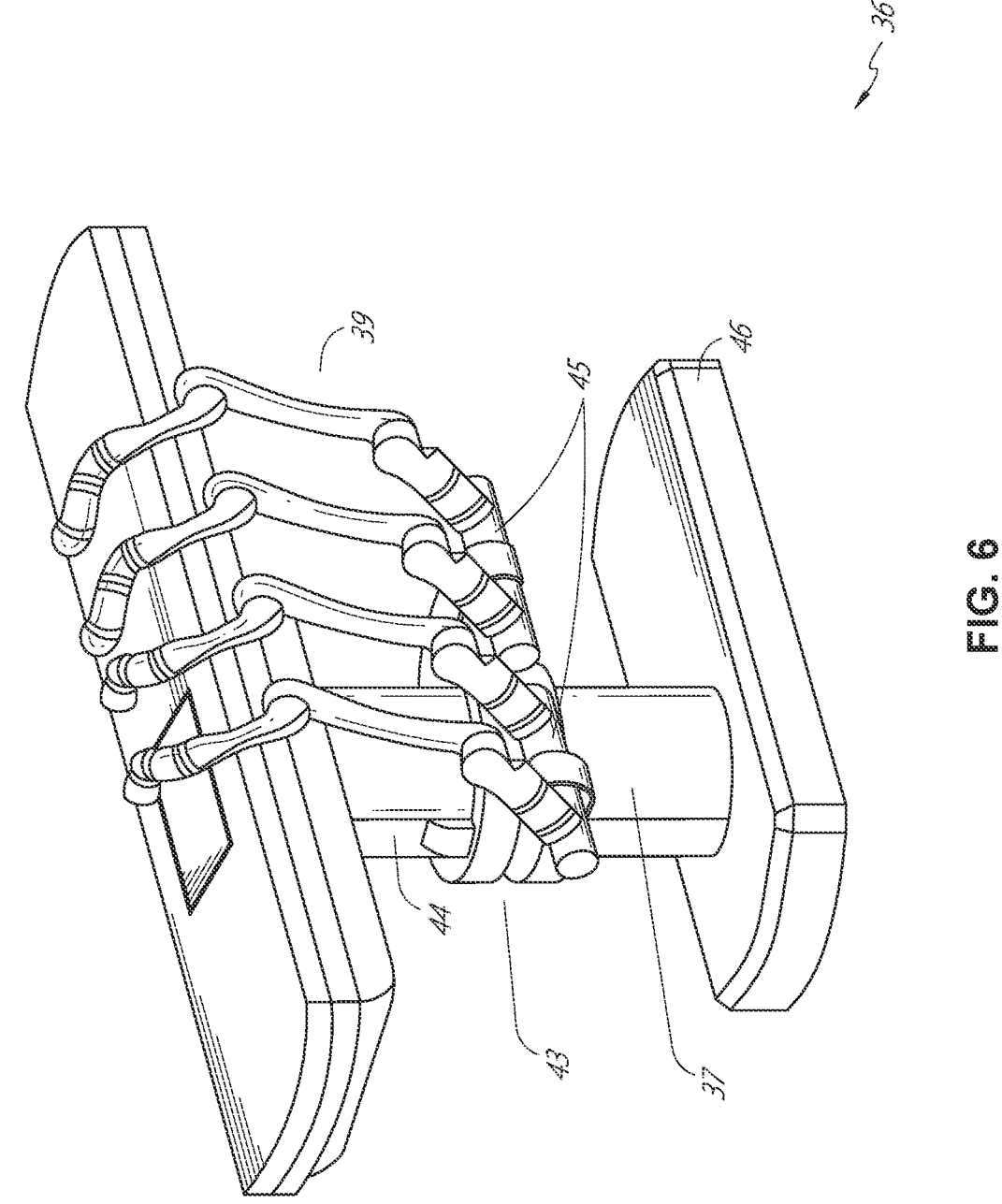
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
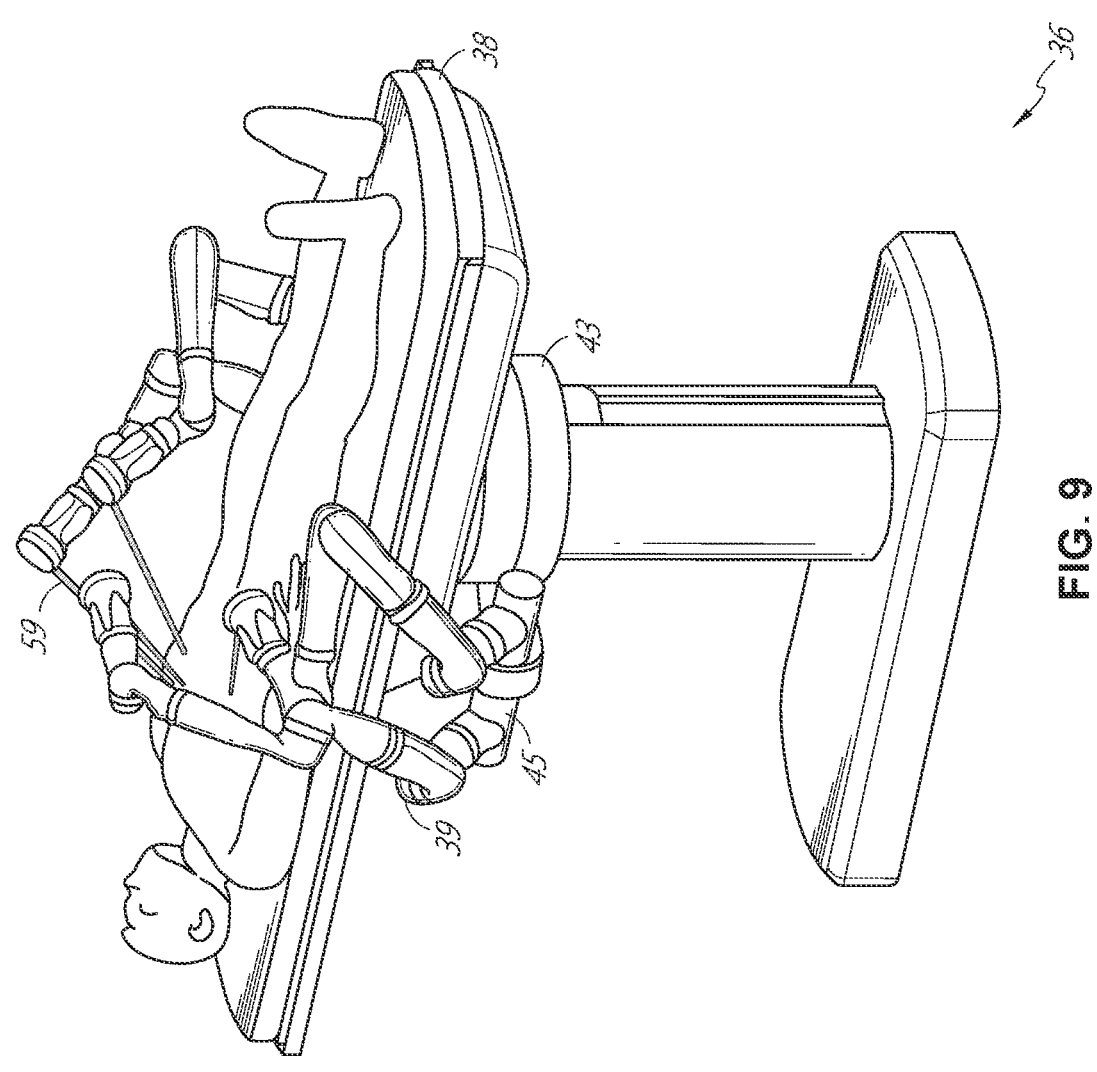
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
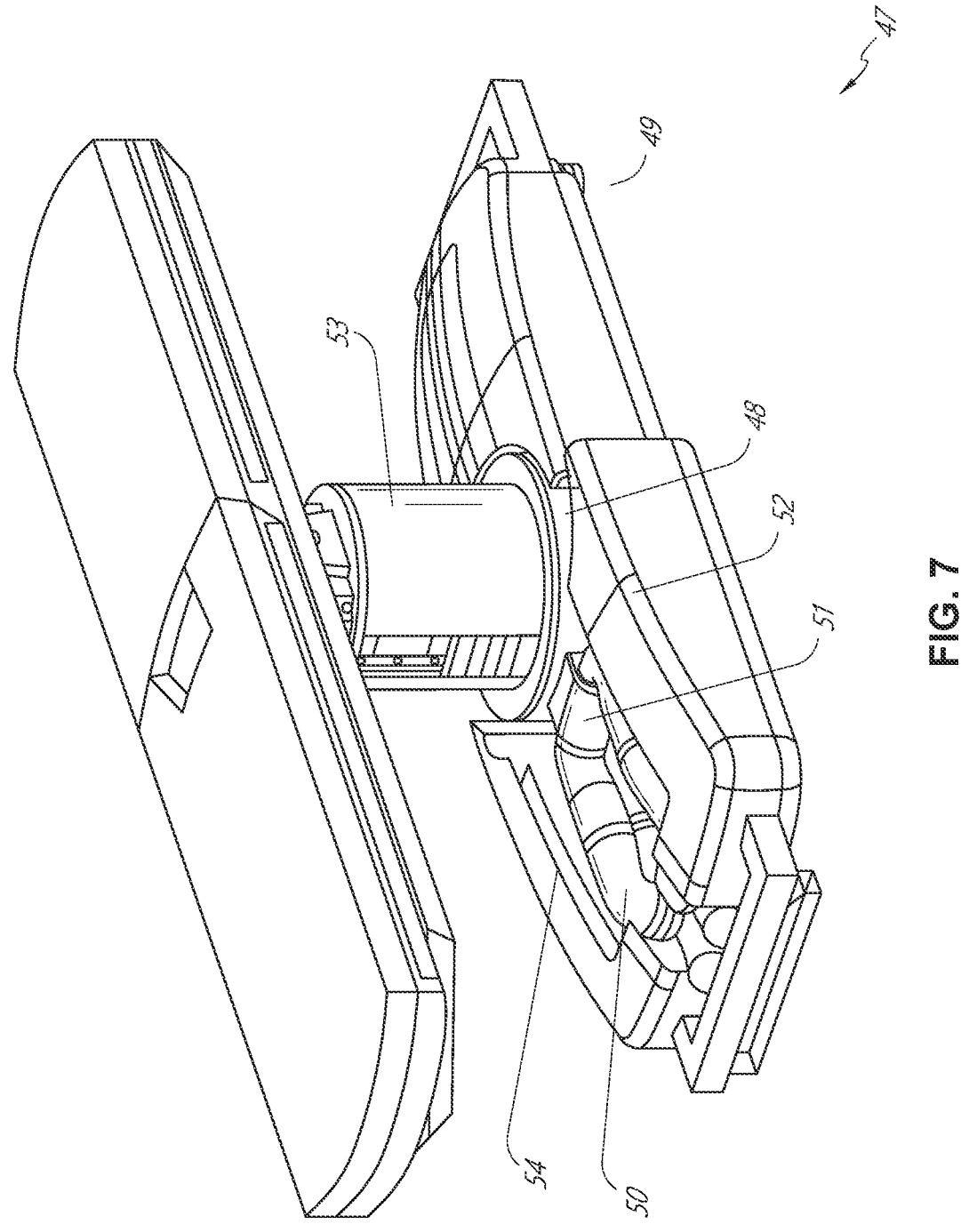
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
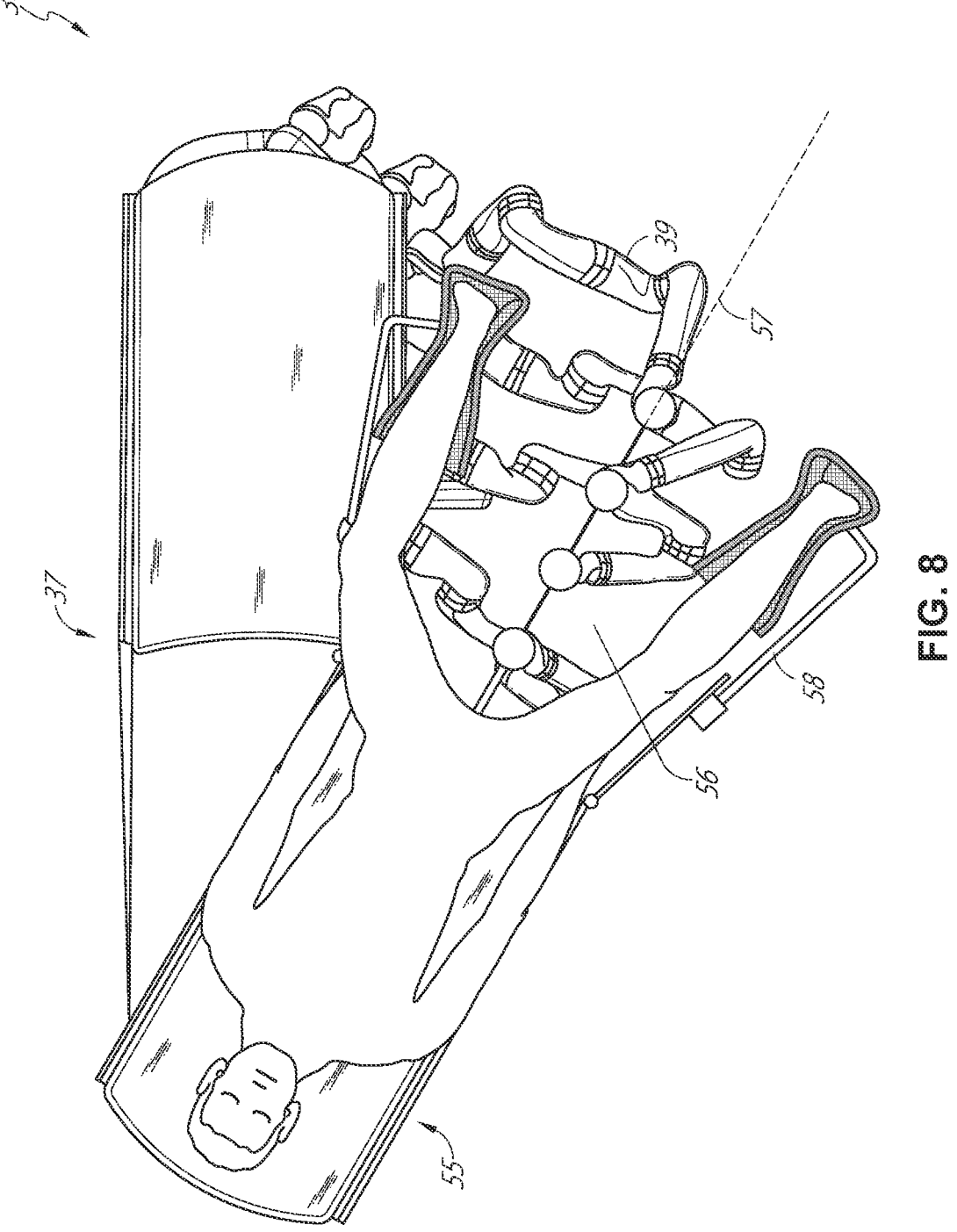
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope.

FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
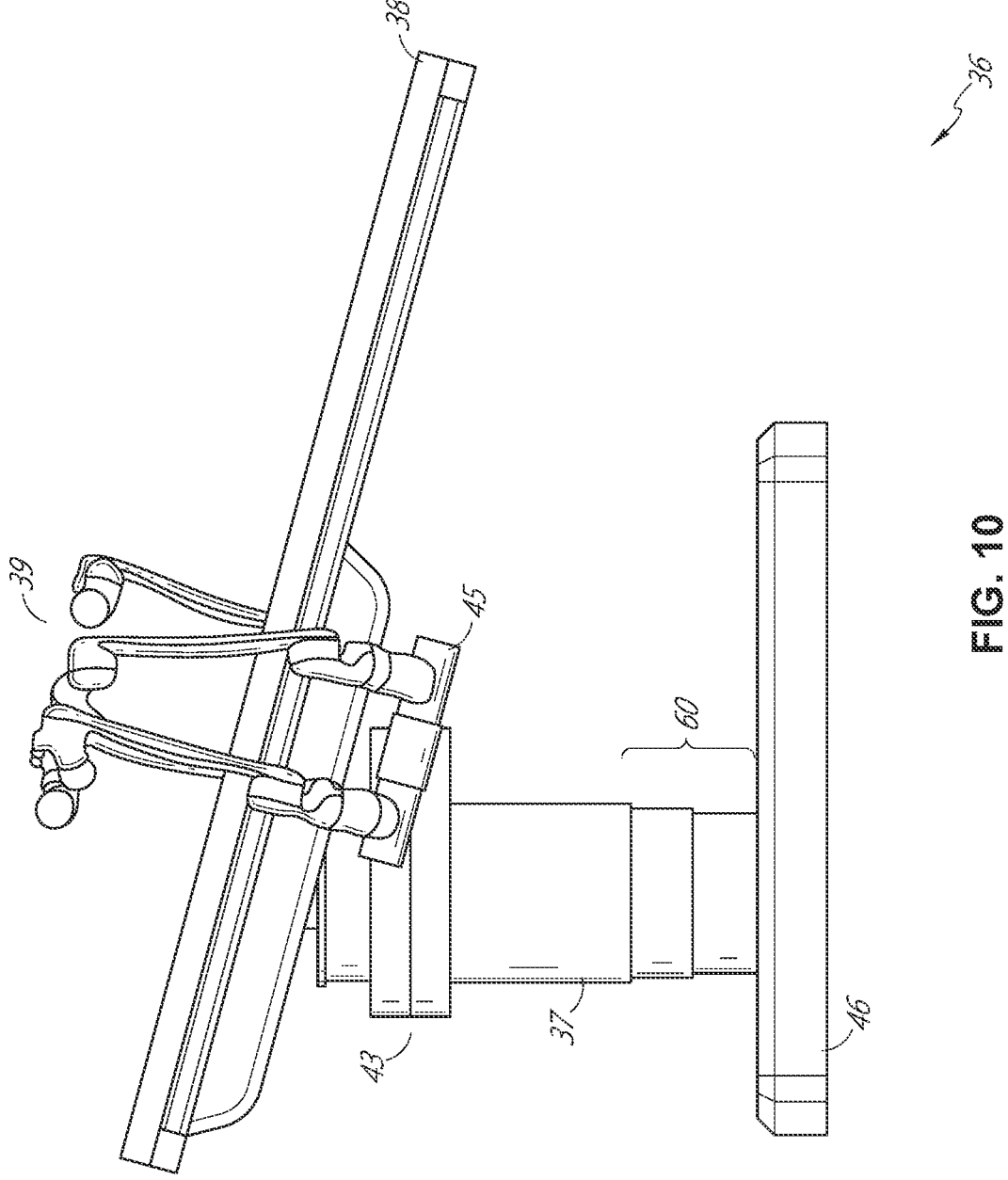
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
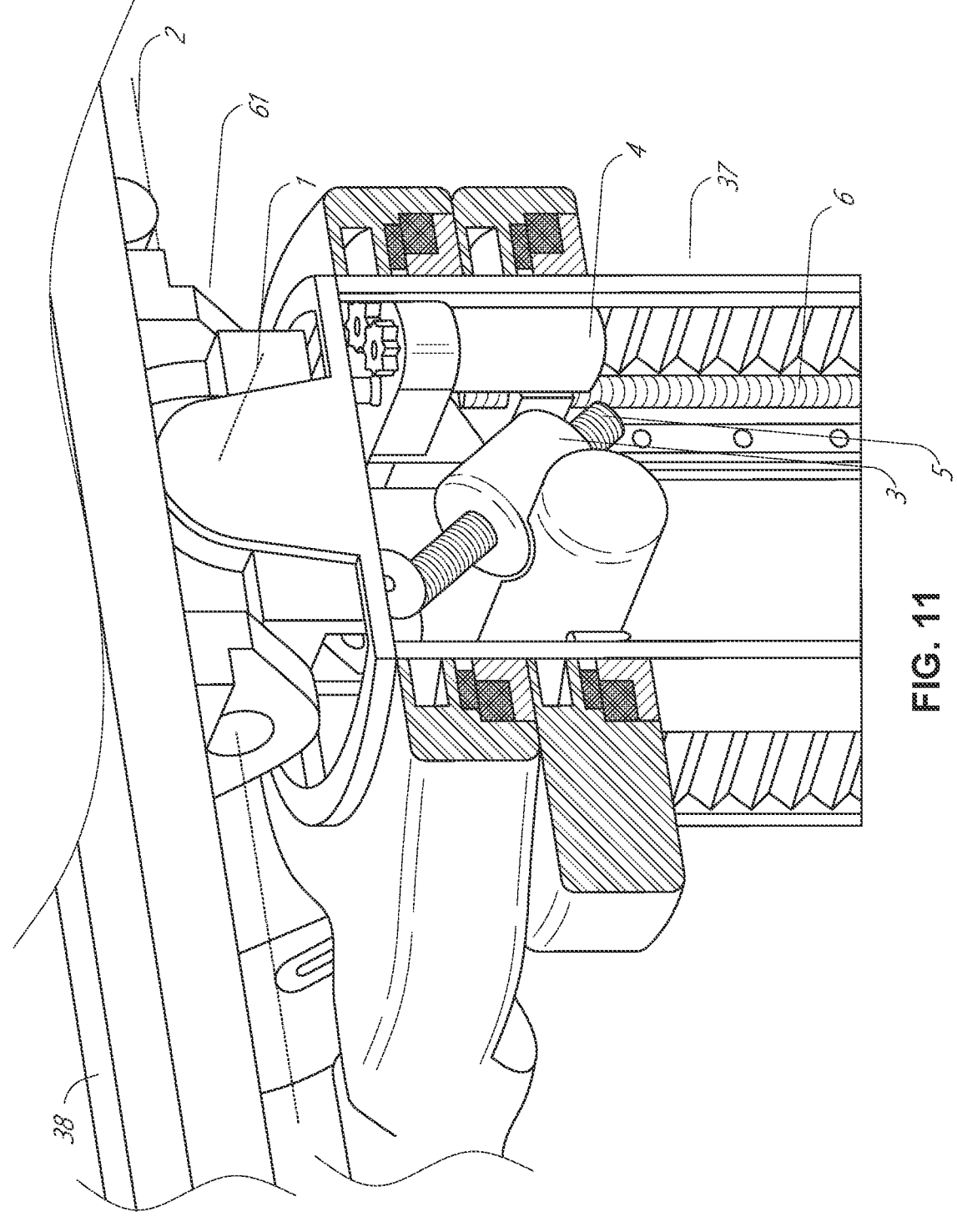
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
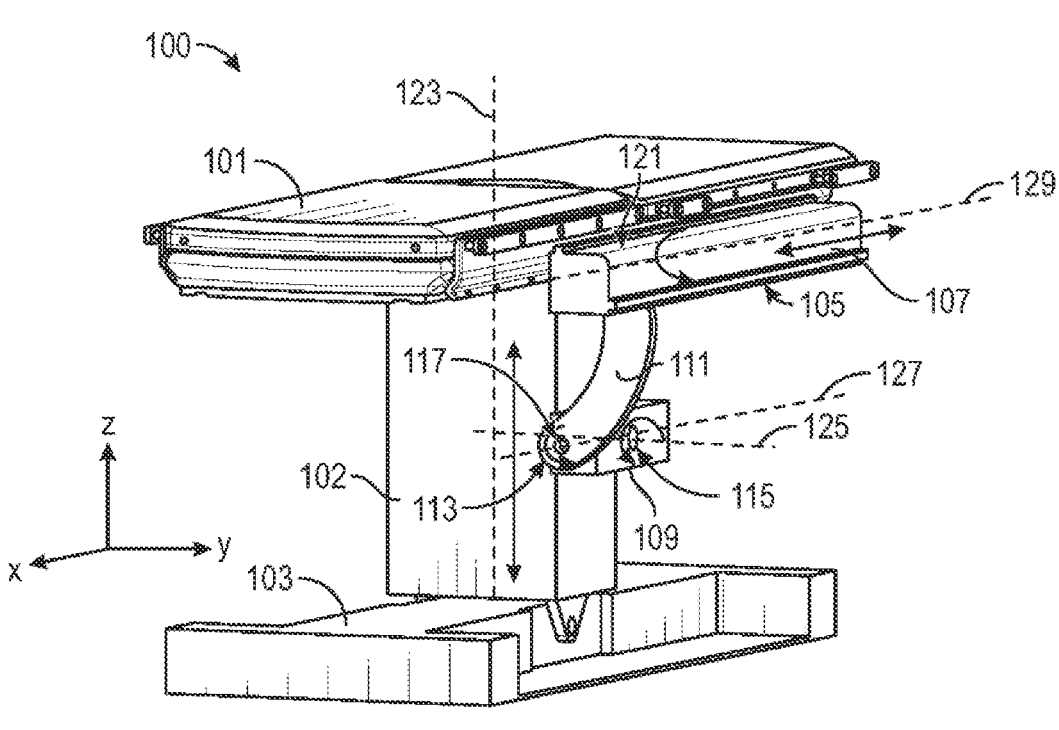
FIG. 12 illustrates an alternative embodiment of a table-based robotic system.
Figure 13:
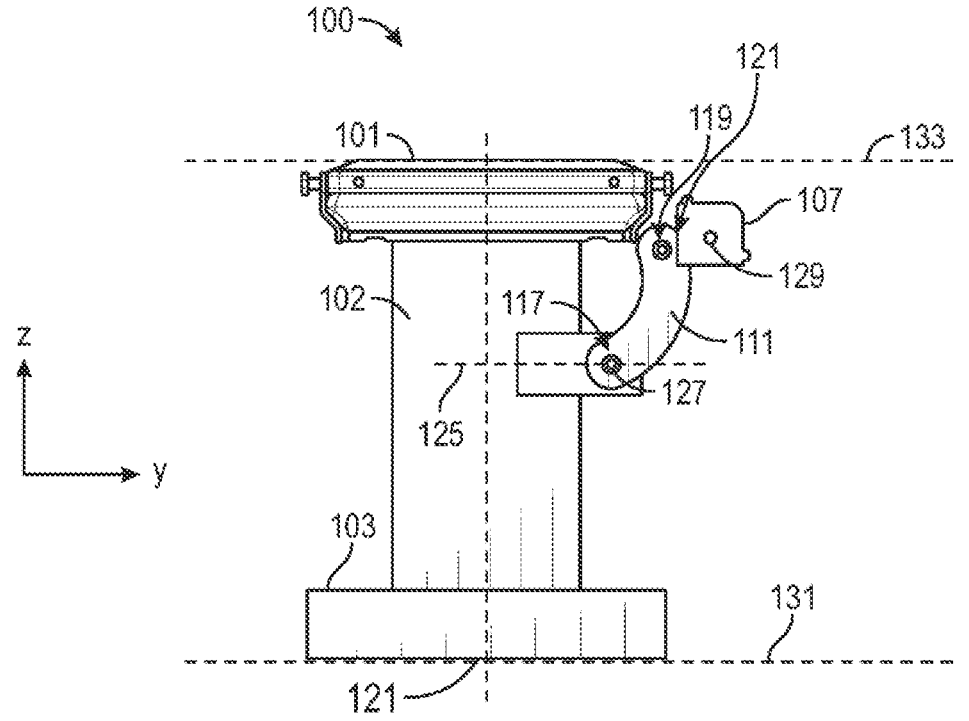
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
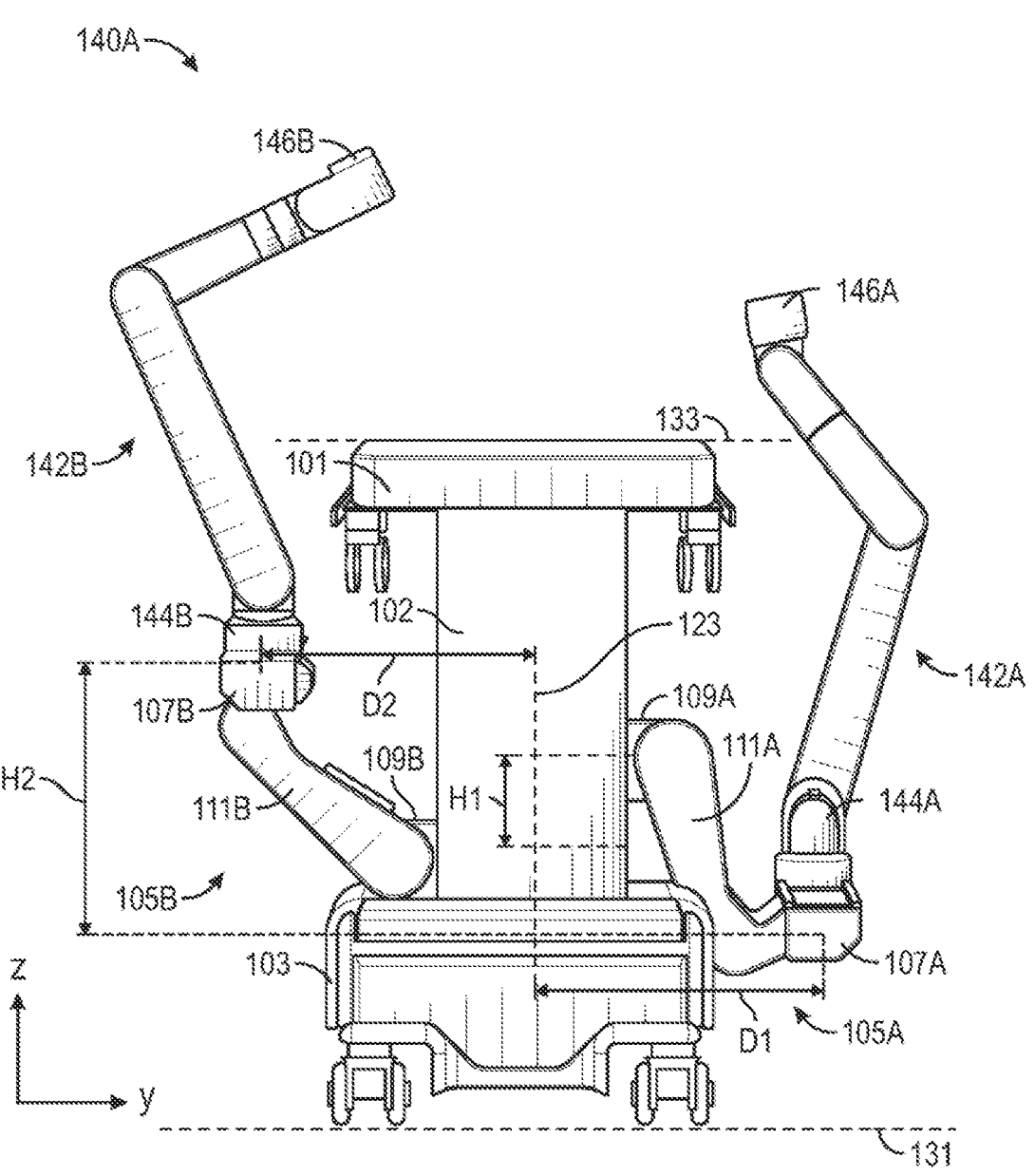
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
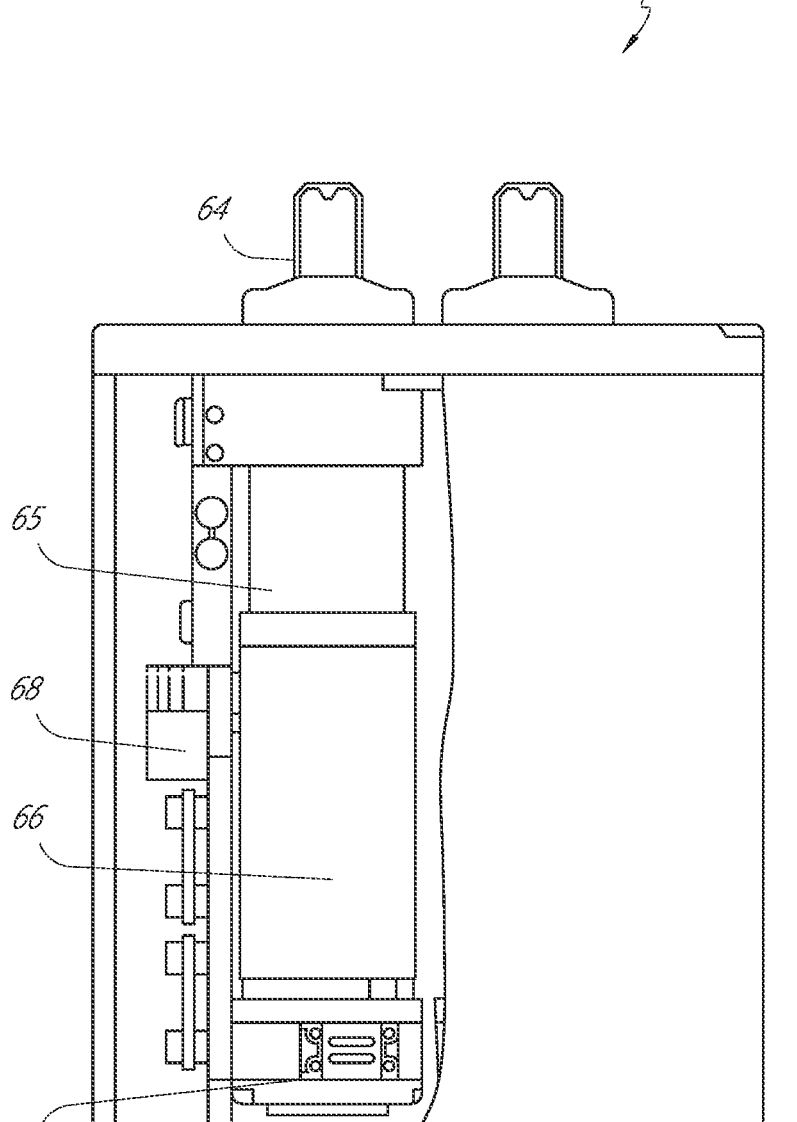
FIG. 15 illustrates an exemplary instrument driver.
Figure 15:

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
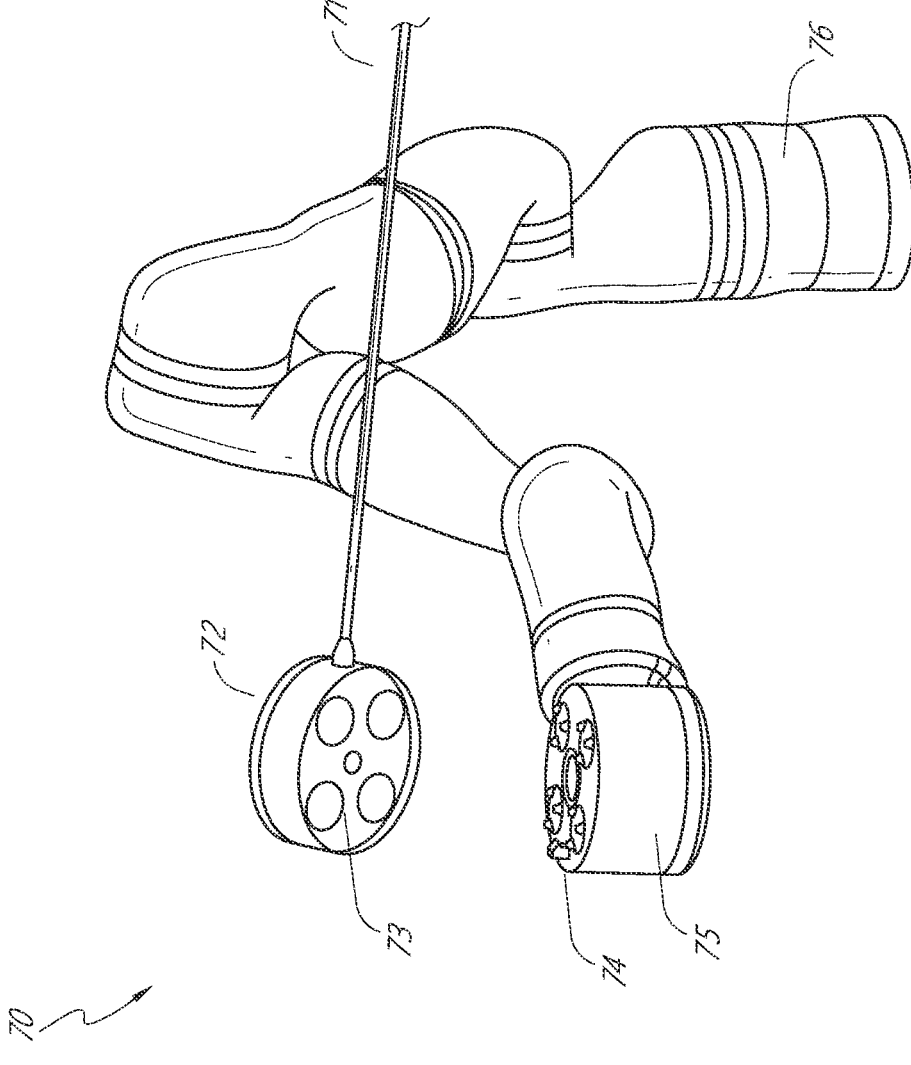
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
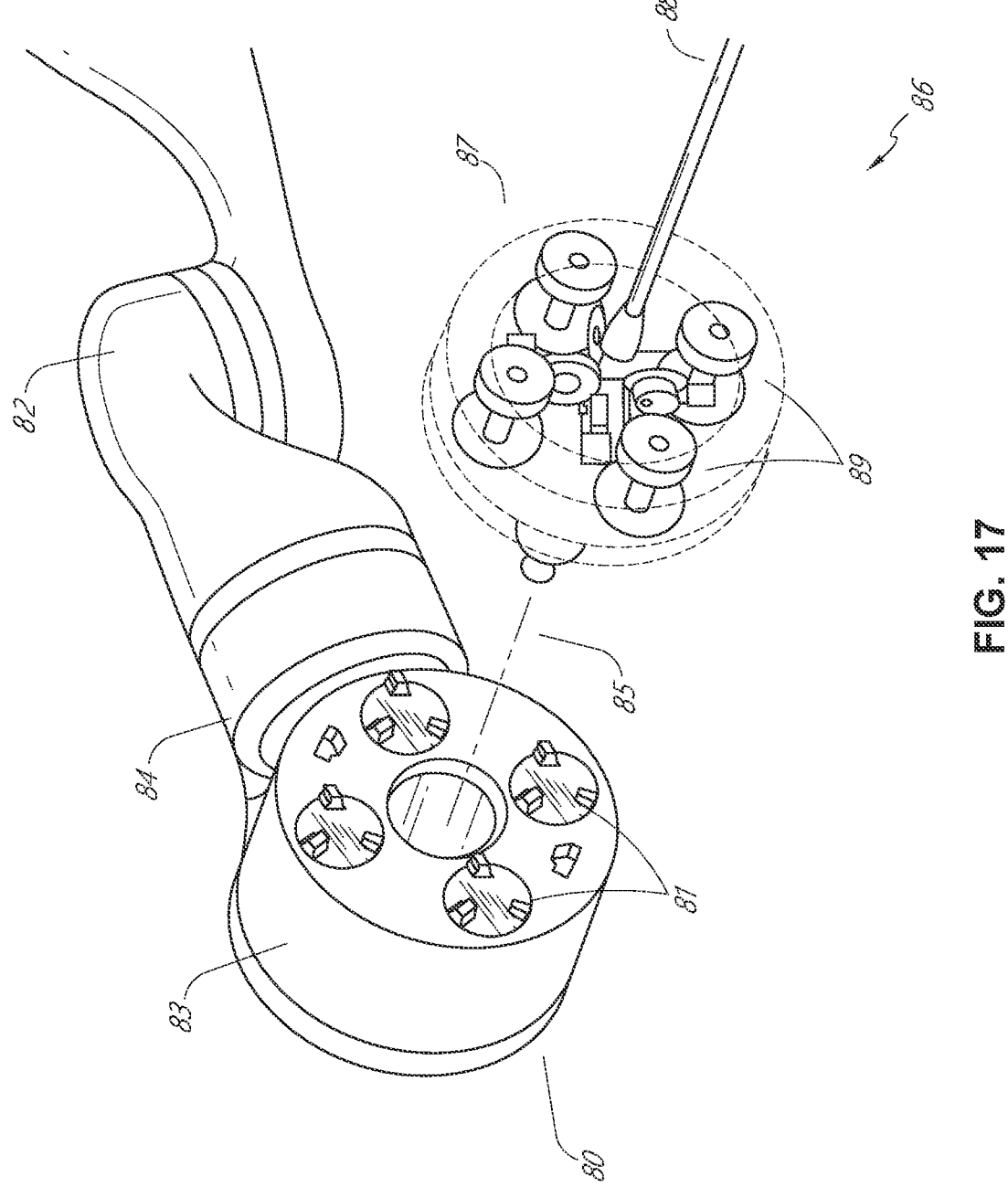
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the nonrotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
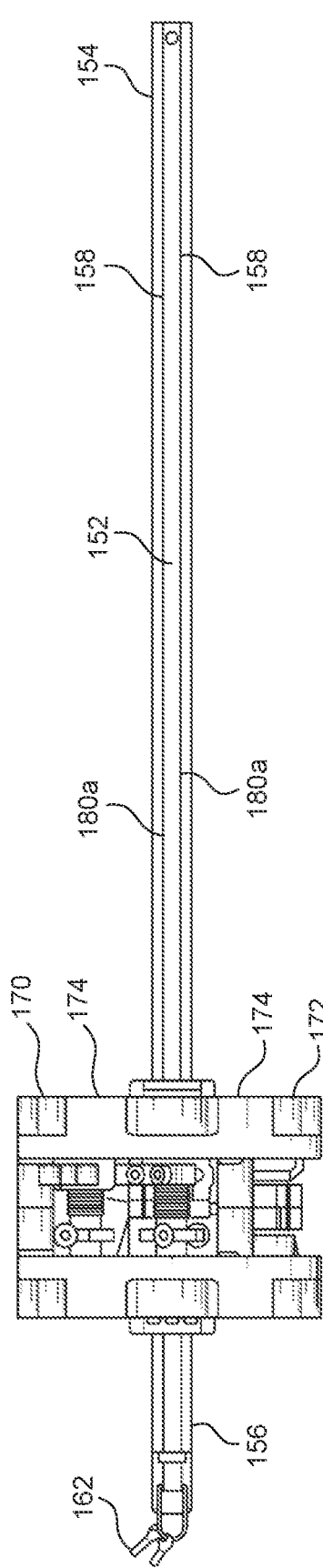
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
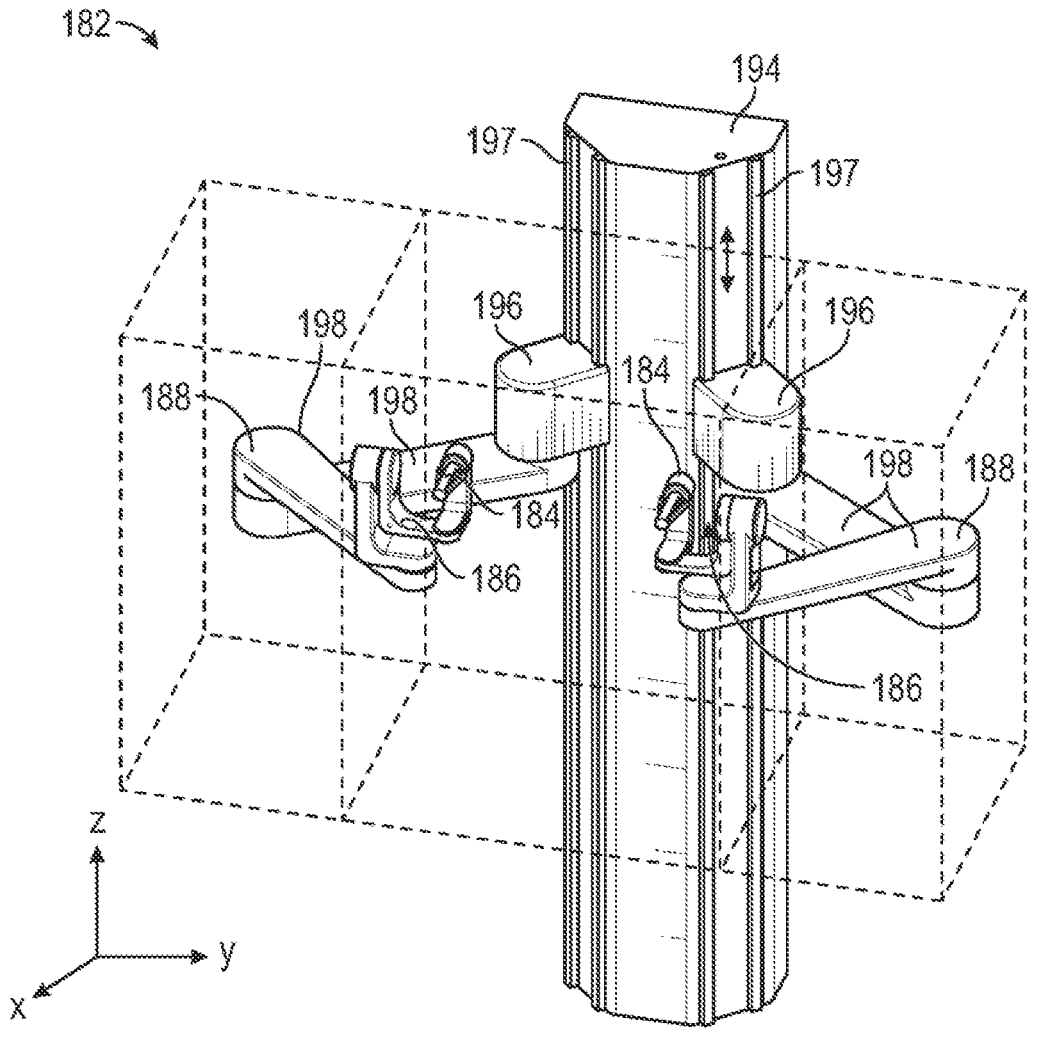
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
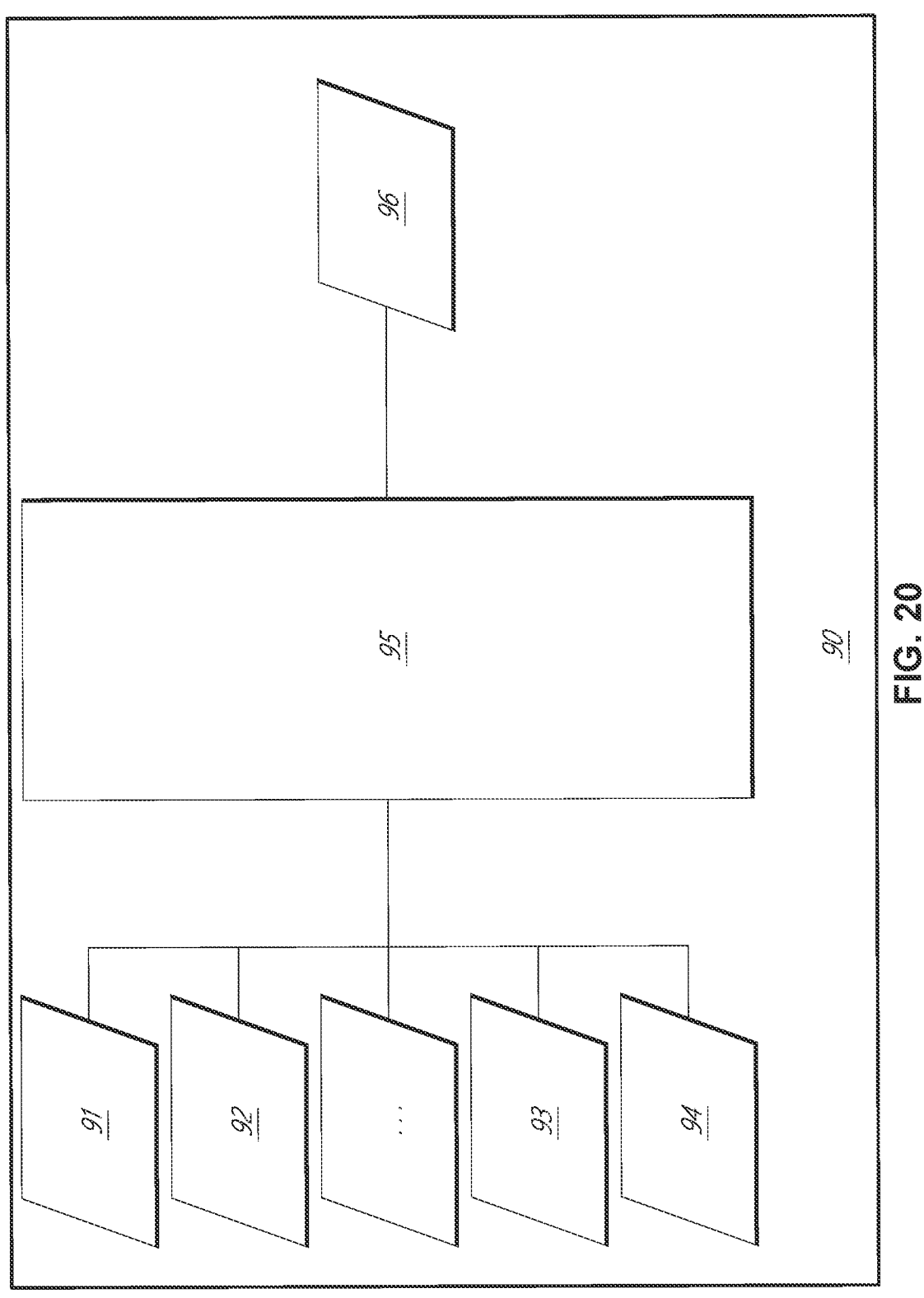
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, which issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Hand Manipulated Input Devices for Robotic Systems

Embodiments of the disclosure relate to systems and techniques for input devices for operating one or more medical instruments.

Robotic medical systems, such as the systems described above, can include an input device that is configured to allow an operator (e.g., a physician performing a robotically-enabled medical procedure) to manipulate and control one or more instruments. In some embodiments, the robotic medical system can include an input device for operating one or more medical tools. In some examples, the input device can operate one or more medical tools remotely, such as via teleoperation or telesurgery.

One skilled in the art will appreciate that the input devices described herein can be applied in non-medical contexts as well. For example, the input devices can be useful for manipulating tools that involve hazardous substances. In addition, in some embodiments, the input devices described herein can be useful in grabbing objects in both physical and virtual environments. In some configurations, the input devices can be self-sufficient as service robots interacting with human operators. In some configurations, the input device can be coupled (e.g., communicatively, electronically, electrically, wirelessly and/or mechanically) with a medical instrument such that manipulation of the input device causes a corresponding manipulation of the medical instrument. In some configurations, the input device and the medical instrument are arranged in a master-slave pair. In some configurations, the input device can be configured to control operation of a robotic surgical tool. In some configurations, the input device can be referred to as a manipulator, emulator, master, controller, interface, etc.

The input device can serve as an input for an operator to control the actions of a medical instrument, such as in an endoscopic, endoluminal, laparoscopic, or open surgery. Movement of the input device by the operator can direct the movement of the medical instrument. For example, when an operator translates the input device in three-dimensional space (e.g., up, down, left, right, backwards, forwards), the system can cause a corresponding translation of the medical instrument. Similarly, if the operator rotates the input device (e.g., around any of three orthogonal axes) the system can cause a corresponding rotational movement of the medical instrument. The input device can also include one or more inputs that allow the operator to actuate the medical instrument. As one example, if the medical instrument includes a grasper instrument, the input device can include one or more inputs that allow the operator to open and close the grasper instrument.

In some embodiments, robotic medical systems include input devices with seven degrees of freedom that follow the operator's hand movement, with the seven degrees of freedom including three positional degrees of freedom (e.g., translational movement in x, y, z space), three rotational degrees of freedom (e.g., rotational movement around pitch, roll, and yaw axes), and one (or more) instrument actuation degree of freedom (e.g., an angular degree of freedom). In some embodiments, the instrument actuation degree of freedom can control the opening and closing of an end effector of the medical instrument, such as a gripper or grasper instrument to hold an object. In some embodiments, input devices can include greater or fewer numbers of degrees of freedom. For example, in some embodiments, the input device can include more than three positional degrees of freedom or more than three rotational degrees of freedom to provide one or more redundant degrees of freedom. In some embodiments, redundant degrees of freedom can provide additional mechanical flexibility for the input device, for example, to avoid singularities caused by the mechanical structure of the input device.

FIG. 19 shows an embodiment of an input device or controller 182 that can be used by a user to control one or more instruments. As noted above, the controller can include two handles 184 that can be used to control instrumentation. Each of the handles 184 can be connected to a gimbal 186. Both of the handles 184 can serve as a grasper.

The grasper can be the portion of the input device that the physician touches and holds to allow the user to control the components of the robotic system, such as the medical instruments. The grasper can be the physician's primary input into the system during surgery. When using a grasper, a user can encounter a number of challenges. In some instances, the grasper is not always comfortable to use. For example, when executing a roll maneuver, it can be difficult for a user to hold onto the various components of the grasper, such as opposing finger grips. Users can choose to work outside of the finger grips to perform such a maneuver, whereby they grip the links of the grasper at a point distal to the finger pads. When moving their hand to such a position, it can be difficult to access other components of the grasper, such as secondary controls or the finger clutch. Therefore, there is a need for ergonomic features to allow a physician to maneuver the grasper as desired.

A. Multi-Link Grasper

Figure 21A:
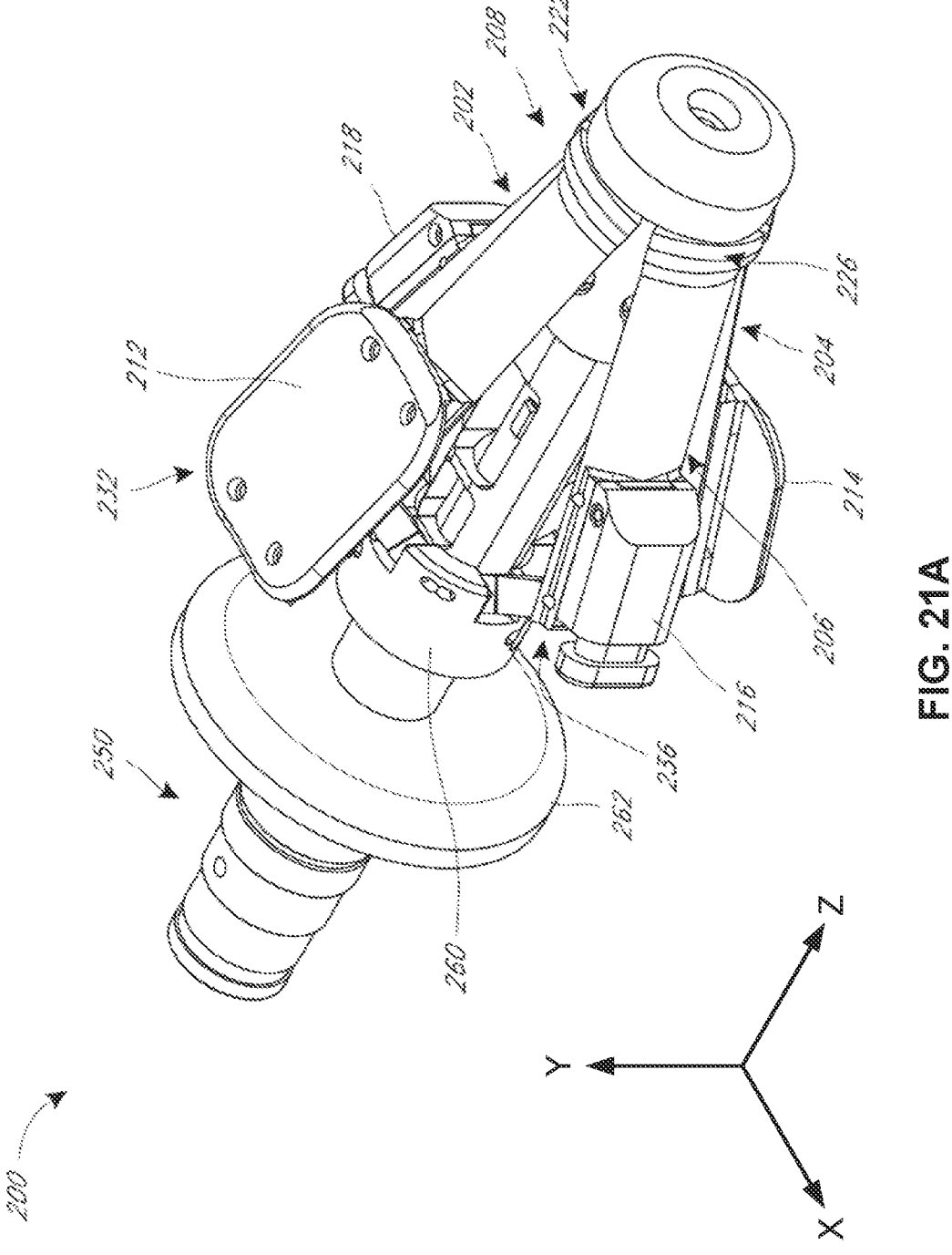
FIG. 21A illustrates an input device in an open position.
Figure 21B:
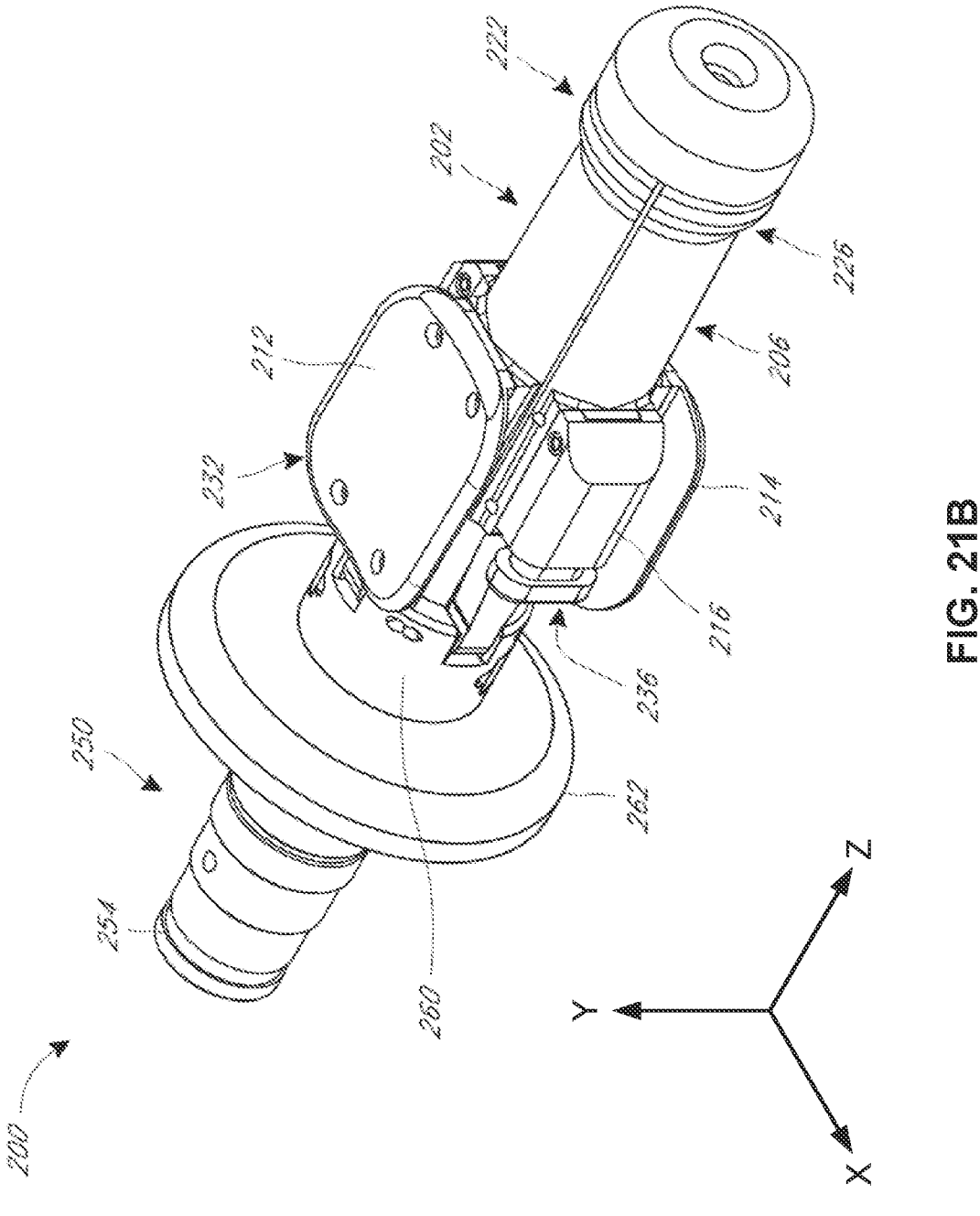
FIG. 21B illustrates the input device of FIG. 21A in a closed position.
Figure 22:
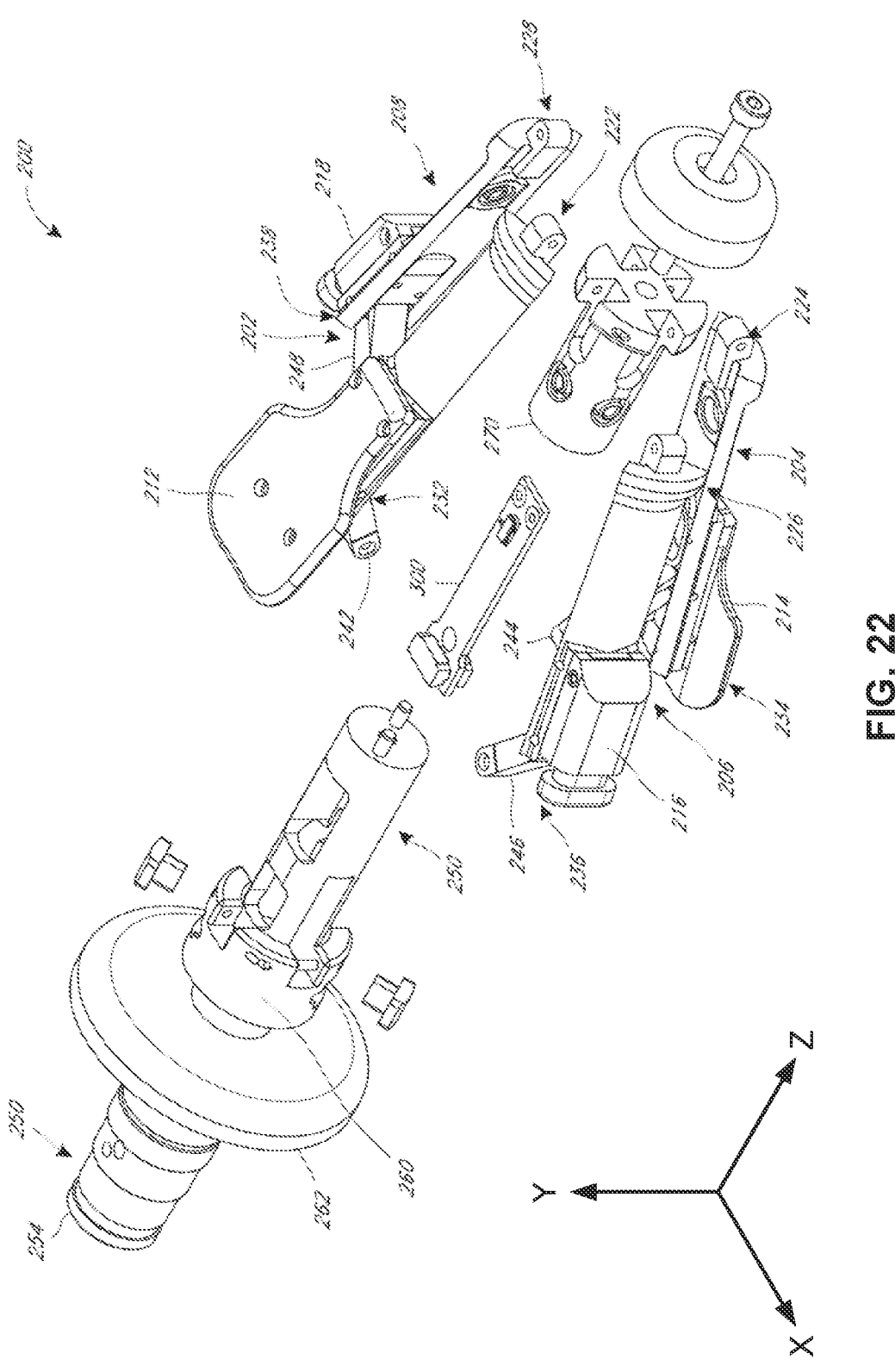
FIG. 22 illustrates the input device of FIGS. 21A-21B in an exploded view.

FIGS. 21A-21B illustrate an embodiment of a handle or grasper 200 that can be used in as part of a input system such as the input system described above with reference to FIG. 19. FIG. 21A illustrates the grasper 200 in an open configuration while FIG. 21B illustrates the grasper 200 in a closed configuration. FIG. 22 illustrates the grasper of FIGS. 21A-21B in an exploded view. The grasper 200 can include a plurality of links and in the illustrated embodiment the grasper 200 includes four links 202, 204, 206, 208. In some configurations, the grasper can include at least two links. In some configurations, the grasper 200 can include at least three links. In some examples, the grasper 200 can have any number of links, such as anywhere between 2-12 links. In some embodiments, the plurality of links can be arranged circumferentially around the grasper 200. In some configurations, the plurality of links can be equally spaced from one another. In some configurations, the plurality of links can be spaced less than 180 degrees from one another about a central axis. Although the configurations described below include four links, any number of links can be included.

As illustrated in FIGS. 21A-21B, the grasper 200 includes four links comprising a first link 202, a second link 204, a third link 206, and a fourth link 208. The four links 202, 204, 206, 208 are spaced at least less than 180 degrees from one another and about the circumference of the grasper 200. The four links 202, 204, 206, 208 can be spaced evenly from each other. The four links can be arranged radially symmetrically. The four links 202, 204, 206, 208 can each be spaced less than 180 degrees from the adjacent links. The four links 202, 204, 206, 208 may be each spaced approximately 90 degrees from one another as shown in the illustrated arrangement. The plurality of links 202, 204, 206, 208 can be arranged circumferentially about the grasper 200 as illustrated.

The links 202, 204, 206, 208 can be arranged in pairs. For example, the grasper 200 can include a first pair of opposing links 202, 204 and a second pair of opposing links 206, 208. In the illustrated arrangement, the first pair of opposing links can include the first link 202 and the second link 204 spaced approximately 180 degrees from one another. In the illustrated arrangement, the second pair of opposing links can include the third link 206 and the fourth link 208 spaced approximately 180 degrees from one another. In modified arrangements, the links 202, 204 of the first pair of opposing links can be spaced less than 180 degrees from each the links 206, 208 of the second pair of opposing links.

With reference to FIG. 22, the grasper 200 can include a central shaft 250. The central shaft 250 can be called a longitudinal shaft, longitudinal member, central member, shaft, or member. The central shaft can include a circuit 300, such as a printed circuit board, to connect to other components of the grasper 200 or other components of the robotic system. In the illustrated arrangement, the circuit 300 can be placed inside the central shaft 250.

The central shaft 250 can support the plurality of links 202, 204, 206, 208. Each of the first pair of opposing links 202, 204 and each of the second pair of opposing links 206, 208 can be coupled to the central shaft 250. The first link 202 can have a proximal end 232 and a distal end 222. The second link 204 can have a proximal end 234 and a distal end 224. The third link 206 can have a proximal end 236 and a distal end 226. The fourth link 208 can have a proximal end 238 and a distal end 228. The plurality of links 202, 204, 206, 208 can be connected or operatively connected at their respective proximal ends 232, 234, 236, 238 and/or at their respective distal ends 222, 224, 226, 228.

The first pair of opposing links 202, 204 can each include a finger grip or pad 212, 214. The second pair of opposing links 206, 208 can each include a secondary input 216, 218. Each of the plurality of links 202, 204, 206, 208, can include a secondary link 242, 244, 246, 248 to attach the proximal ends 232, 234, 236, 238 of the links 202, 204, 206, 208 to the central shaft 250.

Each of the plurality of links can be configured to move from an open position where proximal ends 232, 234, 236, 238 of each of the plurality of links 202, 204, 206, 208 are positioned radially away from the central shaft 250 to a closed position where the proximal ends 232, 234, 236, 238 of each of the plurality of links 202, 204, 206, 208 are positioned radially close to the central shaft 250. With reference again to FIG. 21A, the grasper 200 is shown in an open position with the proximal ends 232, 234, 236, 238 of the plurality of links 202, 204, 206, 208 positioned away from the central shaft 250 of the grasper 200. Each of the plurality of links 202, 204, 206, 208 can be connected to the grasper 200 at each of its respective distal ends 222, 224, 226, 228, such that each link can extend or pivot at an angle away from a central shaft 250. The proximal ends 232, 234, 236, 238 of each of the first pair of opposing links 202, 204 and each of the second pair of opposing links 206, 208 are configured to radially move relative to the central shaft 250.

With reference again to FIG. 21B, the grasper 200 is shown in a closed position with the proximal ends 232, 234, 236, 238 of the plurality of links 202, 204, 206, 208 positioned close to the central shaft 250 of the grasper 200. In the closed position, each of the proximal ends 232, 234, 236, 238 can be positioned close to the central shaft 250, such that the each of plurality of links 202, 204, 206, 208 can be parallel in length to the central shaft 250.

Each of the plurality of links 202, 204, 206, 208 can be biased in an open position. In some configurations, each link can be spring-loaded in an open position. In some configurations, there are at least two springs (not shown) for each link with a first spring providing the majority of the force to bias the link in an open position. A second spring can provide a slight haptic feedback when the link reaches a certain degree of closure to indicates to the user when the grasper is closed and that further motion to close the grasper will result in an increase of clamping force of the surgical instrument.

For example, the first pair of opposing links 202, 204 and/or the second pair of opposing links 206, 208 can be maneuvered in a pinching motion, which can be translated to movement of the surgical instrument inside the body. For example, opening and closing the first pair of opposing links 202, 204 would correspond to opening and closing of a scissor tool or jaws of a medical instrument. The facilitated pinching motion can make grasper actuation natural and easy for the user.

The plurality of links 202, 204, 206, 208 on the grasper 200 can that measure the input angle of the user's fingers. For example, the angle at which any one or more of the plurality of links 202, 204, 206, 208 are positioned relative to the central shaft 250 can be translated to the desired angle of a component of the instrument, such as one or more jaws of an end effector of the instrument.

The grasper 200 can have an increased number of links (such as four links as shown in FIGS. 21A-21B and 22) and/or links that are positioned closer to each other. The grasper 200 can also be radial symmetrical, in particular at the most distal end.

By having such a radially symmetric configuration of the grasper, a user can advantageously be capable of performing certain movements with ease (e.g., a roll maneuver) that would otherwise be challenging. If a user wants to do a roll-intensive task with the grasper, such as suturing, the user can only rotate the grasper approximately 180 degrees before their wrist runs out of range of motion without repositioning the user's hand. To continue rolling the grasper, they have to release their current position of the grasper, rotate their wrist and regrip the grasper to continue.

The radially symmetric grasper with the plurality of links spaced less than 180 degrees from each other allows the physician to roll the grasper between their finger-tips while maintaining the desired orientation of the grasper (such as in the closed position or in maintaining the closure angle). This is possible since the user's fingers always make contact with at least two links because of the increased number of plurality of links and reduction of the dead zones that can exist between the plurality of links.

Some users may choose to work outside of the finger pads 212, 214, to hold the plurality of links 202, 204, 206, 208 closer to their distal ends 222, 224, 226, 228 of the plurality of links 202, 24, 206, 208. The grasper 200 advantageously is able to accommodate this and allow for comfortable use both in and out of the finger pads 212, 214. Additionally, when working outside of the finger pads 212, 214 (such as at the distal ends 222, 224, 226, 228 of one or more of the plurality of links 202, 204, 206, 208), the grasper 200 can have radial symmetry, such that the physician can close the grasper 200 (such as closing the first pair of opposing links 202, 204 and/or closing the second pair of opposing links 206, 208) and then roll the grasper 200 between their fingers. When executing this roll maneuver of the grasper 200, it can be desirable to have the grasper 200 remain in the closed position. The first pair of opposing links 202, 204 and/or the second pair of opposing links 206, 208 can be identical and symmetrical at their distal ends 222, 224, 226, 228, allowing the user to use any of the plurality of links 202, 204, 206, 208 to close the grasper 200.

The radial symmetry at the distal end can advantageously be more forgiving of misalignment of the user's hand when operating the grasper 200. Furthermore, the increased number of links being spaced closely together (such as, less than 180 degrees from one another) allows the user to more easily position their fingers to maintain contact with one or more of the plurality of links as they maneuver the grasper 200. For example, when working outside the finger pads 212, 214, the user can use any combination of the plurality of links to actuate the grasper 200. The plurality of links can increase the number of points of contacts for a user to actuate the grasper 200. This can allow the user to maintain contact with the actuators of the grasper more easily, to decrease difficultly of positioning and readjusting of the user's hand. The plurality of links and radial symmetry can give a user more freedom to manipulate the grasper 200.

The first pair of opposing links 202, 204 can be longer in length than the second pair of opposing links 206, 208. The plurality of links can be arranged such that the longer links 202, 204 oppose each other, with the shorter links 206, 208 located between the two. The two longer links 202, 204 can serve as the main grasping links. The longer links 202, 204 can have finger grips, pads, loops such as the finger pads 212, 214 of the illustrated arrangement.

In other examples, the first pair of opposing links 202, 204 and the second pair of opposing links 206, 208 can be of equal length. In other examples, the second pair of opposing links 206, 208 can be longer in length than the first pair of opposing links 202, 204.

Figure 23:
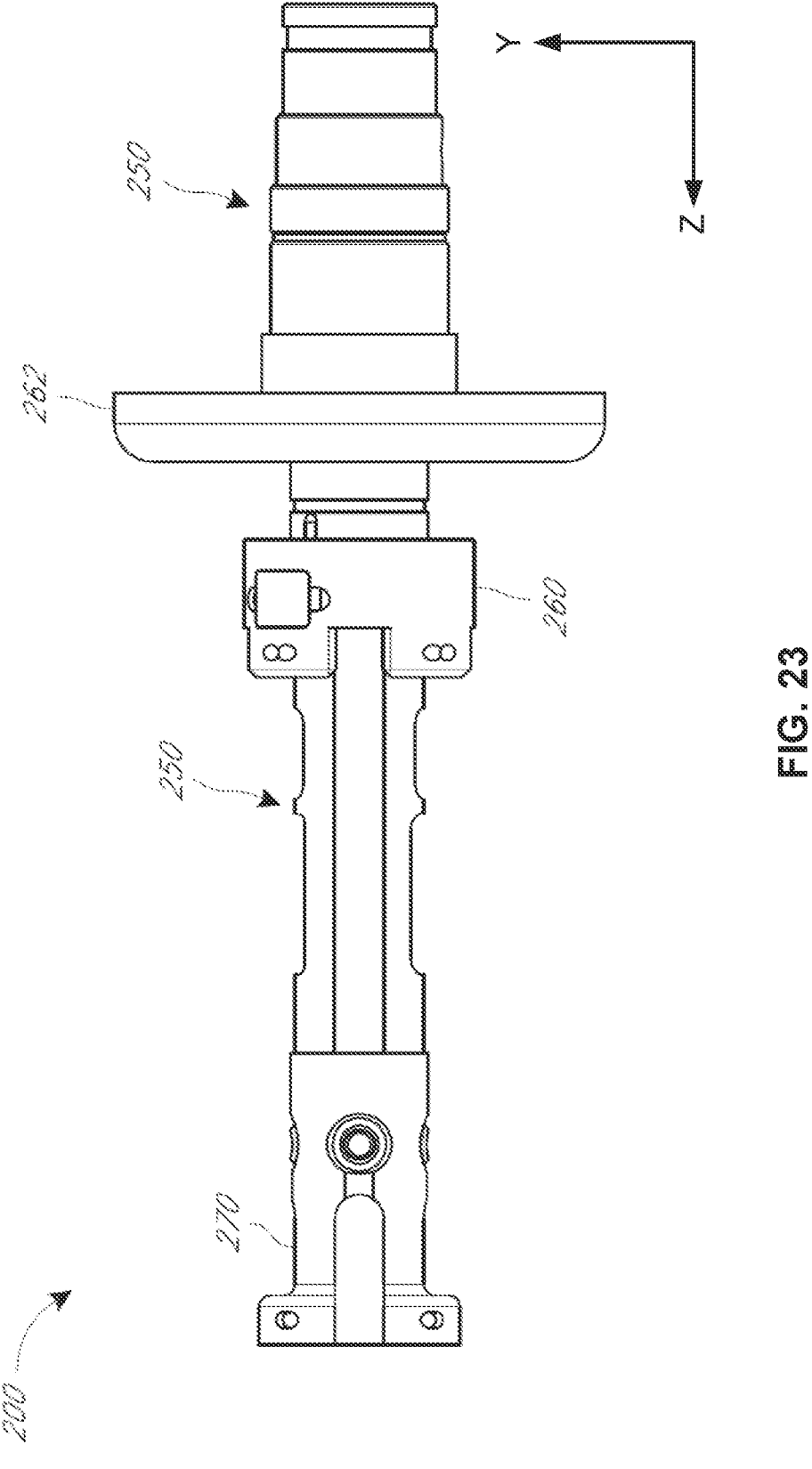
FIG. 23 illustrates the input device of FIGS. 21A-21B and 22 without a plurality of links.
Figure 24A:
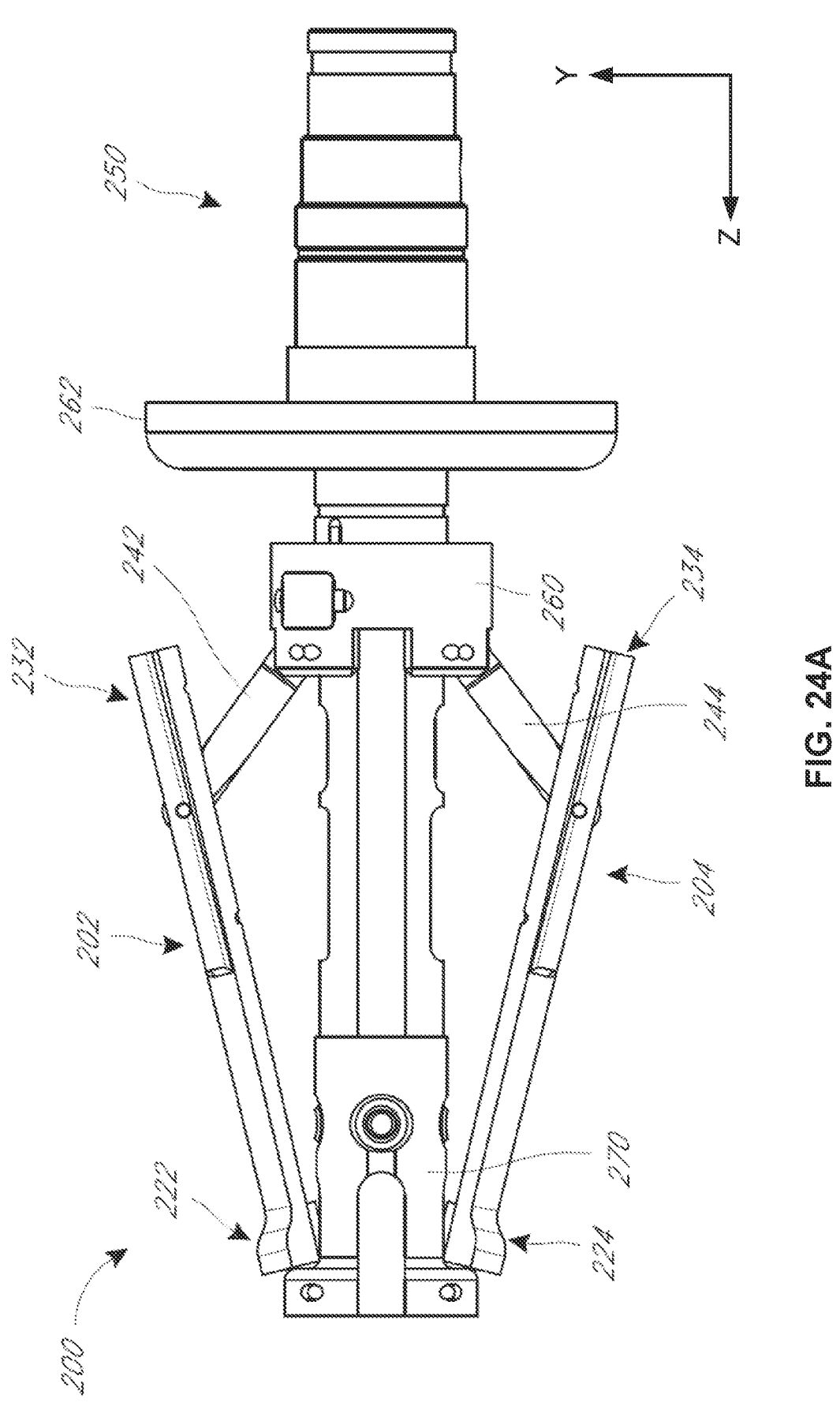
FIG. 24A illustrates the input device of FIGS. 21A-21B and 22-23 without a second pair of links in an open position.

FIG. 23 illustrates the grasper of FIGS. 21A-21B and 22 without the plurality of links to show the central support shaft 250 and a sliding support 260 in more detail. The main support shaft 250 can serve as a bearing surface for the sliding support 260. The slide or a sliding support 260 can be connect to the plurality of links 202, 204, 206, 208 as shown in FIG. 24A. The main support shaft 250 can engage with or connect to the sliding support 260 to constrain of links 202, 204, 206, 208 relative to the central support shaft 250 while still allowing translation of the rotation of the plurality of links 202, 204, 206, 208 relative to the central support shaft 250. For example, the central support shaft 250 can have slots or recesses to receive portions of the sliding support 260 or receive keys that connect to the sliding support 260. Additionally, the keys can serve as stops to limit the translation of the sliding support 260. In some examples, the limit of translation can be approximately 5 mm.

Figure 24B:
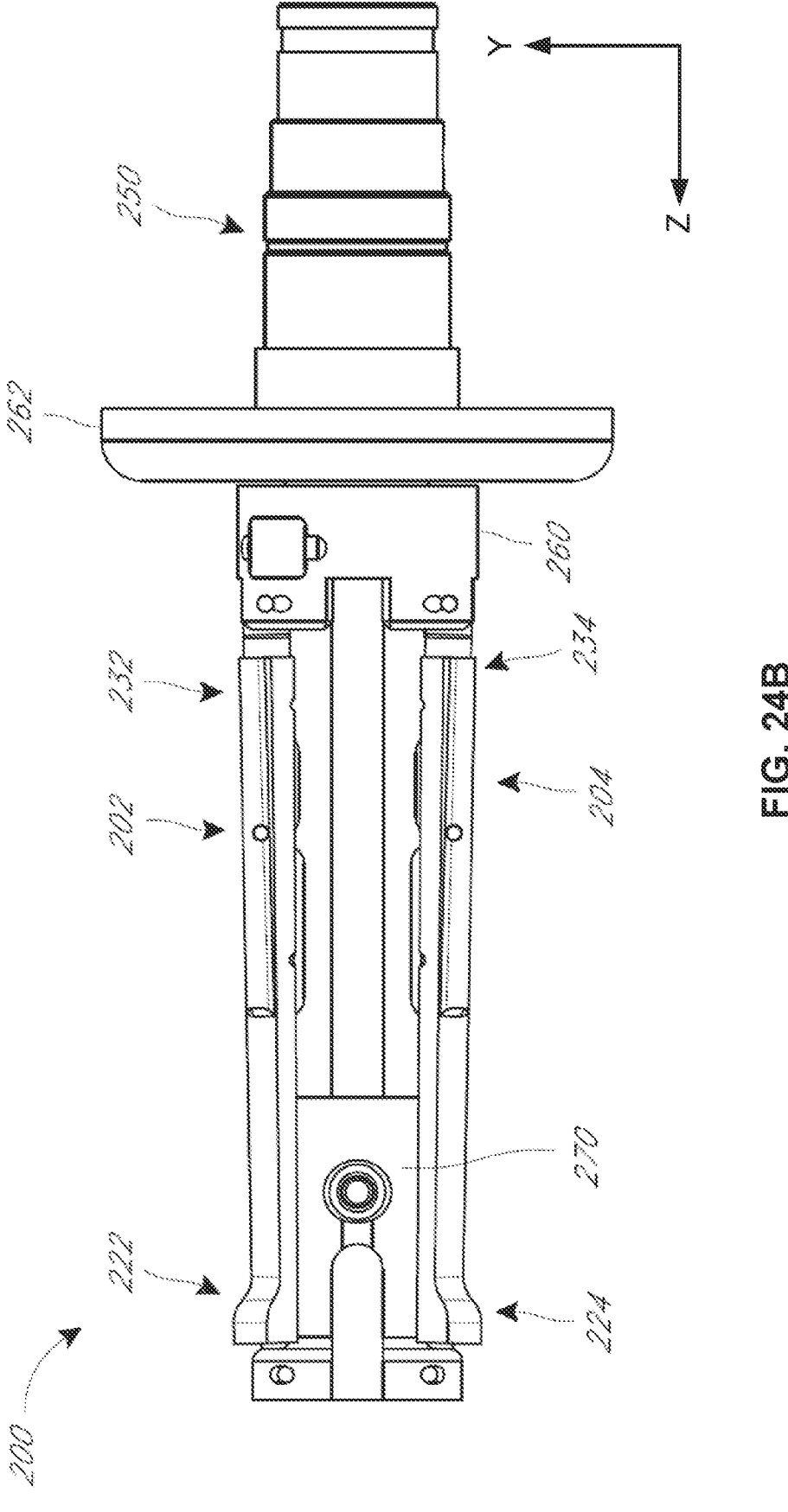
FIG. 24B illustrates the input device of FIG. 24A in a closed position.

FIGS. 24A and 24B illustrate the grasper without the second pair of links 206, 208 for clarity. FIG. 24A illustrates the grasper with the first pair of links 202, 204 in the open position. FIG. 24B illustrates the grasper with the first pair of links 202, 204 in the closed position. As illustrated, the first pair of links 202, 204 can be connected at their respective proximal ends 232, 234 to the sliding support 260. For example, each of the plurality of links 202, 204, 206, 208 can be connected to the sliding support 260 with secondary links 242, 244, respectively. The secondary links 242, 244, can be free to pivot to change an angular displacement of the respective link 202, 204 into an axial translation of the sliding support 260 along the central shaft 250. In the open position as shown in FIG. 24A, the sliding support 260 can be positioned towards the proximal end of the grasper 200, such that the secondary links 242, 246 and the first pair of links 202, 204 are each angled away from the central shaft 250. As the sliding support 260 is moved in a distal direction, the secondary links 242, 244 are angled farther away from the central shaft 250, which in turn moves the proximal ends 232, 234, 236, 238 away from the central shaft 250. In the closed position as shown in FIG. 24B, the sliding support 260 can be positioned more proximally along the central shaft 250, such that the first pair of links 202, 204 and the secondary links 242, 248 are extended and angularly positioned closer to the central shaft 250. In the open position, the sliding support 260 can be positioned such that the first pair of links 202, 204 and/or the secondary links 242, 244 are fully extended in length and substantially parallel to the central support 250. In this configuration, axial displacement in one of the links 202, 204 causes the same displacement in the other link 202, 204. In this configuration, the motion of the first pair of links 202, 204 are constrained together. Each of the first pair of opposing links 202, 204 can be configured to move together, such that proximal ends 232, 234 of the first pair of opposing links 202, 204 are positioned equally distant from the central shaft 250.

In some of the configurations, each of the first pair of opposing links 202, 204 are configured to move together. In some configurations, each of the second pair of opposing links 206, 208 are configured to move together. In some of the configurations, the first pair of opposing links 202, 204 and the second pair of opposing links 206, 208 are configured to move together. In some of the configurations, the first pair of opposing links 202, 204 and the second pair of opposing links 206, 208 are configured to move independently. In some configurations, each of the plurality of links are configured to move independently. In some configurations, each of the plurality of links are configured to move together.

Although not shown in FIG. 24A-24B for clarity, the second pair of links 206, 208 can similarly be connected at their respective proximal ends 236, 238 can be connected to the sliding support 260 with secondary links 246, 248, respectively. In the illustrated arrangement, all four links 202, 204, 206, 208 can be connected to the same sliding support 260. In this configuration, axial displacement in one of the plurality of links 202, 204, 206, 208 causes the same displacement in the remaining three of the plurality of links 202, 204, 206, 208. In this configuration, the motion of the plurality of links 202, 204, 206, 208 are constrained together.

The grasper 200 can include a proximal plate 262. The proximal plate 262 can be attached to or integral with the central support shaft 250. The proximal plate 262 can be positioned about the central support shaft 250 towards the proximal end of the central support shaft 250. The proximal plate 262 can act as a stop to limit axial translation of the sliding support 260. In some examples, the proximal plate 262 can be positioned to prevent the sliding support 260 from extending the plurality of links 202, 204, 206, 208 past the lengths of the plurality of links 202, 204, 206, 208 and/or the secondary links 242, 244, 246, 248. In some examples, the proximal plate 262 can also serve as an additional surface to support the user's hand.

The plurality of links 202, 204, 206, 208 can be connected or operatively connected at their respective distal ends 222, 224, 226, 228. For example, the plurality of links 202, 204, 206, 208 can be connected or operatively connected at their respective distal ends 222, 224, 226, 228 to the distal link support 270. The plurality of links 202, 204, 206, 208 can be connected or operatively connected at their respective proximal ends 232, 234, 236, 238.

Figures 25A, 25B:
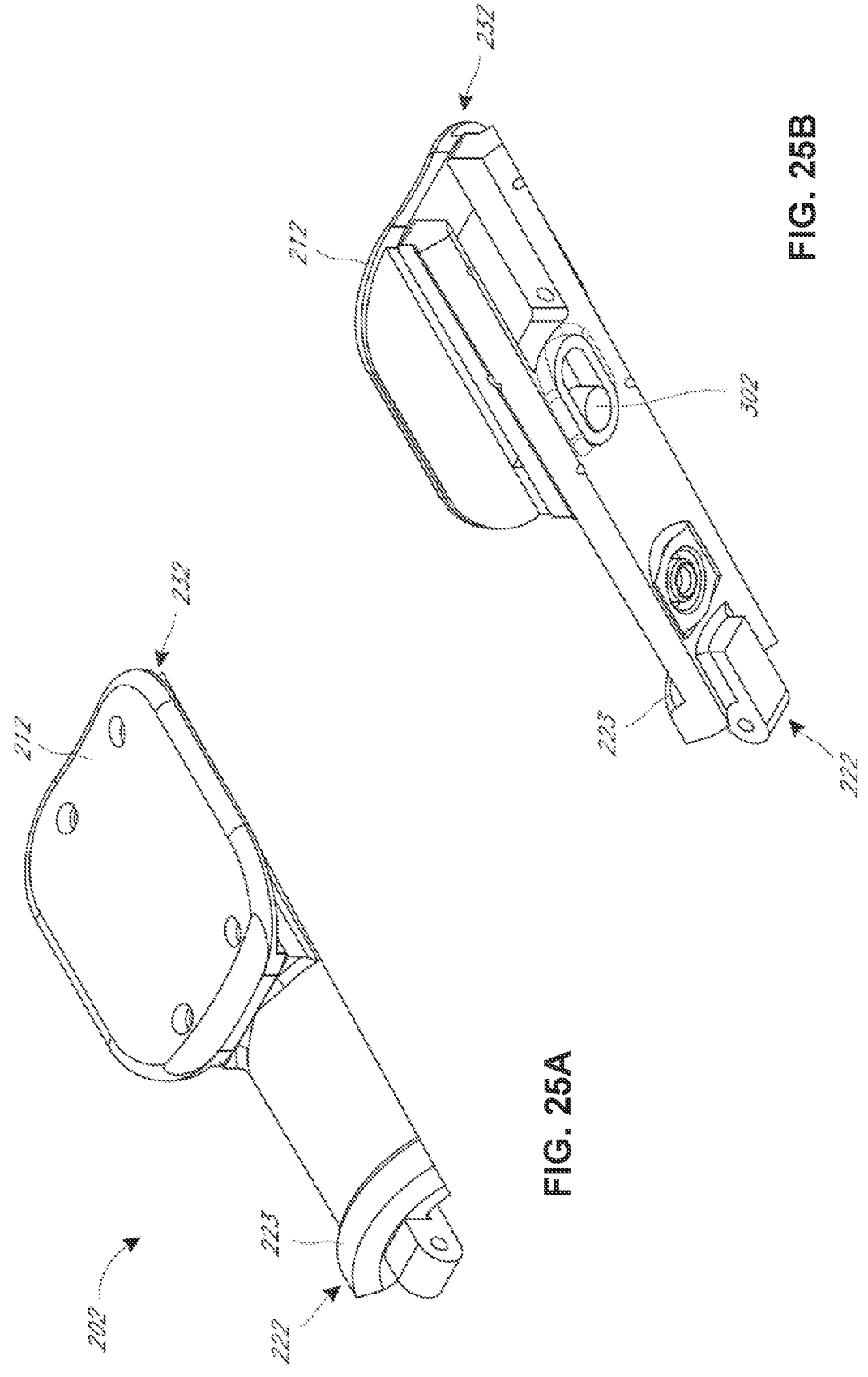
FIG. 25A illustrates a top view of a first link with a finger pad.
FIG. 25B illustrates a bottom view of the first link of FIG. 25A.

FIG. 25A illustrates a top view of a first link 202 with a finger pad 212. FIG. 25B illustrates a bottom view of the first link 202 with the finger pad 212 of FIG. 25A. Although only the first link 202 of the first pair of links 202, 204 is shown in FIGS. 25A-25B, the second link 204 and figure pad 214 can be substantially similar. The first pair of opposing links 202, 204 can each include a finger pad 212, 214, respectively. The finger pads 212, 214 can facilitate manipulation of the finger links 202, 204 by increasing the surface area by which the user can contact and maneuver the opposing links. The finger pads 212, 214 can be attached to the respective links 202, 204 by bolts. A Velcro loop (not shown) can be positioned between the finger pads 212, 214 and the respective links 202, 204 to secure around a user's finger when in use.

The first pair of links 202, 204 can each include a distal ridge 223, 243 located at the distal ends 222, 224 of the first pair of links 202, 204, The distal ridges 223, 243 can each follow the contour of the respective link 202, 204. The distal ridges 223, 243 can be ergonomic features that allows the physician to easily grip and maneuver the grasper 200 at the distal end. For example, the distal ridges 223, 243 can act as a surface to enable a user to pull the grasper 200 towards them when working outside the finger pads 212, 214.

The first pair of links 202, 204 can each include a magnet 302, 304 used to sense the position of the respective pair of links 202, 204. As shown in FIG. 25B, a magnet 302 can be positioned or mounted on the bottom of the link 202. Angular displacements of the link 202 can be sensed by a hall effect sensor. The hall effect sensor can be positioned on or in the central shaft 250. The hall effect sensor can be used to measure the magnitude or changes in the magnetic field. As the plurality of links changes angles, the one or more sensors can be used to detect the change in magnetic field due to the motion of the magnets 302, 304, which occurs through motion of the respective links 202, 204. In some configurations, the hall effect sensor can be used to detect the distance of the magnet 302, 304 and thus the links 202, 204 with respect to the central shaft 250, which can be used by the input device to transmit control signals. Similarly, the second pair of links 206, 208 can also each include a magnet. Additionally, other sensors can be used, such as resistance sensors and/or optical sensors.

B. Secondary Input

In some configurations, at least one secondary input is included on one of the plurality of links (such as the secondary input 216 as shown in FIGS. 21A-21B and 22). The secondary input can be also known as a finger input or as the specific function of the secondary input, such as a clutch. In some embodiments, by pressing down on the clutch, this temporarily decouples movement of the instrument from the controller. One or more of the first pair of opposing links 202, 204 can include a secondary input. One or both of the second pair of opposing links 206, 208 can include a secondary input. It is useful to have a secondary input 216, 218 on the grasper 200 to allow for other control schemes. In some configurations, the secondary inputs 216, 218 can be multi-functional finger inputs that can serve different purposes depending on different modes. For example, the secondary inputs can serve a first mode and a second mode. In the first mode, the secondary input serves as a clutch. In the second mode, the secondary input serves as a selecting tool, such as a menu/tool selector for a user interface. For example, the secondary input can act as a clutch. Often times the user must reorient his or her hand position during the procedure. Actuation of any of the finger clutches can temporarily decouple the grasper from controlling operation of the instruments, thereby allowing a user to reorient his or her hand position to regrip the grasper during a procedure.

To maintain the radial symmetrical configuration of the grasper, it can be challenging in terms of size or volume for secondary inputs. In some configurations, it can be advantageous to position the secondary input on one or more of the plurality of links 202, 204, 206, 208. In some examples, such as shown in FIGS. 21A-21B and 22, the second pair of links 206, 208 can include secondary inputs 216, 218. In some configurations, the secondary input can be placed on links without finger pads or on links positioned between links with finger pads. This configuration can allow a user to be able to easily access the secondary input while maneuvering the grasper. This configuration can also reduce the size of the secondary input and minimize interference of the secondary input with the radial symmetry of the grasper and can maximize the remaining space for the user to actuate the plurality of links 202, 204, 206, 208.

FIGS. 27A-27B and 28-30 show various configurations of the third link 206 with a secondary input. Although only the third link 206 is shown in these figures, the fourth link 208 can be substantially similar. The secondary input can be a sliding input, a push input, a translational input or a rotary input.

Figures 26A, 26B:
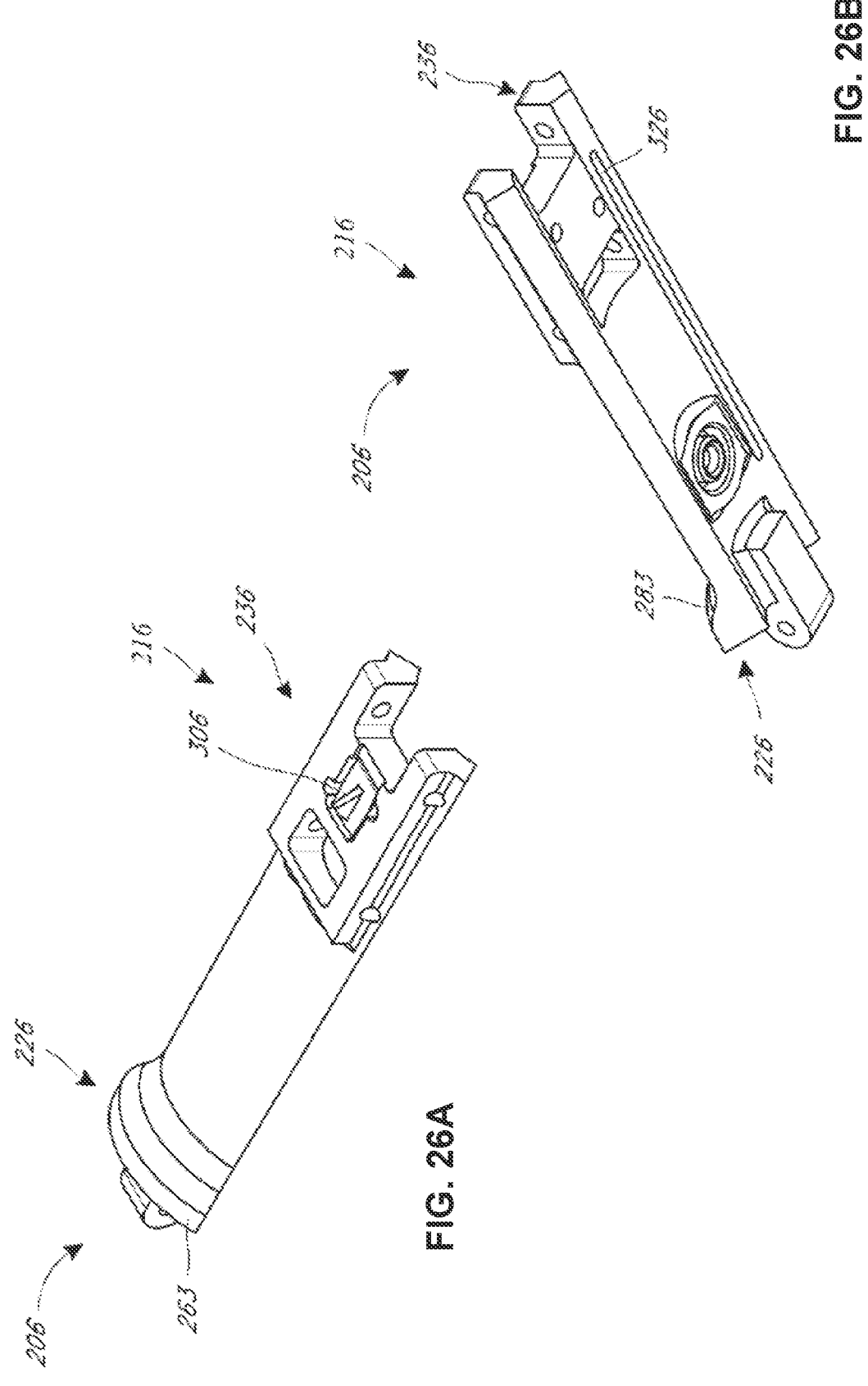
FIG. 26A illustrates a top view of a third link with a secondary input.
FIG. 26B illustrates a bottom view of the third link of FIG. 26A.

FIG. 26A illustrates a top view of the third link 206 with a secondary input 216 of FIGS. 21A-21B and 22. FIG. 26B illustrates a bottom view of the third link 206 of FIG. 26A. Although only the third link 206 of the second pair of links 206, 208 is shown in FIGS. 26A-26B, the fourth link 208 can be substantially similar. The second pair of opposing links 206, 208 can include a switch 306. The switch 306 can be positioned on the top side of each of the links 206, 208, towards their respective proximal ends 236, 238. The switch 306 can be connected to a circuit 300 inside the central support 250. As shown in FIG. 26B, each of the second pair of links 206, 208 can include a wire guide 326 to connect the switch 306 to the circuit 300.

Similar to the distal ridges 223, 243 of the first pair of links 202, 204, the second pair of links 206, 208 can also each have a distal ridge 263, 283 located at the distal ends 226, 228 of the second pair of links 206, 208. The distal ridges 263, 283 can each follow the contour of the respective link 206, 208. The distal ridges 263, 283 can be ergonomic features that allows the physician to easily grip and maneuver the grasper 200 at the distal end. For example, the distal ridges 263, 283 can act as a surface to enable a user to pull the grasper 200 towards them when handling the grasper 200 at the distal end.

Figure 27A:
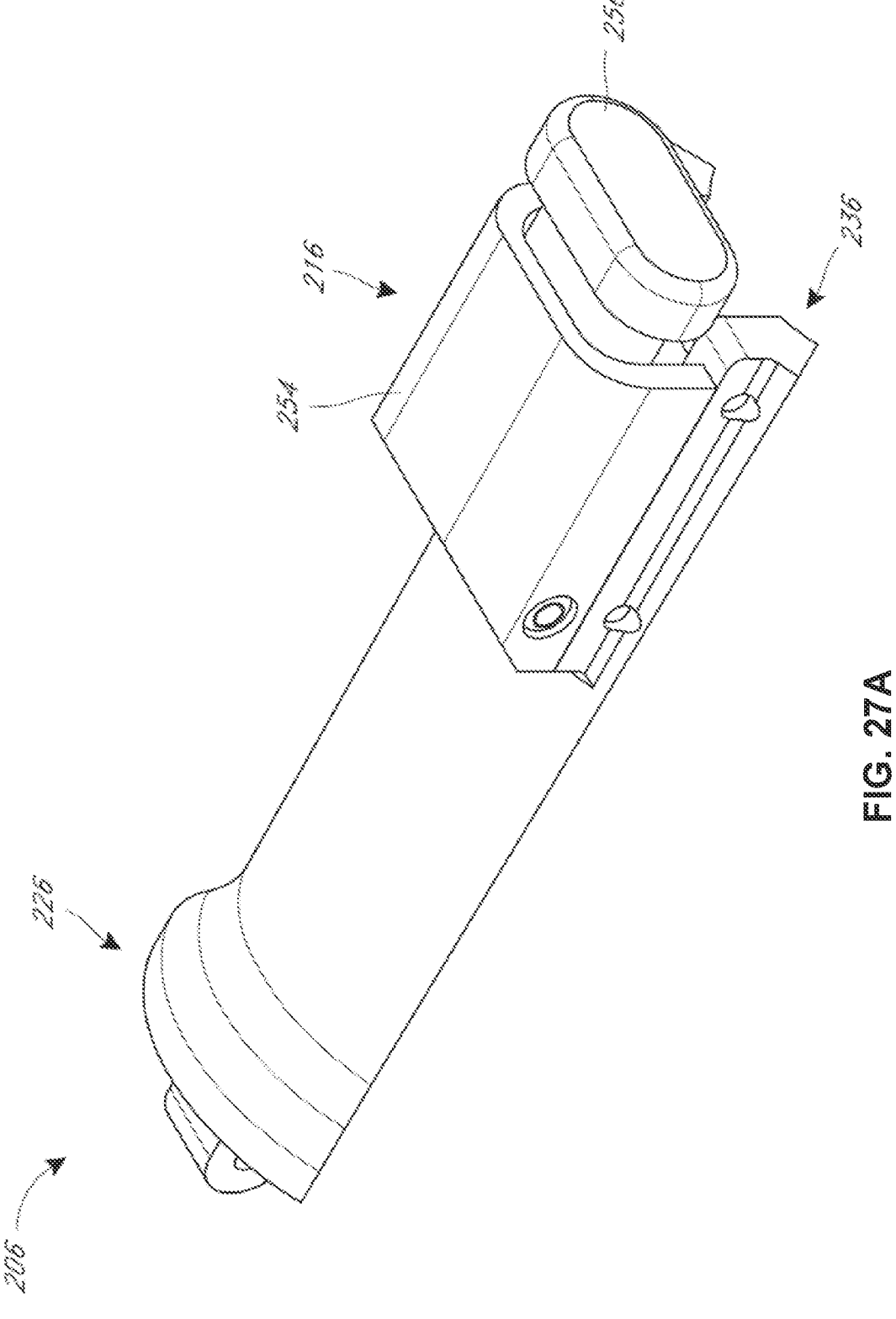
FIG. 27A illustrates another example of a third link with a secondary input.
Figure 27B:
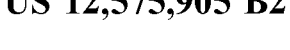
FIG. 27B illustrates a cross sectional view of the third link of FIG. 27A.

The secondary input can come in many different forms to activate the switches 306, 308. FIG. 27A illustrates another example of a third link with a secondary input. FIG. 27B illustrates a cross sectional view of the third link of FIG. 27A. As shown in FIG. 27A, the secondary input 216 can include a push button 256. The push button 256 can be considered a clutch button if the secondary input is a clutch for the grasper. Often times the user must reorient his or her hand position during the procedure. Actuation of the clutch, such as through a secondary input, can temporarily decouple the grasper from controlling operation of the instruments, thereby allowing a user to reorient his or her hand position to regrip the grasper during a procedure. The secondary input 216 can include a cover 254 that is wrapped around the entire assembly to protect the secondary input 216 from accidental impacts.

As shown in FIG. 27B, the push button 256 can be spring loaded. The secondary input 216 can include a surface or rail 258 that can engage with the switch 306. The push button 256 can be mounted on a rail 258 on which the push button 256 slides on. The push button 256 can be constrained on the rail 258, such as by a dowel pin, to which the axial translation of the button along the rail 258. As the push button 256 is actuated by a user, the push button 256 can engage with the switch 306 to activate a another control scheme, such as a clutch mode. The push button 256 can be positioned at the proximal end 236 of the third link 206 such that the user can hook their finger around the proximal end 236 of the third link 206 to actuate the push button 256.

Figure 28:
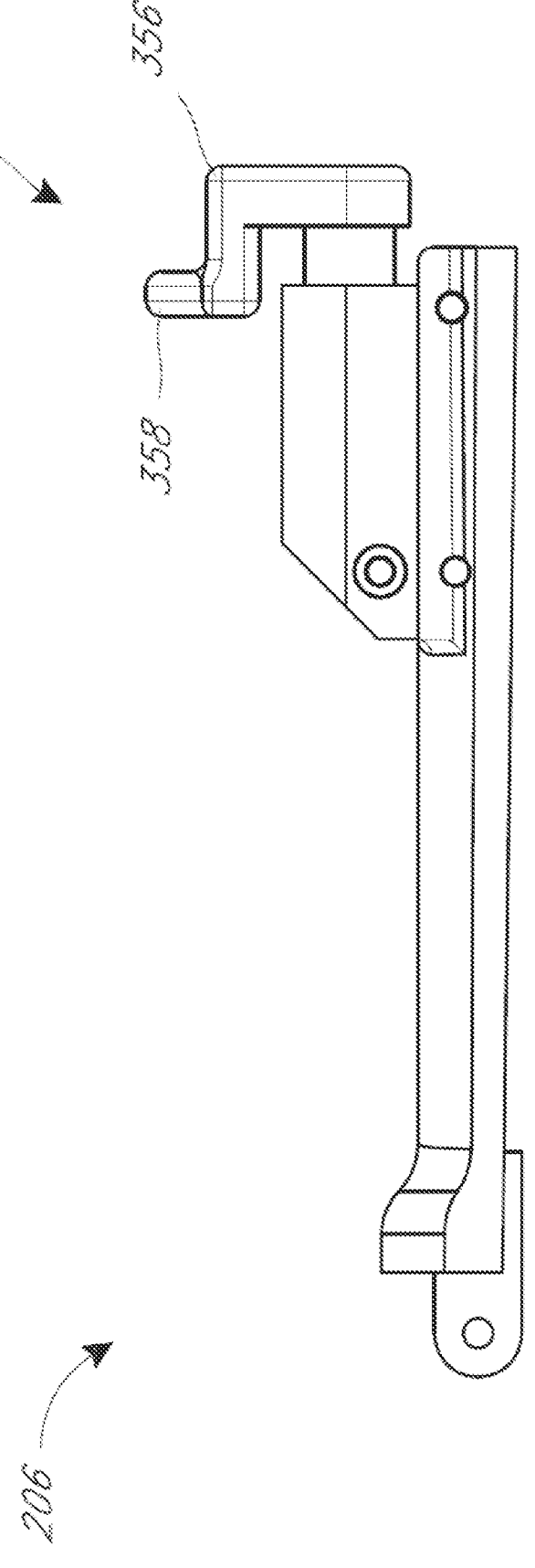
FIG. 28 illustrates yet another example of a third link with a secondary input.

FIG. 28 illustrates yet another example of a third link 206 with another arrangement of a secondary input 316. The secondary input 316 can be similar to the secondary input 216 as shown in FIGS. 27A-27B. The secondary input 316 can include a push button 356 with a ledge, protruding ledge, or protrusion 358. The ledge or protrusion 358 can provide an additional surface which the user can actuate the push button 356. The ledge or protrusion 358 can be especially useful for users with shorter fingers who can more comfortably reach the ledge or protrusion 358 than the proximal end of the push button 256.

Figure 29A:
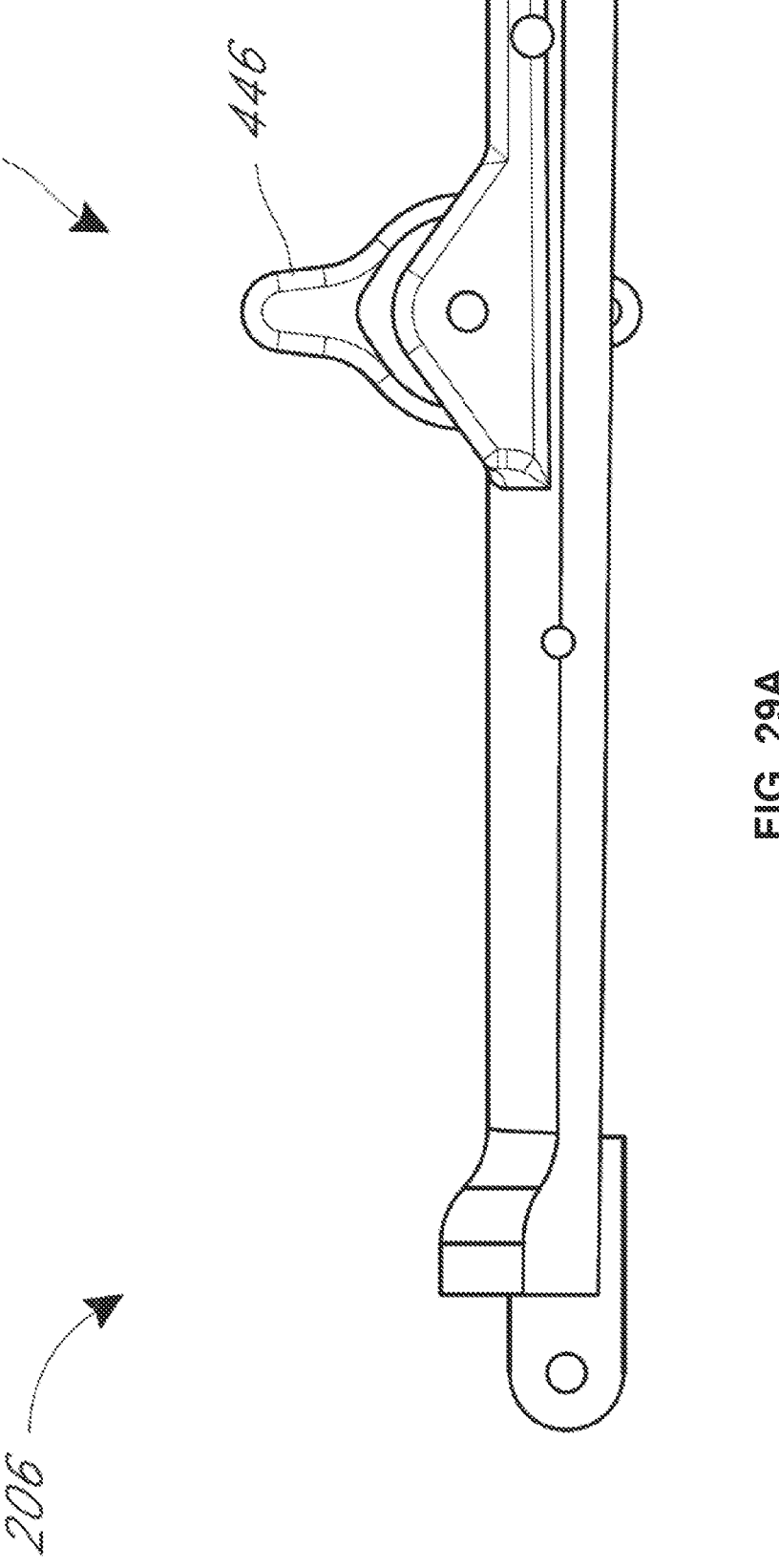
FIG. 29A illustrates yet another example of a third link with a secondary input.

FIG. 29A illustrates yet another example of a third link 206 with another arrangement of a secondary input 416. The secondary input 416 can include a rotary based device or a roller 446. The user provides a linear motion on the edge of the roller 446 which is translated into rotary motion of the roller 446. The roller 446 can be advantageous as it can be small in size, which minimizes the secondary input 416 and maximizes the space for the user to actuate the plurality of links. Additionally, the rotary based device 446 can be smaller, simpler, and more robust than translational mechanisms. For example, the rotary based device 446 can advantageously provide rotary motion that feels of large travel without taking up the space of a large translational mechanism. The rotary based device 446 is also advantageously simpler than a similarly sized translational mechanism. The rotary based device 446 can take up less space without compromising user experience. Additionally, with a rotary based device 446, there are minimal sliding surfaces, improving wear and life of the rotary based device 446.

The actuation of the roller 446 can engage with and activate a switch (such as switch 306 as shown in FIGS. 26A and 27B). In some examples, the actuation of the roller 446 can be detected by a sensor. In some examples, the rotary based device or roller 446 can be coupled to a magnet. In some examples, actuation of the roller 446 can change a magnetic field that can be detected by a sensor, such as an analog magnetic sensor. In some examples, actuation of the roller 446 can rotate a magnet directly, which can orient the magnetic field in a different direction through rotation of the magnet. The change in direction of the magnetic field can be detectable by the sensor. In other examples, actuation of the roller can cause linear motion of the magnet, which can also detectable by the sensor.

Figure 29B:
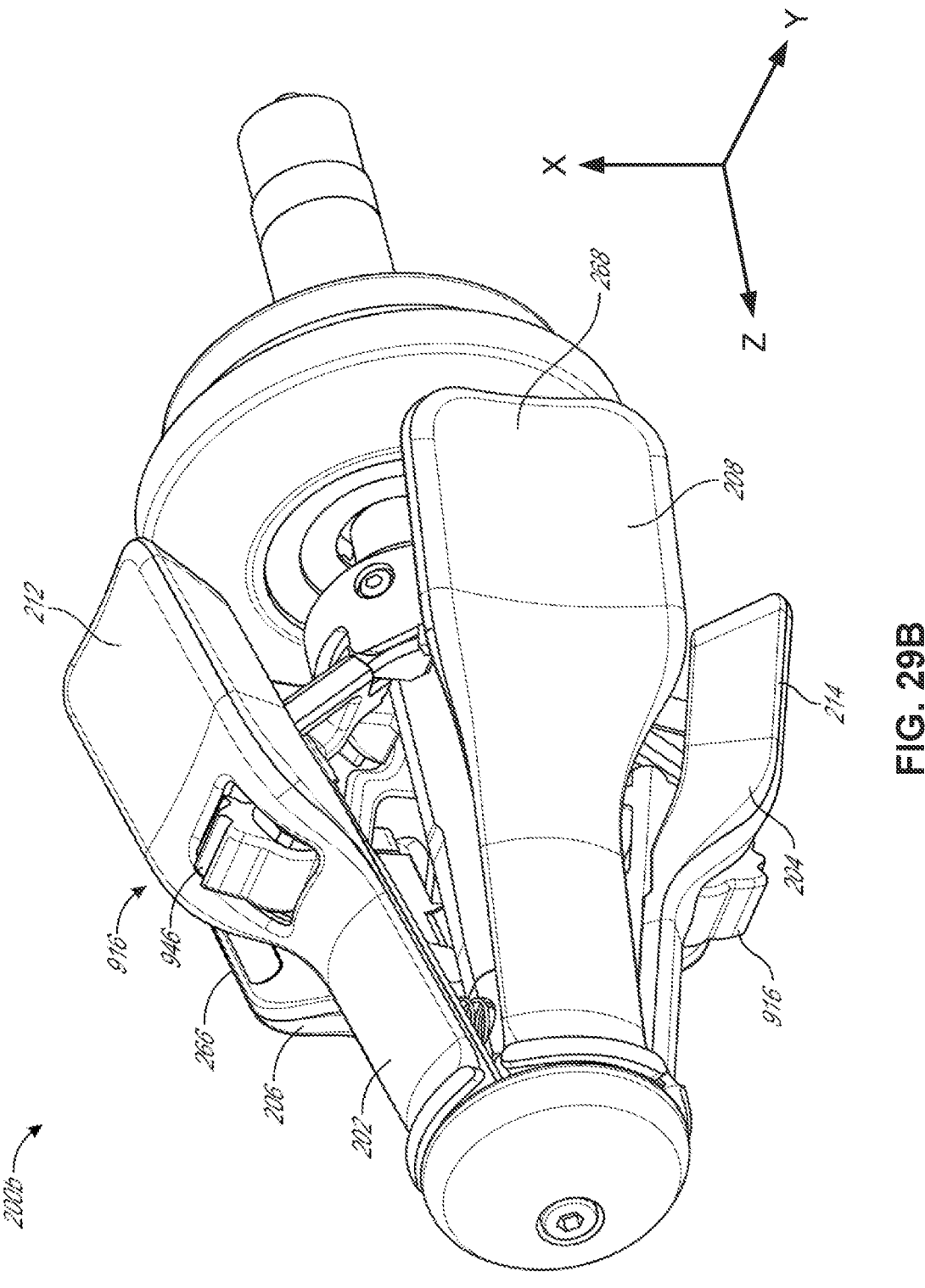
FIG. 29B illustrates another example of a grasper with a secondary input.

FIG. 29B illustrates yet another example of a grasper 200b with a secondary input 916 on the first pair of opposing links 202, 204. Although illustrated on the first pair of opposing links 202, 204 in FIG. 29B, in some embodiments, the secondary input 916 can alternatively or additionally be positioned on the second pair of opposing links 206, 208. The grasper 200b can be similar to the grasper 200 described above. Each of the links 202, 204, 206, 208 can include a finger grip or pad 212, 214, 266, 268.

Figure 29C:
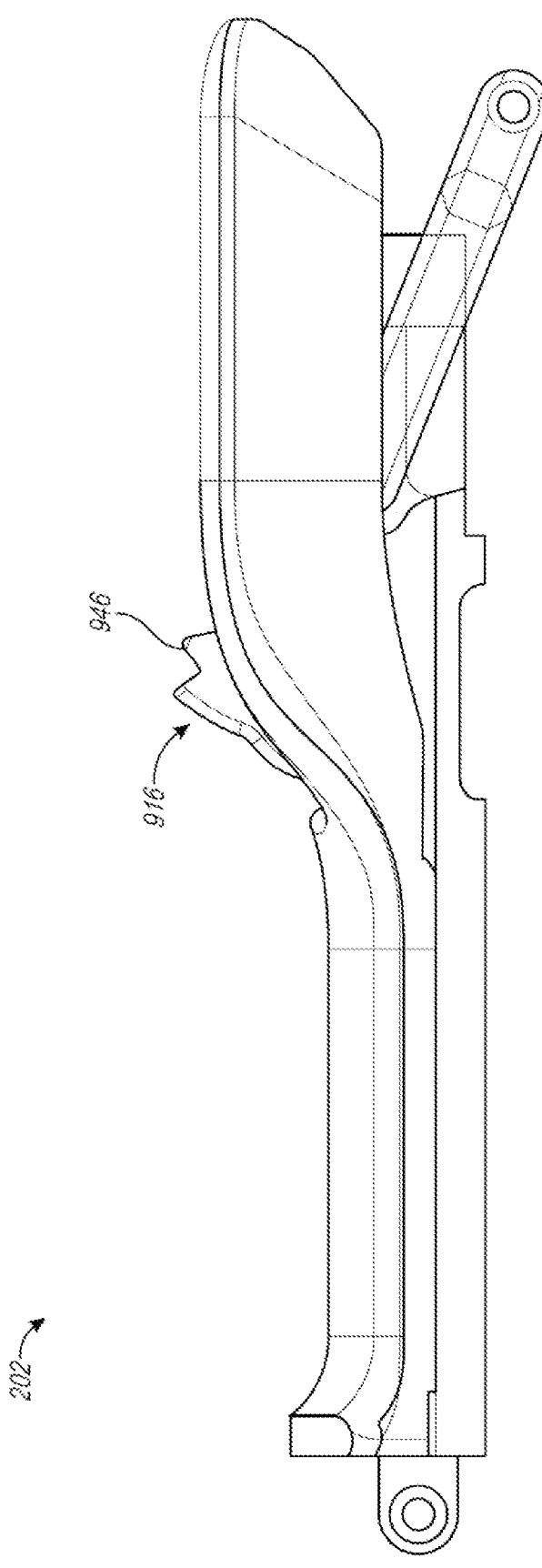
FIG. 29C illustrates an example of a first link with a secondary input.
Figure 29D:
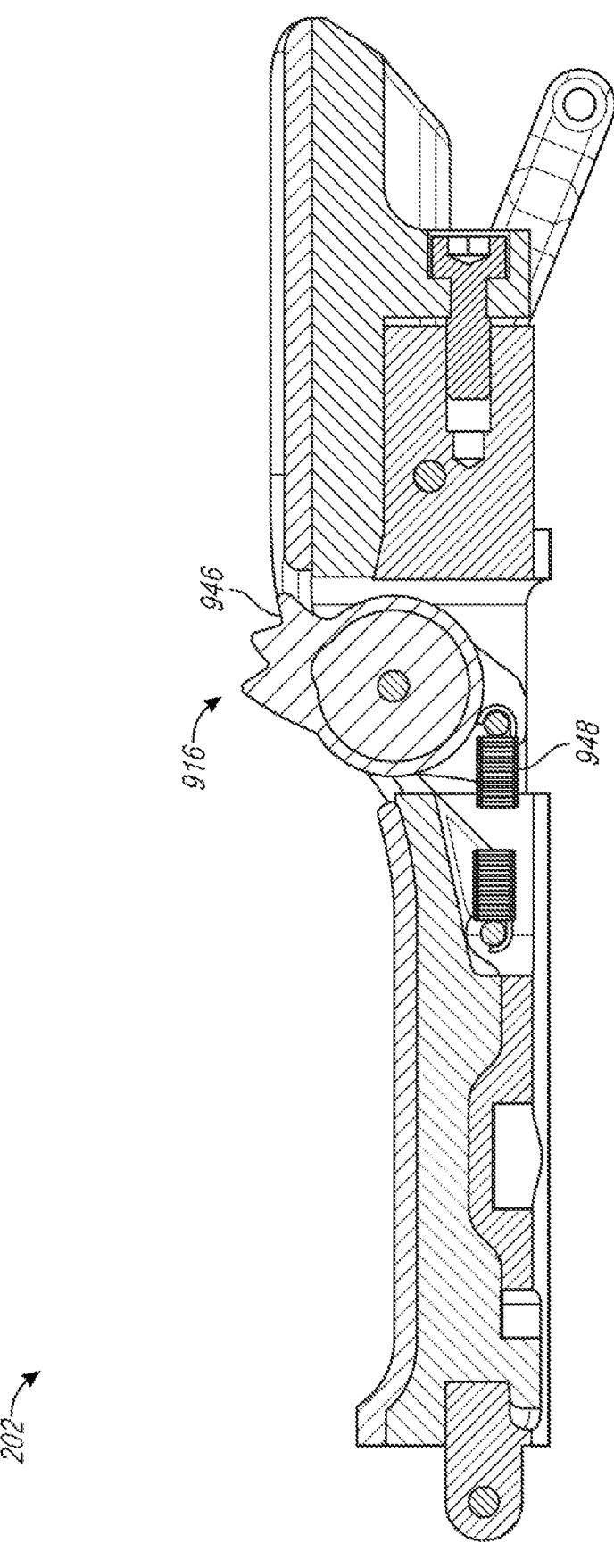
FIG. 29D illustrates a cross sectional view of the first link of FIG. 29C.

FIG. 29C illustrates a first link 202 with an arrangement of a secondary input 916. FIG. 27D illustrates a cross sectional view of the first link of FIG. 29C. Similar to the secondary input 416 of FIG. 29A, the secondary input 916 of FIGS. 29B-D can include a rotary based device or a roller 946. The user provides a linear motion on the edge of the roller 946 which is translated into rotary motion of the roller 946. The roller 946 can provide similar advantages with respect to size, simplicity, robustness, space, and wear. Additionally, the actuation of the roller 946 can similarly engage with and activate a switch (such as switch 306 as shown in FIGS. 26A and 27B). In some examples, the actuation of the roller 946 can be detected by a sensor. In some examples, the rotary based device or roller 946 can be coupled to a magnet. In some examples, actuation of the roller 946 can change a magnetic field that can be detected by a sensor, such as an analog magnetic sensor. In some examples, actuation of the roller 946 can rotate a magnet directly, which can orient the magnetic field in a different direction through rotation of the magnet. The change in direction of the magnetic field can be detectable by the sensor. In other examples, actuation of the roller can cause linear motion of the magnet, which can also detectable by the sensor.

Figure 30:
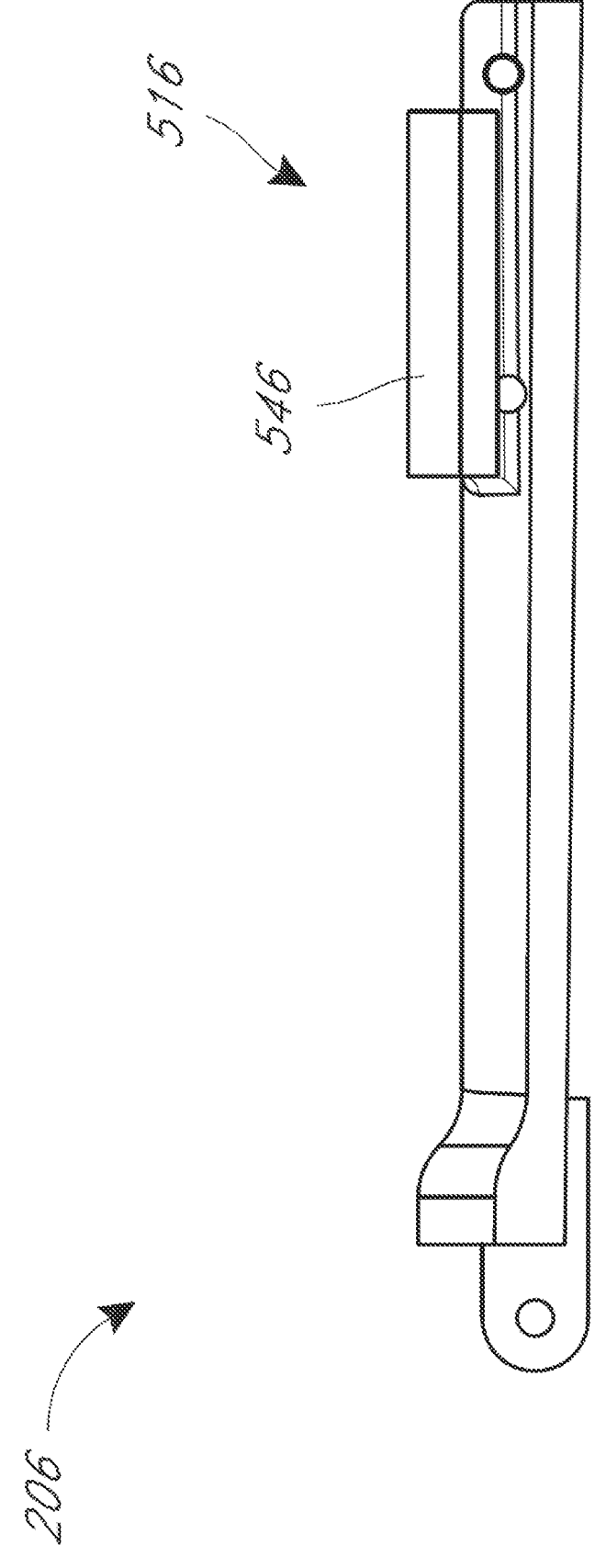
FIG. 30 illustrates yet another example of a third link with secondary input.

FIG. 30 illustrates yet another example of a third link 206 with a secondary input 516. The secondary input 516 can be a translating pad 546 that moves along the length of the third link 206. The translating pad 546 can be advantageous in that it is reduces the height of the secondary input 516 on the third link 206.

The actuation of the translating pad 546 can engage with and activate a switch (such as switch 306 as shown in FIGS. 26A and 27B). In some examples, the actuation of the translating pad 546 can be detected by a sensor. In some examples, the translating pad 546 can be coupled to a magnet. In some examples, actuation of the translating pad 546 can change a magnetic field that can be detected by a sensor, such as an analog magnetic sensor. In some examples, actuation of the translating pad 546 can cause linear motion of the magnet, which can be detectable by the sensor.

C. Alternative Multi-Link Graspers

Figure 31:
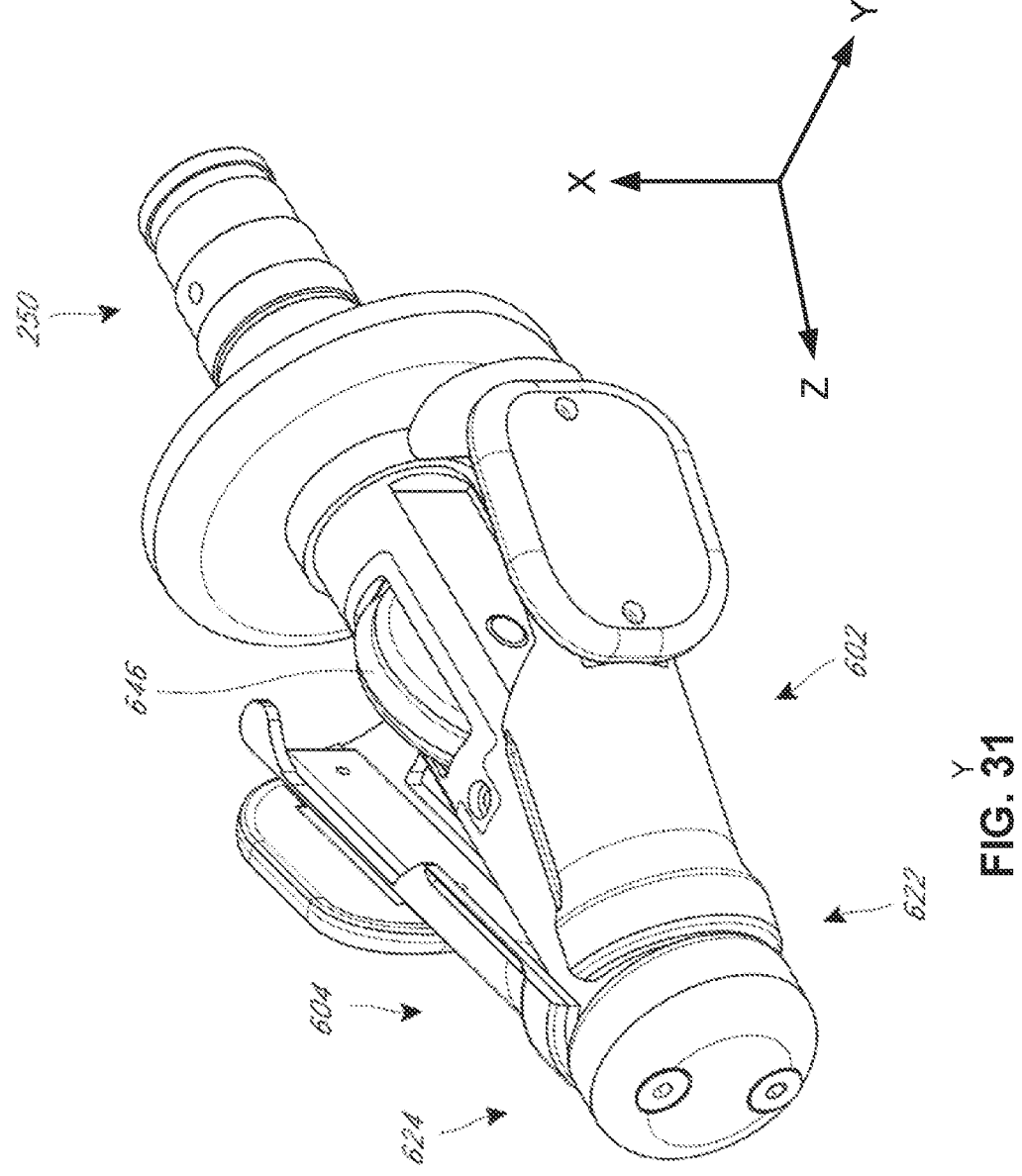
FIG. 31 illustrates another example of an input device.

FIG. 31 illustrates another example of a grasper 600. The grasper 600 only has two links 602, 604. Each link 602, 604 can have a curved face at the distal ends 622, 624 that wrap around the central support 250. Each link 602, 604 can have a curved faces at the distal ends 622, 624 of each of the links 602, 604 or at the distal end of the central shaft 250 or the grasper 600, allowing more freedom as to where the user can grab the links 602, 604. The grasper 600 can have partial radial symmetry. The curved faces of the grasper 600 allows the roll maneuver, where the user can closing the links 602, 604 and roll the grasper 600 between the user's fingers without opening the links 602, 604. The secondary input of the grasper 600 can be a wheel or roller mechanism 646 that can be positioned on the central shaft 250, not mounted on a link.

Figure 32:
FIG. 32 illustrates a cross sectional view of another example of a an input device.
Figure 32:

FIG. 32 illustrates a cross sectional view of another example of a grasper 700. The grasper 700 can be similar to the four-link grasper as shown in FIGS. 21A-21B and 22, but with a different mechanism for connecting the motion of the plurality of links. Although FIG. 32 shows only two links 202, 204 for clarity, the grasper 700 can include any number of links, such as two, three or four links.

The grasper 700 can include a four-sided rack gear 770. Each of the plurality of links 202, 204, 206, 208 can have gear teeth that are configured to engage or mate with the gear teeth of the rack gear 770. As one of the links 202, 204, 206, 208 move between the open and closed configurations, the plurality of links 202, 204, 206, 208 cause the rack gear 770 to translate forward or backward (or proximally or distally), which forces the remaining of the plurality of links 202, 204, 206, 208 to move in the same manner. In this configuration, the motion of the plurality of links 202, 204, 206, 208 are constrained together. Each of the plurality of links 202, 204, 206, 208 can be configured to rotate relative to the rack gear 770, wherein each of the plurality of links 202, 204, 206, 208 are configured to engage with the rack gear 770 such that rotation of one of the plurality of links 202, 204, 206, 208 causes rotation of remaining links of the plurality of links 202, 204, 206, 208.

Figure 33:
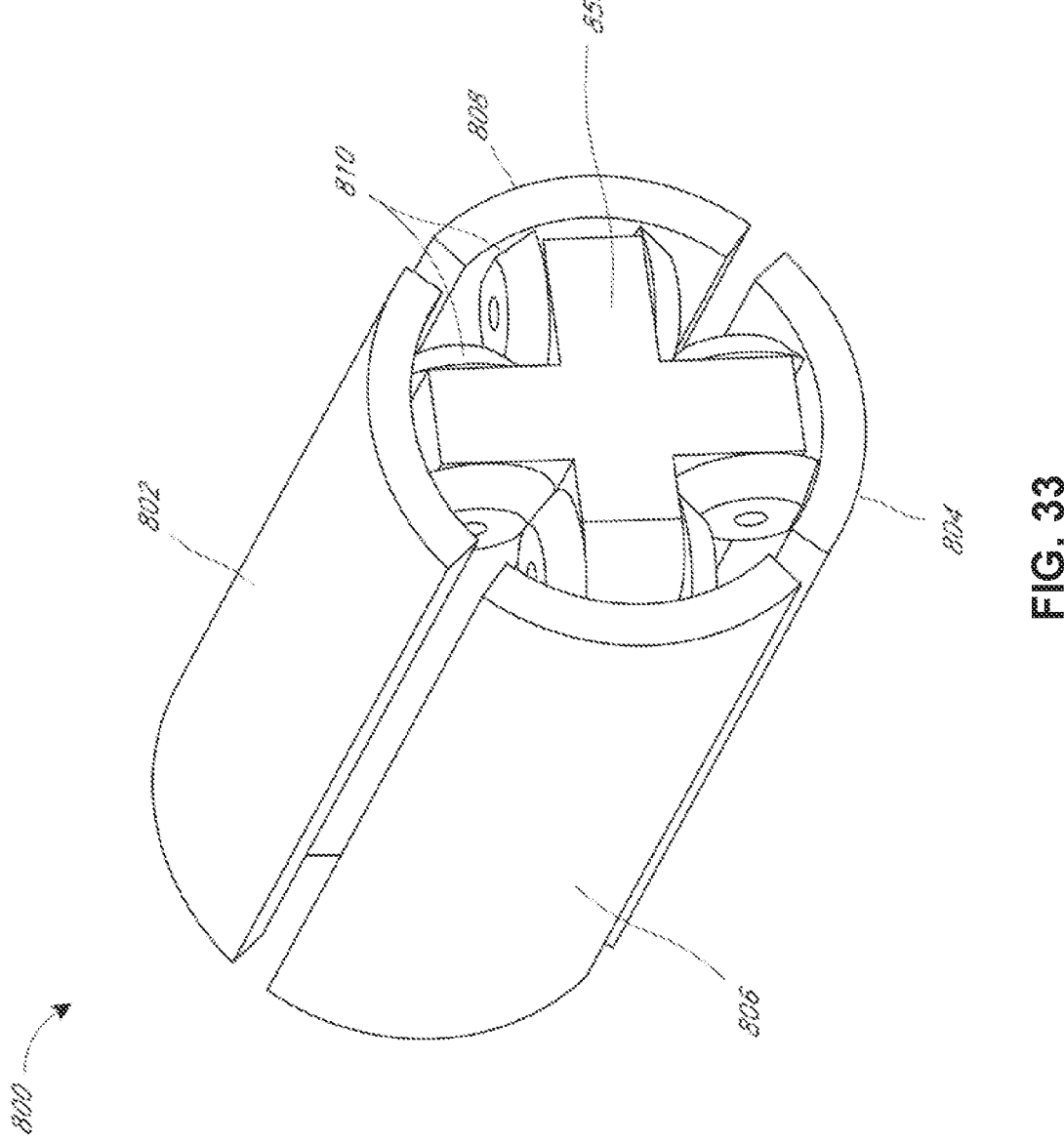
FIG. 33 illustrates yet another example of an input device.

FIG. 33 illustrates yet another example of a grasper 800. The grasper 800 can be similarly radially symmetric and have a plurality of links, such as four links 802, 804, 806, 808. Each of the plurality of links 802, 804, 806, 808 can have bevel gears 810 to connect the motion of each link 802, 804, 806, 808 to one another. The bevel gears 810 can be mounted on a central support member 850. Each of the plurality of links 202, 204, 206, 208 can include bevel gear teeth configured to connect motion of each of the plurality of links 202, 204, 206, 208 to the remainder of the plurality of links 202, 204, 206, 208.

D. Sensor Position

As described above, as the user maneuvers the plurality of links of the grasper, the user's fingers can adjust the angle of the plurality of links. The plurality of links can be oriented or angled relative to the central axis or central shaft. The plurality of links on the grasper can that measure the input angle of the user's fingers. For example, the angle at which any one or more of the plurality of links are positioned relative to the central shaft can be translated to the desired angle of a component of the instrument, such as one or more jaws of an end effector of the instrument. The grasper 200 can include one or more sensors to measure the angle of the plurality of links and thus the input angle of the user's fingers. Also described above, the secondary input state can also be measured by one or more sensors.

The grasper can include one or more sensors in various locations. In some configurations, one or more sensors can be located in or coupled to one or more of the plurality of links. In some configurations, one or more sensors can be located in or coupled to the central shaft. The one or more sensors in the central shaft can be advantageous in that there is limited space on each of the plurality of links. The one or more sensors in the central shaft can also advantageously position the sensor away from motion of the links and from contact by the user, which can reduce risk of damaging the sensor.

In some configurations, the one or more sensors can include a hall effect sensor, such as a 3D hall effect sensor. The one or more sensors can include 3 different sensors in orthogonal orientations to each other. Using these sensor readings, an algorithm can be developed to determine both the angle of the plurality of links and detect a secondary input state. The position of the one or more sensors in the central shaft can also advantageously remove the need to run wires and package sensors on the links.

The one or more sensors can detect one or more magnets included in the plurality of link and/or one or more magnets in a secondary input. For example, each link can include one or more magnets in fixed locations. As the plurality of links changes angles, the one or more sensors can be used to detect the change in magnetic field due to the motion of these magnets.

Similarly, the secondary input can include or be operatively connected to one or more magnets, such that change or movement in the secondary input can change the position or orientation of the one or more magnets, which can be detected by the sensor. In some examples, the change of the magnetic field due to the secondary input can be coupled with the motion of the grasper or with one or more components of the grasper. In some examples, the angle of the plurality of links can be decoupled from the secondary input state.

In some configurations, the one or more sensors can be a 3 degree of freedom sensor with physical electrical connections to the plurality of links and secondary inputs.

E. Grasper with Multiple Degrees-of-Freedom (DOFs)

Figure 34A:
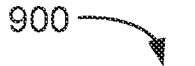
FIG. 34A illustrates a transverse view of an input device in accordance with some embodiments.

FIG. 34A illustrates a transverse view of a grasper 900 as an input device for controlling operation (e.g., movement, function) of a surgical tool. In some embodiments, the grasper 900 is similar to the link graspers shown in FIGS. 21A-21B, 22, 29B, 31, 32, and 33.

The grasper 900 includes a set of primary input objects. In some embodiments, the first set of one or more input objects includes a plurality of opposing links (e.g., a first pair of opposing links 902 and 904) with one or more finger pads (e.g., finger pads 912 and 914).

The grasper 900 also includes a set of secondary input objects (e.g., a second pair of opposing links 906 and 908, or rollers 946 and 948 located on the second pair of opposing links 906 and 908) that are distinct from the primary input objects. The set of secondary input objects may include, for example, a switch 306 as shown in FIGS. 26A-26B, a push button 256 (with or without a ledge or protrusion) as shown in FIGS. 27A-27B and 28, a rotary based device or a roller 446 or 946 as shown in FIGS. 29A-29D and 31, or a translating pad as shown in FIG. 30.

Although FIG. 34A shows two primary input objects (e.g., the first pair of opposing links 902 and 904) and two secondary input objects (e.g., rollers 946 and 948), the grasper 900 can include any number of primary input objects (e.g., finger pads) and any number of secondary input objects (e.g., finger clutches).

The primary input objects (e.g., the first pair of opposing links 902 and 904) are capable of receiving a first input (e.g., a user input of a first type) corresponding to a first function of the grasper 900 (e.g., a first function associated with operation of the surgical tool), such as an input corresponding to moving, maneuvering, or actuating a surgical tool coupled to the grasper. For example, the primary input objects may be configured to control opening and closing of the surgical tool.

The secondary input objects (e.g., the second pair of opposing links 906 and 908 or rollers 946 and 948) are capable of receiving a second input (e.g., a user input of a second type) corresponding to a second function of the grasper 900 (e.g., a second function associated with operation of the surgical tool). In some embodiments, the secondary input corresponds to a clutch input that decouples movement of a surgical tool from movement of the grasper (e.g., finger clutch operation). In such configurations, the secondary input objects are called finger clutches (e.g., rotary finger clutch, slidable finger clutch). The second input is distinct from (e.g., different from) the first input. For example, the first input may be a user action to apply pressure (e.g., pressing, clamping) at a finger pad (e.g., at any of the finger pads 912 and 914 or the opposing links 902 and 904), corresponding to activating or advancing a surgi-
cal tool coupled to a robotic arm while the second input may
correspond to a sliding motion or rotating motion at a finger
clutch (e.g., at any of the rollers 946 and 948 or the opposing
links 906 and 908) corresponding to decoupling movement
of the surgical tool from movement of the grasper 900. In
some embodiments, the secondary input can have alternative
functions besides or in addition to serving as a clutch input.
For example, the secondary input can also serve as a roller
to navigate a menu in a graphical overlay that may be
viewed by a surgeon.

In some embodiments, the primary input objects and the
secondary input objects are arranged radially around a
central shaft 950.

Additional details regarding the opposing links 902, 904,
906, and 908, the finger pads 912 and 914, and the rollers
946 and 948 are provided above with respect to FIGS.
21A-21B, 22, 24A-24B, and 25A-25B, and thus, are not
repeated herein.

The grasper 900 also includes a first set of one or more
magnets (e.g., magnets 922 and 924) that is associated with
the set of one or more primary input objects (e.g., the first
pair of opposing links 902 and 904). Inclusion of the first set
of magnets (e.g., magnets 922 and 924) allows detecting the
first input associated with the first function of the grasper
900, such as a function to activate or advance a surgical tool
coupled to a robotic arm, based on a magnetic field (e.g.,
using a Hall effect sensor).

The grasper 900 also includes a second set of one or more
magnets (e.g., magnets 926 and 928) that is associated with
the set of one or more secondary input objects (e.g., the
rollers 946 and 948). Inclusion of the second set of magnets
(e.g., magnets 926 and 928) allows detecting the second
input associated with the second function of the grasper 900,
such as a function to decouple movement of the grasper from
movement of a surgical tool coupled to a robotic arm, based
on the magnetic field (e.g., using a Hall effect sensor).

In addition, inclusion of both the first set of one or more
magnets (e.g., magnets 922 and 924) and the second set of
one or more magnets (e.g., magnets 926 and 928) allows
detecting and differentiating the first input and the second
input. The first set of one or more magnets and the second
set of one or more magnets are arranged in such a way so
that the magnetic field associated with the first input is
distinguishable from the magnetic field associated with the
second input, thereby providing multiple degrees-of-free-
dom in receiving inputs with the grasper 900. Additional
information regarding the position and orientation of the
magnets is provided with respect to FIGS. 34B-34C and
35A.

In FIG. 34A, the magnets 922, 924, 926, and 928 are
illustrated with a patterned fill for ease of reference. The
dark pattern fill corresponds to a first pole of the magnet and
the light pattern fill corresponds to a second pole of the
magnet that opposes the first pole (e.g., the north and south
poles of the magnet, or vice versa). Although FIG. 34A
shows that the first set of one or more magnets includes two
magnets 922 and 924, and the second set of one or more
magnets includes two magnets 926 and 928, each of the first
set one or more magnets and the second set of one or more
magnets may include any number of magnets (e.g., 3, 4, 5,
6, or more).

The grasper 900 also includes a Hall effect sensor 930 for
detecting a magnetic field that is based on (e.g., generated
due to the presence of, generated based on the position of)
the first set of one or more magnets (e.g., magnets 922 and
924) and the second set of one or more magnets (e.g., magnets 926 and 928). For example, the Hall effect sensor
930 may be positioned between (e.g., disposed between)
magnets 922 and 924, and thus, can determine a distance
between magnets 922 and 924. In another example, the Hall
effect sensor 930 may be able to determine a relative angle
(e.g., rotation) of magnet 926 and/or 928 relative to the Hall
effect sensor 930. In some embodiments, the Hall effect
sensor 930 is positioned inside the central shaft 950 as
shown in FIG. 34A, on the central shaft 950, or adjacent to
the central shaft 950.

Figure 34B:
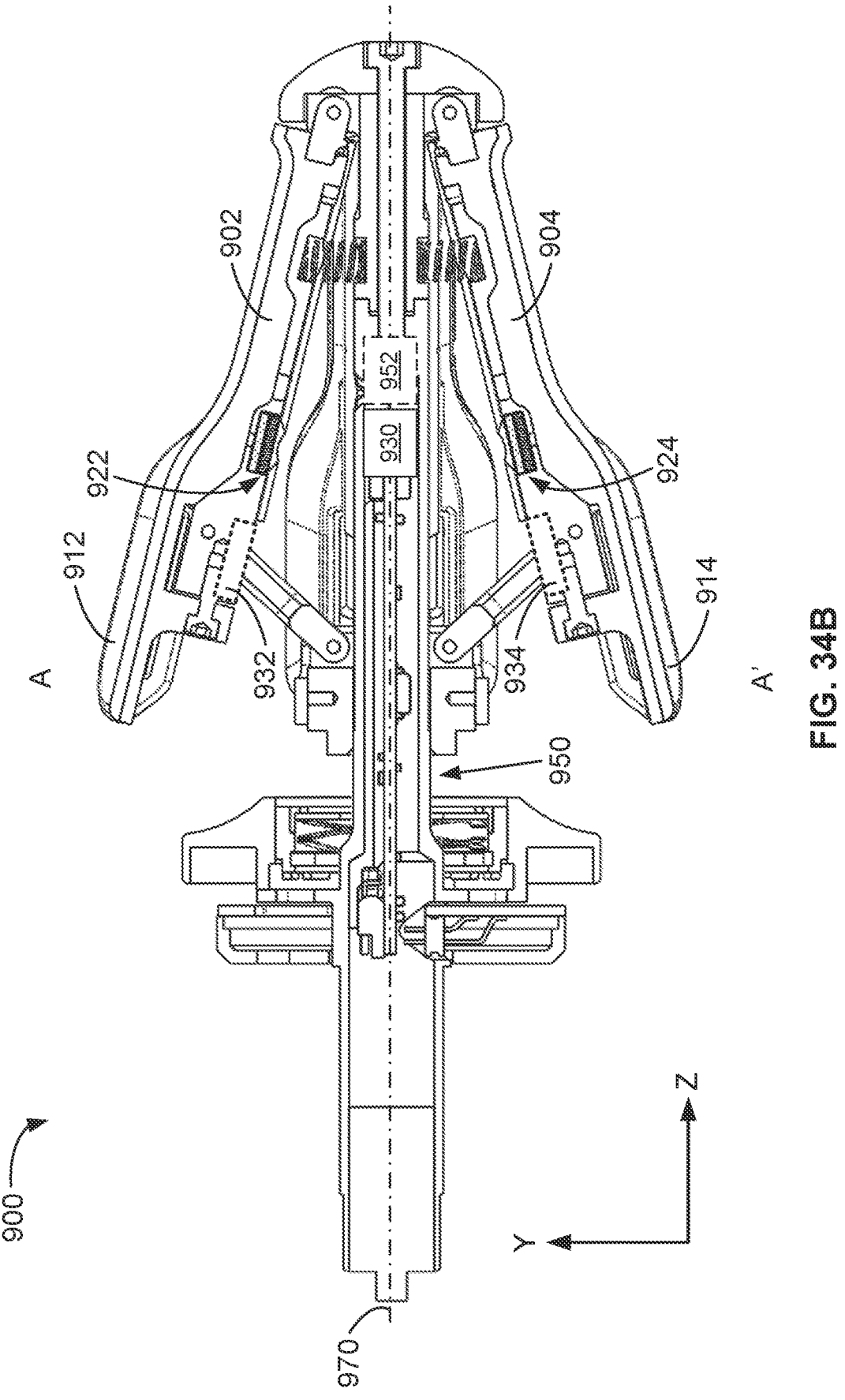
FIG. 34B illustrates a cross-sectional view of the input device of FIG. 34A.

FIG. 34B illustrates a cross-sectional view of the grasper
900 taken along the line AA' shown in FIG. 34A. Each of the
finger pads 912 and 914 is associated with at least one
magnet of the first set of one or more magnets (e.g., at least
one magnet is positioned on a same link associated with the
finger pad). For example, in FIG. 34A, the magnet 922 of the
first set of one or more magnets is associated with the finger
pad 912 and a second magnet 924 of the first set of one or
more magnets is associated with the finger pad 914. In some
embodiments, the magnet 922 is non-rotatably coupled with
a primary input object (e.g., the link 902). The magnet 924
is non-rotatably coupled with a primary input object (e.g.,
the link 904). In such embodiments, the magnet 922 forms
a fixed angle and cannot be rotated relative to the link 902,
and the magnet 924 forms a fixed angle and cannot be
rotated relative to the link 904.

Each of the magnets 922 and 924 has a first pole and a
second pole that is opposite of the first pole (e.g., north pole
and south pole). In FIG. 34B, the first pole is illustrated with
a dark pattern fill and the second pole is illustrated with a
light pattern fill for ease of reference. In some embodiments,
the magnets 922 and 924 are positioned and oriented relative
to each other such that a magnetic dipole moment (e.g.,
magnetic axis, pointing from a south pole of a magnet to a
north pole of the magnet) of the magnet 922 is substantially
parallel to a magnetic dipole moment (e.g., magnetic axis,
pointing from a south pole to a north pole of the magnet) of
the magnet 924. For example, when the opposing links 902
and 904 are in a closed position (such that the links 902 and
904 are substantially parallel to the central shaft 950), the
magnetic dipole moments of the magnet 922 and 924 are
substantially parallel to each other such that the magnet 922
has a magnetic dipole moment that points in a first direction
along the y-axis, and the magnet 924 has a magnetic dipole
that points in a second direction (e.g., substantially opposite
to the first direction) along the y-axis, where the first
direction and the second direction are substantially parallel
to each other.

In some embodiments, as shown in FIG. 34B, a first pole
of the magnet 922 faces (e.g., substantially faces) a second
pole of the magnet 924 such that the second pole of the
magnet 924 is disposed between the first pole of the magnet
922 and a first pole of the magnet 924. In some embodi-
ments, a distance between the first pole of the magnet 922
and the second pole of the magnet 924 is smaller than a
distance between the second pole of the magnet 922 and the
second pole of the magnet 924). In addition, FIG. 34B also
shows that the second pole of the magnet 924 faces (e.g.,
substantially faces) the first pole of the magnet 922 such that
the first pole of the magnet 922 is disposed between a second
pole of the magnet 922 and the second pole of the magnet
924. In some embodiments, a distance between the first pole
of the magnet 922 and the second pole of the magnet 924 is
smaller than a distance between the second pole of the
magnet 922 and the second pole of the magnet 924.

In some embodiments, the magnets 922 and 924 are positioned at opposite sides of a central axis 970 of the grasper 900.

In some embodiments, a finger pad is associated with two or more magnets. For example, the finger pad 912 may be associated with the magnet 922 and an additional magnet 932 (e.g., a redundant magnet) that is distinct from the magnet 922 and distinct from the magnet 924. Even if the magnet 922 associated with the finger pad 912 is displaced (e.g., falls out or is moved to a different location) or becomes de-magnetized, the position or movement of the finger pad 912 may be determined using the additional magnet 932. Similarly, the finger pad 914 may be associated with the magnet 924 and an additional magnet 934 that is distinct from the magnet 922 and the magnet 924.

FIG. 34B also shows the Hall effect sensor 930. In some embodiments, the Hall effect sensor 930 is located on the central axis 970 of the grasper 900 as shown in FIG. 34B.

In some embodiments, the grasper 900 also includes a second Hall effect sensor 952 (e.g., a redundant Hall effect sensor, a safety Hall effect sensor) that is distinct from the Hall effect sensor 930. The second Hall effect sensor 952 is configured to detect a magnetic field that is based on (e.g., generated due to the presence of, generated due to the position of) the first set of one or more magnets (e.g., magnets 922 and 924) and the second set of one or more magnets (e.g., magnets 926 and 928). In some embodiments, the second Hall effect sensor 952 is provided as a safety feature. In such cases, the Hall effect sensor 930 and the second Hall effect sensor 952 form a pair of Hall effect sensors that can be used for fault detection. For example, a magnetic field (e.g., magnetic field strength, magnetic flux) detected by the Hall effect sensor 930 is compared to a magnetic field (e.g., magnetic field strength, magnetic flux) detected by the second Hall effect sensor 952. In accordance with a determination that the magnetic field detected by the Hall effect sensor 930 is distinct from (e.g., different from, having a magnitude along at least one direction that is different from) the magnetic field detected by the second Hall effect sensor 952, the grasper 900 or a medical system 36 that includes the grasper 900 provides a fault signal to indicate an error, or halts movement of a robotic arm.

Figure 34C:
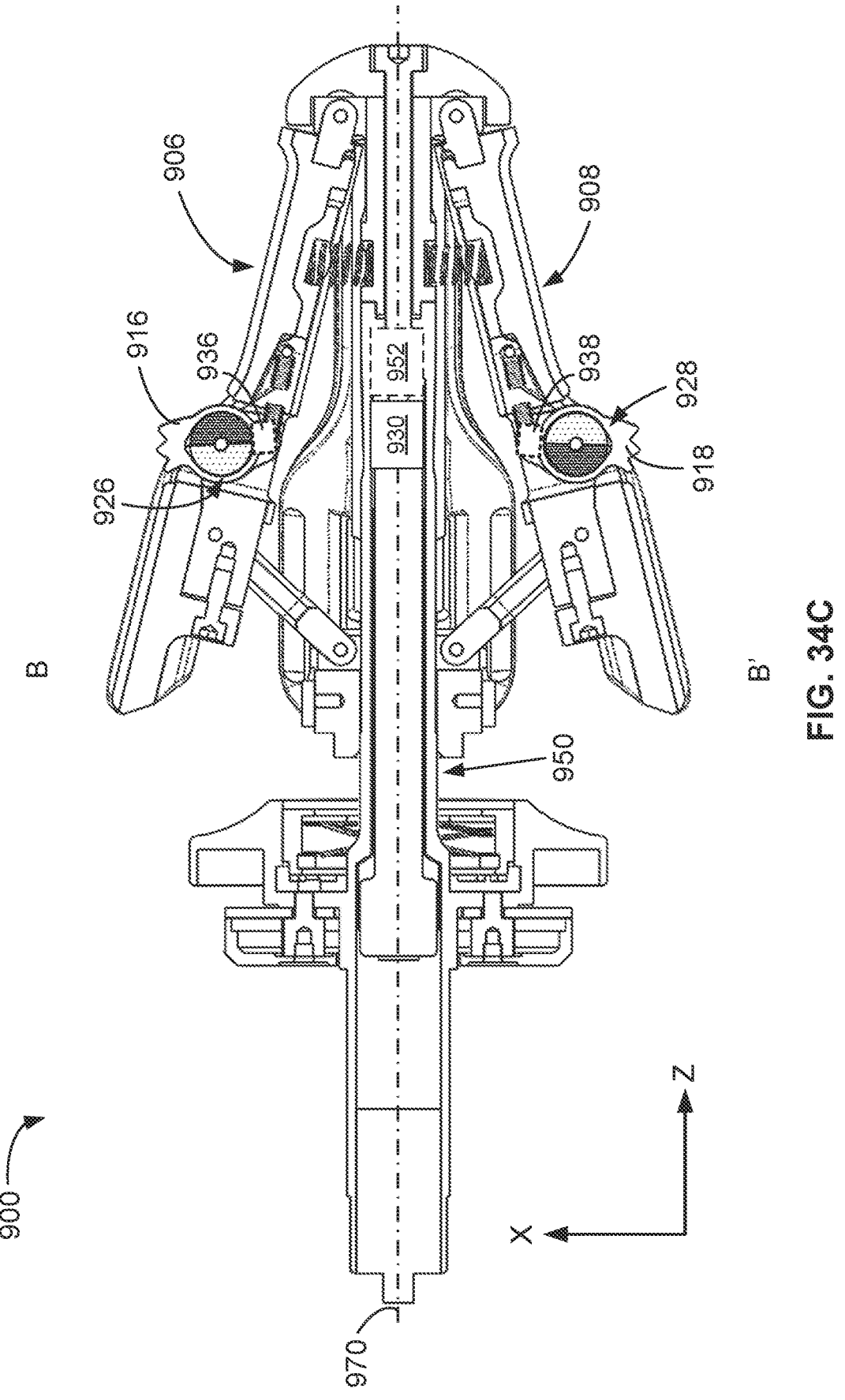
FIG. 34C illustrates another cross-sectional view of the input device of FIG. 34A.

FIG. 34C illustrates a cross-sectional view of the grasper 900 taken along the line BB' shown in FIG. 34A. Each of the rollers 946 and 948 is associated with at least one magnet of the second set of one or more magnets. FIG. 34A shows that a first magnet 926 of the second set of one or more magnets is associated with the roller 946 and a second magnet 928 of the second set of one or more magnets is associated with the roller 948. The magnet 926 is non-rotatably coupled with the roller 946 and is rotatably coupled with the link 906 so that the rotation of the roller 946 causes rotation of the magnet 926 relative to the link 906 (and relative view to an axis of the grasper 900). Thus, when a user input is received at the roller 946, the relative orientation of the magnet 926 is changed relative to the link 906. Similarly, the magnet 928 is non-rotatably coupled to the roller 948 and rotatably coupled with the link 908 such that the rotation of the roller 948 causes rotation of the magnet 928 relative to the link 908.

Each of the magnets 926 and 928 has a first pole corresponding to a first magnetic polarization and a second pole corresponding to a second magnetic polarization that that is opposite to the first magnetic polarization (e.g., north pole and south pole). FIG. 34C shows the first pole in a dark pattern fill and the second pole in a light pattern fill for ease of reference. The magnets 926 and 928 are positioned and oriented relative to each other such that a magnetic dipole moment (e.g., magnetic axis, pointing from a south pole of a magnet to a north pole of the magnet) of the magnet 926 is substantially parallel to a magnetic dipole moment (e.g., magnetic axis, pointing from a south pole of a magnet to a north pole of the magnet) of the magnet 928. For example, the magnet 926 has a magnetic dipole moment that points in a first direction along the z-axis, and the magnet 928 has a magnetic dipole moment that points in a second direction (e.g., substantially opposite to the first direction) along the z-axis.

In some embodiments, a finger clutch is associated with two or more magnets. For example, the roller 946 may be associated with the magnet 926 and an additional magnet 936 (e.g., a redundant magnet) that is distinct from the magnet 926 and distinct from the magnet 928 such that if one of the magnets associated with the roller 946 is displaced (e.g., falls out or is moved to a different position) or becomes de-magnetized, the orientation or movement of the roller 946 may be determined using the additional magnet 936. Similarly, the roller 948 may be associated with the magnet 928 and an additional magnet 938 (e.g., a redundant magnet) that is distinct from the magnet 926 and distinct from the magnet 928.

Figure 35A:
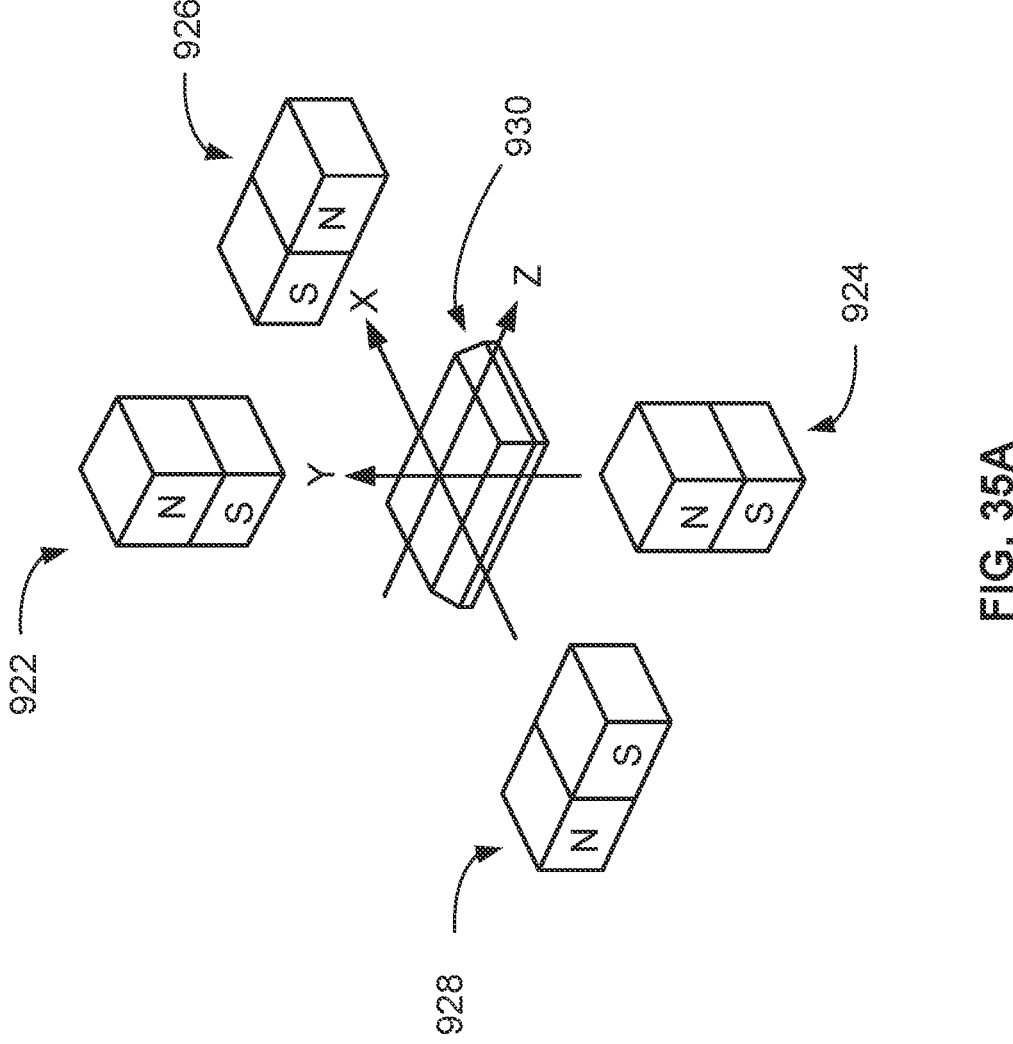
FIG. 35A illustrates positions of magnets in the input device of FIG. 34A.

FIG. 35A illustrates the positions (e.g., relative positions and orientations) of magnets in the grasper 900. The first and second poles (e.g., north and south poles) of each of the magnets 922, 924, 926, and 928 shown in FIG. 35A are denoted with "N" for the north pole and "S" for the south pole.

Magnets 922 and 924 of the first set of one or more magnets are disposed along the a first axis (e.g., y-axis) such that the first axis extends between the magnets 922 and 924. The magnetic dipole moment (e.g., magnetic axis) of the magnet 922 is substantially parallel to the first axis (e.g., y-axis), and the magnetic dipole moment (e.g., magnetic axis) of the magnet 924 is also substantially parallel to the axis (e.g., y-axis).

Magnets 926 and 928 of the second set of one or more magnets are disposed along the a second axis (e.g., x-axis) that extends between the magnets 926 and 928. The second axis (e.g., x-axis) is substantially orthogonal to (e.g., intersecting perpendicular or skew perpendicular, forming an angle between 85 and 95 degrees, between 80 and 100 degrees, between 75 and 105 degrees, etc.) the first axis (e.g., the y-axis). The magnetic dipole moment (e.g., magnetic axis) of the magnet 926 (e.g., extending along the z-axis) is non-parallel (e.g., substantially orthogonal, substantially perpendicular) to the second axis (e.g., x-axis), and the magnetic dipole moment (e.g., magnetic axis) of the magnet 929 (e.g., extending along the z-axis) is also non-parallel (e.g., substantially orthogonal, substantially perpendicular) to the second axis (e.g., x-axis).

FIG. 35A also shows that a Hall effect sensor 930 of the grasper 900 is positioned between the magnets 922 and 924 of the first set of one or more magnets, and between the magnets 926 and 928 of the second set of one or more magnets. In some embodiments, as shown in FIG. 34A, the Hall effect sensor 930 is positioned adjacent to (e.g., on) a central shaft 950 of the grasper 900. In some embodiments, the Hall effect sensor 930 is a three-dimensional (3D) Hall effect sensor that includes a plurality of sub-sensors (e.g., a group of two or more Hall effect sensors) and can determine (e.g., detect) the magnitude of a magnetic field in a plurality of directions. For example, a 3D Hall effect sensor may include a first sub-sensor configured for detecting a magnetic field (e.g., magnetic field strength, magnetic flux) in a first direction (e.g., x-direction, a direction along the x-axis), a second sub-sensor configured for detecting a magnetic field (e.g., magnetic field strength, magnetic flux) in a second direction (e.g., y-direction, a direction along the y-axis) that is distinct from the first direction (e.g., orthogonal to the first direction, perpendicular to the first direction), and a third sub-sensor configured for detecting a magnetic field (e.g., magnetic field strength, magnetic flux) in a third direction (e.g., z-direction, a direction along the z-axis) that is distinct from each of the first direction and the second direction (e.g., orthogonal to each of the first direction and the second direction, perpendicular to each of the first direction and the second direction). Due to the ability of the 3D Hall effect sensor to detect the magnetic field (e.g., magnetic field strength, magnetic flux) in a plurality of directions, the 3D Hall effect sensor may be used to detect magnetic field distortions that may arise due to insertion or presence of ferrous or metallic objects in the magnetic field. In addition, sensitivity of the 3D Hall effect sensor to magnetic distortions (e.g., a determination that a magnetic field strength or magnetic flux is outside of a range of expectation) in a plurality of directions (e.g., three different directions, such as in the x-, y-, and z-directions) may be used to compensate for the magnetic field distortions so that accurate determination of the positions, orientations, or movements of input objects associated with magnets. For example, a magnetic field intensity that is outside a pre-defined range in any direction may be used as an indicator of an invalid input, which may, in turn, halt movement of a surgical tool (e.g., dislocation of a magnet or demagnetization of a magnet can be detected by the 3D Hall effect sensor to halt movement of a surgical tool). In some embodiments, the magnetic field intensity in a particular direction is adjusted based on the magnetic field intensities in other directions to compensate for the magnetic field distortion.

Thus, the use of 3D Hall effect sensor in an input device (e.g., grasper 900) can further improve the accuracy in determining the positions of input objects.

The primary input objects (e.g., finger pads 912 and 914) that are associated with (e.g., coupled to) the magnets 922 and 924, and are configured to receive input (e.g., a user input of a first type) that has movement primarily in a longitudinal direction (e.g., along the y-direction, such as pressing or pushing the finger pads 912 and 914 so that the opposing links 902 and 904 are in a closed position). Thus, the magnets 922 and 924 are positioned at locations so that the Hall effect sensor 930 can detect a longitudinal component of the magnetic field generated from the magnets 922 and 924 in response to input at the primary input objects (e.g., finger pads 912 and 914). For example, when an input corresponding to closing or opening the opposing links 902 and 904 is received at any of the finger pads 912 and 914, a distance between the Hall effect sensor 930 and each of the magnets 922 and 924, as well as a distance between the magnets 922 and 924, is changed as the opposing links 902 and 904 (and the finger pads 912 and 914) are moved closer to one another or further apart. A change in the distance between the Hall effect sensor 930 and a magnet (e.g., magnet 922 or 924) and a change in the distance between the magnets 922 and 924 correspond to (e.g., lead to, result in) a change in the magnetic field strength (e.g., magnetic flux) along the longitudinal direction, which is detected by the Hall effect sensor 930.

In contrast to movement of the finger pads 912 and 914, the secondary input objects (e.g., rollers 946 and 948) that are associated with (e.g., coupled to) the magnets 926 and 928 are configured to receive input (e.g., user input of a second type) that has movement in a transverse direction (e.g., rotating or sliding the finger clutch on the x-z plane). Thus, the magnets 926 and 924 are positioned at locations so that the Hall effect sensor 930 can detect a transverse component of the magnetic field generated from the magnets 926 and 928 in response to input(s) at the finger clutches. For example, when an input such as rotation or sliding of the finger clutch is received at any of the rollers 946 and 948, a relative angle formed by the Hall effect sensor 930 and the magnet 926 or the magnet 928 is changed as one or more of the finger clutches are rotated or slid. A change in the orientation of the magnet 926 or 928 relative to the Hall effect sensor 930 corresponds to (e.g., lead to, result in) a change in the magnetic field strength (e.g., magnetic flux) along the transverse direction, which is detected by the Hall effect sensor 930.

Placing the first set of one or more magnets (e.g., magnets 922 and 924) that correspond to input(s) received at the primary input objects in an orientation that is orthogonal to an orientation of the second set of one or more magnets (e.g., magnets 926 and 928) that correspond to input(s) received at the secondary input objects reduces the interaction (e.g., interference) between the magnetic flux changes associated with the different types of inputs (e.g., input(s) of a first type at the primary input objects, and input(s) of a second type at the secondary input objects) that can be received at the grasper 900.

Figure 35B:
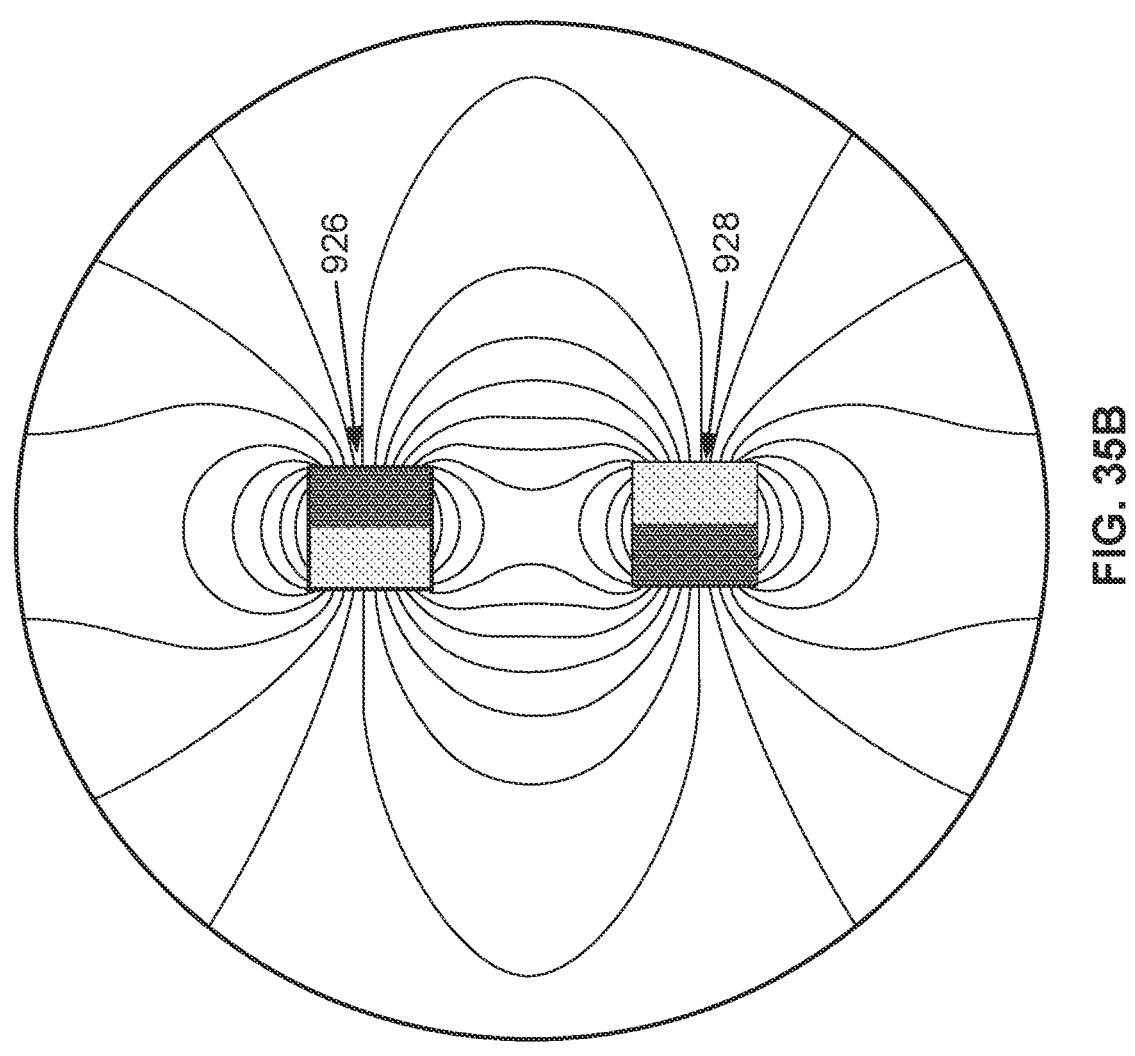
FIG. 35B illustrates magnetic field distribution between two magnets in the input device of FIG. 34A.

FIG. 35B illustrates magnetic field distribution associated with magnets 926 and 928 of the grasper 900. In FIG. 35B, a dark fill pattern is used to illustrate a first magnetic pole of a magnet and a light fill pattern is used to illustrate a second magnetic pole of a magnet. As shown, the magnet 926 is oriented in an opposite direction relative to the magnet 928 such that a magnetic dipole moment of the magnet 926 (e.g., pointing from the south pole of the magnet 926 to the north pole of the magnet 926) points in a direction that is substantially opposite (e.g., forms an angle between 160°-200°) to a direction of a magnetic dipole moment of the magnet 928 (e.g., pointing from the south pole of the magnet 928 to the north pole of the magnet 928). The "opposite" orientation of the magnets 926 and 928 provide the magnetic distribution as shown by the magnetic field lines in FIG. 35B. As shown, the magnetic distribution (e.g., distribution of magnetic flux) between the two magnets 926 and 928 do not include in "blind spots" or "eyes" where two poles having a same magnetic polarization repel each other (and the magnetic flux in the "blind spot" is substantially zero), which improves the accuracy in determining positions of magnets.

Figure 35C:
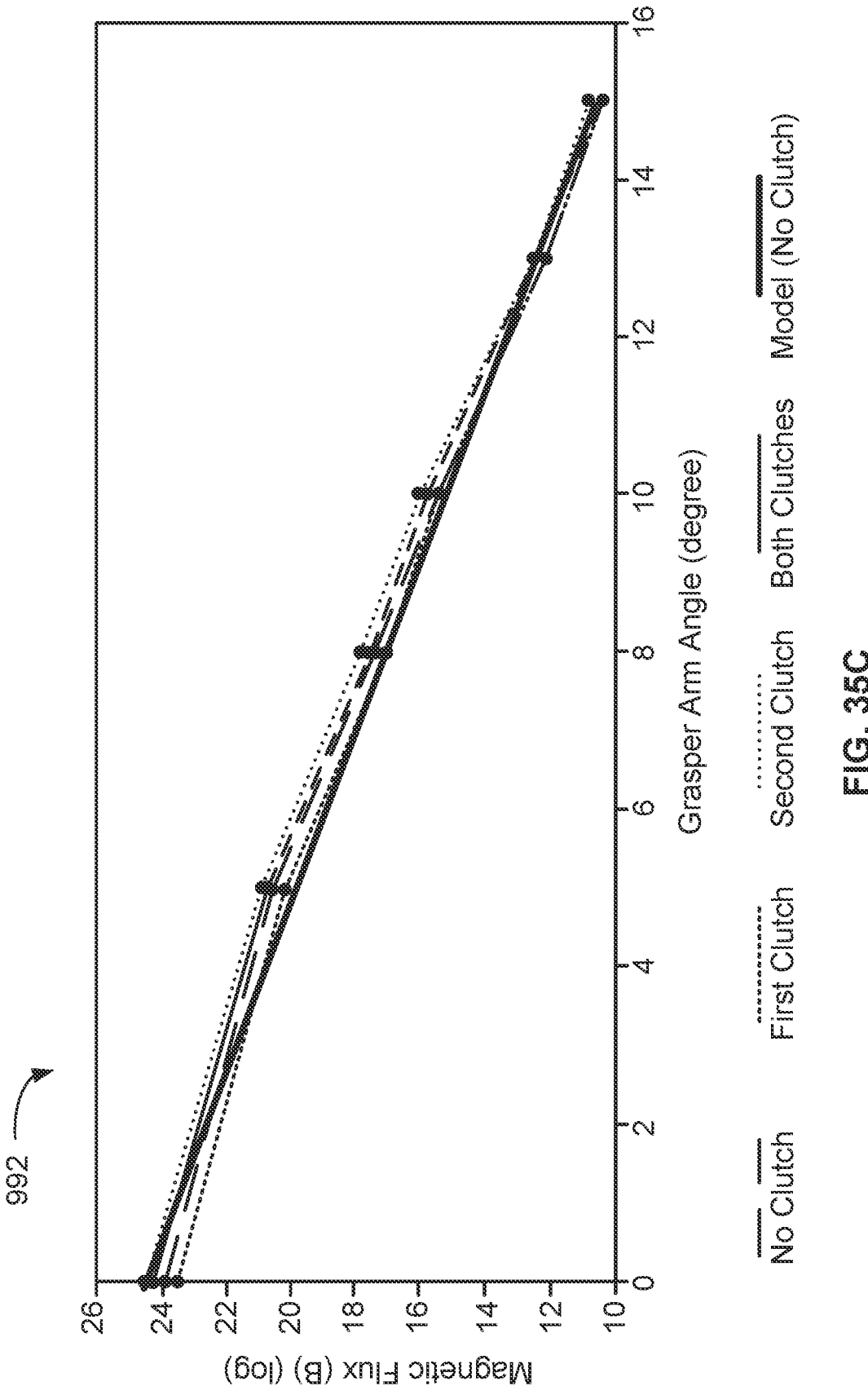
FIG. 35C illustrates a magnetic flux detected by the input device in response to receiving a user input.

FIG. 35C illustrates a logarithmic graph 992 that shows the magnetic flux magnetic flux (Bz) detected by a Hall effect sensor 930 (such as a 3D Hall effect sensor) of the grasper 900 as a function of a grasper arm angle (e.g., an angle formed by a link 902 or 904 relative to the central axis 970). The grasper arm angle may be set in response to receiving a user input of a first type at any of the primary input objects (e.g., finger pads 912 and 914).

The long dashed lines indicates the magnetic flux (B) (e.g., longitudinal component of the magnetic field) detected by the Hall effect sensor 930 when no input is provided on the rollers 946 and 948 so that the magnets 926 and 928 do not change their orientations. The dotted line and the short dashed line indicate the magnetic flux (B) detected by the Hall effect sensor 930 when an input is provided on only one of the roller 946 or 948 so that only one of the magnets 926 or 928 changes its orientation. The thin solid line indicates the magnetic flux (B) detected by the Hall effect sensor 930 when user inputs are provided on both rollers 946 and 948 so that the magnets 926 and 928 have changed their orientations. The thick solid line indicates the expected magnetic flux (B) to be detected by the Hall effect sensor 930 as a function of the grasper arm angle.

The graph 992 illustrates the grasper arm angle can be determined based on the magnetic flux detected by the Hall effect sensor 930. In addition, the graph 992 also shows that the magnetic flux detected by the Hall effect sensor 930 (in a direction for determining the grasper arm angle, such as along the y-axis) is not significantly affected by the orientations of the magnets 926 and 928. Thus, the position and orientation of the first set of one or more magnets (e.g., magnets 922 and 924) and the position and orientation of the second set of one or more magnets (e.g., magnets 926 and 928) as described above with respect to FIGS. 34A-34C and 35A provide a configuration in which a Hall effect sensor 930 of the grasper 900 is able to separately detect (e.g., decouple, separately identify, separately determine) input(s) received at the primary input objects (e.g., finger pads 912 and 914) from input(s) received at the secondary input objects (e.g., rollers 946 and 948). As a result, input(s) (e.g., inputs of the first type) received at any of the primary input objects (e.g., finger pads 912 and 914) are determined independently from input(s) (e.g., inputs of the second type) received at any of the secondary input objects (e.g., rollers 946 and 948).

As described herein, the grasper 900 may be used as an input device in a medical system for controlling a surgical tool. Thus, in accordance with some embodiments, a medical system includes a surgical tool and an input device (e.g., the grasper 900). The input device includes a first set of one or more input objects (e.g., opposing links that include finger pads) for receiving an input of a first type associated with the operation of the surgical tool, and a second set of one or more input objects (e.g., finger clutch) for receiving an input of a second type associated with the operation of the surgical tool. The second set of one or more input objects is distinct from the first set of one or more input objects object. The input device also includes a first Hall effect sensor for detecting a magnetic field based on the first set of one or more magnets and the second set of one or more magnets.

3. Implementing Systems and Terminology

Figure 36:
FIG. 36 is a schematic diagram illustrating electronic components of a medical system that includes the input device of FIG. 34A.

FIG. 36 is a schematic diagram illustrating electronic components of a medical system 36 that includes a grasper (e.g., grasper 900) for operating a surgical tool.

The medical system 36 includes one or more processors 280, which are in communication with a computer readable storage medium 282 (e.g., computer memory devices, such as random-access memory, read-only memory, static random-access memory, and non-volatile memory, and other storage devices, such as a hard drive, an optical disk, a magnetic tape recording, or any combination thereof) storing instructions for performing any methods described herein (e.g., operations described with respect to FIG. 37). In some embodiments, the one or more processors 280 are also in communication with an input/output controller 284 (via a system bus or any electrical circuit). The input/output controller 284 receives instructions and/or data from an input device (e.g., a user input device 286 that corresponds to an input device such as grasper 900) and relays the received instructions and/or data to the one or more processors 280 (e.g., with or without any translation, conversion, and/or data processing). For example, the controller 284 may receive sensor output(s) from the one or more sensors 287 (e.g., a sensor corresponding to Hall effect sensor, including a 3D Hall effect sensor, Hall effect sensor 930 and/or any additional Hall effect sensors of the grasper 900, such as the second Hall effect sensor 952) and relay the information to the one or more processors 280. The input/output controller 284 also receives instructions and/or data from the one or more processors 280 (e.g., based on the data from the sensor(s) 287 of the input device 286) and relays the instructions and/or data to one or more motors 292, such as first motors 292-1 and 292-2 that are part of a motor driver network 290. In some embodiments, the instructions and/or data from the input device 286 are directly transmitted to the one or more processors 280. In some embodiments, the instructions and/or data from the one or more processors 280 are directly transmitted to the motors 292 of the motor driver network 290.

The computer readable storage medium 282 stores storing instructions for execution by the one or more processors. In some embodiments, the stored instructions include instructions for providing a fault signal in accordance with a determination that the magnetic field detected by the first Hall effect sensor 930 is distinct from (e.g., different from, has a magnitude and/or direction that is different from) the magnetic field detected by the second Hall effect sensor 952. In some embodiments, the fault signal is provided to the motor driver network 290 for halting movement of motors, such as motors 292-1 and 292-2.

FIG. 37 is a flowchart illustrating a method 370 for operating a surgical tool via the input device (e.g., grasper 900 shown in FIG. 34A). In accordance with some embodiments, the method 370 is performed by one or more processors 280 executing instructions stored in the memory 282. The method 370 includes detecting (310) a magnetic field with a Hall effect sensor 390 (e.g., a first Hall effect sensor, a 3D Hall effect sensor). The magnetic field is based on a first set of one or more magnets (e.g., magnets 922 and 924) that are associated with a first set of one or more input objects (e.g., finger pads 912 and 914) and a second set of one or more magnets (e.g., magnets 926 and 928) that are associated with a second set of one or more input objects (e.g., rollers 946 and 948). The method also includes determining (320) a position (or a movement) of the first set of one or more input objects (e.g., movement of the finger pads 912, 914 or the grasper arm angles for the links 902 and 904) based on the magnetic field detected by the Hall effect sensor 930, and determining (330) a position (or a movement) of the second set of one or more input objects (e.g., movement of the secondary input objects 946, 948) based on the magnetic field detected by the Hall effect sensor.

In some embodiments, the position (or the movement) of the first set of one or more input objects (e.g., movement of the finger pads 912, 914) is determined (340) separately from the position (or the movement) of the second set of one or more input objects (e.g., movement of the finger clutches 946, 948). In some embodiments, the position (or the movement) of the first set of one or more input objects (e.g., movement of the finger pads 912, 914) is determined (340) concurrently with determining the position (or the movement) of the second set of one or more input objects (e.g., movement of the finger clutches 946, 948).

In some embodiments, the position (or the movement) of the first set of one or more input objects (e.g., movement of the finger pads 912, 914) is determined (340) independently from the position (or the movement) of the second set of one or more input objects (e.g., movement of the finger clutches 946 and 948).

Implementations disclosed herein provide systems, methods and apparatus for controllers for robotic surgical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims. For example, in some cases, the position of the first set of one or more input objects is determined (320) before the position of the second set of one or more input objects is determined. In some other cases, the position of the first set of one or more input objects is determined (320) after the position of the second set of one or more input objects is determined. In yet some other cases, the position of the first set of one or more input objects is determined (320) concurrently with the position of the second set of one or more input objects.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. An input device for controlling an operation of a surgical tool, the input device comprising:
   a first set of one or more input objects for receiving an input of a first type associated with the operation of the surgical tool;
   a second set of one or more input objects, distinct from the first set of one or more input objects, for receiving an input of a second type associated with the operation of the surgical tool;
   a first set of one or more magnets associated with the first set of one or more input objects;
   a second set of one or more magnets associated with the second set of one or more input objects; and
   a first Hall effect sensor for detecting a magnetic field based on the first set of one or more magnets and the second set of one or more magnets,
   wherein:
      the first set of one or more input objects comprises a plurality of opposing links with one or more finger pads, or
      the second set of one or more input objects comprises a finger clutch.

2. The input device of claim 1, wherein the first set of one or more input objects comprises the plurality of opposing links with one or more finger pads.

3. The input device of claim 2, wherein:
   the plurality of opposing links is configured to control opening and closing of the surgical tool.

4. The input device of claim 1, wherein the second set of one or more input objects comprises the finger clutch.

5. The input device of claim 1, further comprising:
   a second Hall effect sensor distinct from the first Hall effect sensor for detecting a magnetic field based on the first set of one or more magnets and the second set of one or more magnets;
   one or more processors; and
   memory storing instructions for execution by the one or more processors, the stored instructions including instructions for, in accordance with a determination that the magnetic field detected by the first Hall effect sensor is distinct from the magnetic field detected by the second Hall effect sensor, providing a fault signal.

6. The input device of claim 1, wherein the first Hall effect sensor is a three-dimensional Hall effect sensor.

7. The input device of claim 6, further comprising:
   a central shaft,
   wherein the three-dimensional Hall effect sensor is positioned adjacent to a central shaft of the input device.

8. The input device of claim 6, wherein the three-dimensional Hall effect sensor includes:
   a first sub-sensor positioned for detecting a magnetic field in a first direction;
   a second sub-sensor positioned for detecting a magnetic field in a second direction; and
   a third sub-sensor positioned for detecting a magnetic field in a third direction, wherein the first direction, the second direction, and the third direction are distinct from one another.

9. A medical system, comprising:

a surgical tool; and the input device of claim 1 for operating the surgical tool.

10. A medical system, comprising:

the input device of claim 1 for operating a surgical tool;

one or more processors; and memory storing one or more instructions, the stored instructions including instructions for:

determining a movement of the first set of one or more input objects based on the magnetic field detected by the first Hall effect sensor; and determining a movement of the second set of one or more input objects based on the magnetic field detected by the first Hall effect sensor.

11. A method for operating a surgical tool, the method comprising:

at one or more processors executing instructions stored in memory:

detecting, with a Hall effect sensor, a magnetic field based on a first set of one or more magnets associated with a first set of one or more input objects and a second set of one or more magnets associated with a second set of one or more input objects, the first set of one or more input objects comprising a plurality of opposing links with one or more finger pads;

determining a position of the first set of one or more input objects based on the magnetic field detected by the Hall effect sensor; and determining a position of the second set of one or more input objects based on the magnetic field detected by the Hall effect sensor.

12. The method of claim 11, wherein:

the position of the first set of one or more input objects is determined separately from the position of the second set of one or more input objects.

13. An input device for controlling an operation of a surgical tool, the input device comprising:

a first set of one or more input objects for receiving an input of a first type associated with the operation of the surgical tool;

a second set of one or more input objects, distinct from the first set of one or more input objects, for receiving an input of a second type associated with the operation of the surgical tool;

a first set of one or more magnets associated with the first set of one or more input objects;

a second set of one or more magnets associated with the second set of one or more input objects;

a first Hall effect sensor for detecting a magnetic field based on the first set of one or more magnets and the second set of one or more magnets; and a second Hall effect sensor distinct from the first Hall effect sensor for detecting a magnetic field based on the first set of one or more magnets and the second set of one or more magnets.

14. An input device for controlling an operation of a surgical tool, the input device comprising:

a first set of one or more input objects for receiving an input of a first type associated with the operation of the surgical tool;

a second set of one or more input objects, distinct from the first set of one or more input objects, for receiving an input of a second type associated with the operation of the surgical tool;

a first set of one or more magnets associated with the first set of one or more input objects, the first set of one or more magnets including a first magnet and a second magnet;

a second set of one or more magnets associated with the second set of one or more input objects; and a Hall effect sensor for detecting a magnetic field based on the first set of one or more magnets and the second set of one or more magnets, wherein:

the first magnet and the second magnet are positioned such that a first pole of the first magnet and an opposing pole of the second magnet substantially face toward each other, or a magnetic axis of the first magnet is substantially parallel to an axis extending between the first magnet and the second magnet.

15. The input device of claim 14, wherein the first magnet and the second magnet are positioned such that the first pole of the first magnet and the opposing pole of the second magnet substantially face toward each other.

16. The input device of claim 14, wherein the magnetic axis of the first magnet is substantially parallel to the axis extending between the first magnet and the second magnet.

17. An input device for controlling an operation of a surgical tool, the input device comprising:

a first set of one or more input objects for receiving an input of a first type associated with the operation of the surgical tool, the first set of one or more input objects including a first input object and a second input object;

a second set of one or more input objects, distinct from the first set of one or more input objects, for receiving an input of a second type associated with the operation of the surgical tool;

a first set of one or more magnets associated with the first set of one or more input objects, the first set of one or more magnets including a first magnet and a second magnet where the first magnet is non-rotatably coupled with the first input object and the second magnet is non-rotatably coupled with the second input object;

a second set of one or more magnets associated with the second set of one or more input objects; and a Hall effect sensor for detecting a magnetic field based on the first set of one or more magnets and the second set of one or more magnets.

18. An input device for controlling an operation of a surgical tool, the input device comprising:

a first set of one or more input objects for receiving an input of a first type associated with the operation of the surgical tool;

a second set of one or more input objects, distinct from the first set of one or more input objects, for receiving an input of a second type associated with the operation of the surgical tool;

a first set of one or more magnets associated with the first set of one or more input objects;

a second set of one or more magnets associated with the second set of one or more input objects, the second set of one or more magnets including a third magnet and a fourth magnet; and a Hall effect sensor for detecting a magnetic field based on the first set of one or more magnets and the second set of one or more magnets;

wherein:

a magnetic axis of the third magnet is substantially parallel to a magnetic axis of the fourth magnet, or a magnetic axis of the third magnet is non-parallel to an axis extending between the third magnet and the fourth magnet.

19. The input device of claim 18, wherein the magnetic axis of the third magnet is substantially parallel to the magnetic axis of the fourth magnet.

20. The input device of claim 18, wherein the magnetic axis of the third magnet is non-parallel to the axis extending between the third magnet and the fourth magnet.

21. An input device for controlling an operation of a surgical tool, the input device comprising:

a first set of one or more input objects for receiving an input of a first type associated with the operation of the surgical tool;

a second set of one or more input objects, distinct from the first set of one or more input objects, for receiving an input of a second type associated with the operation of the surgical tool, the second set of one or more input objects including a third input object and a fourth input object;

a first set of one or more magnets associated with the first set of one or more input objects;

a second set of one or more magnets associated with the second set of one or more input objects, the second set of one or more magnets including a third magnet and a fourth magnet where the third magnet is rotatably coupled with the third input object and the fourth magnet is rotatably coupled with the fourth input object; and a Hall effect sensor for detecting a magnetic field based on the first set of one or more magnets and the second set of one or more magnets.

22. An input device for controlling an operation of a surgical tool, the input device comprising:

a first set of one or more input objects for receiving an input of a first type associated with the operation of the surgical tool;

a second set of one or more input objects, distinct from the first set of one or more input objects, for receiving an input of a second type associated with the operation of the surgical tool;

a first set of one or more magnets associated with the first set of one or more input objects, the first set of one or more magnets including a first magnet and a second magnet positioned on a first axis;

a second set of one or more magnets associated with the second set of one or more input objects, the second set of one or more magnets includes a third magnet and a fourth magnet positioned on a second axis substantially orthogonal to the first axis; and a Hall effect sensor for detecting a magnetic field based on the first set of one or more magnets and the second set of one or more magnets.

\* \* \* \* \*